US011358981B2

(12) United States Patent
Huang et al.

(10) Patent No.: US 11,358,981 B2
(45) Date of Patent: Jun. 14, 2022

(54) COMPOUNDS AND METHODS FOR SELECTIVE C-TERMINAL LABELING

(71) Applicant: Quantum-Si Incorporated, Guilford, CT (US)

(72) Inventors: Haidong Huang, Madison, CT (US); Roger Nani, Madison, CT (US); Omer Ad, Madison, CT (US); Robert E. Boer, Westbrook, CT (US)

(73) Assignee: Quantum-Si Incorporated, Guilford, CT (US)

( * ) Notice: Subject to any disclaimer, the term of this patent is extended or adjusted under 35 U.S.C. 154(b) by 0 days.

(21) Appl. No.: 17/153,490

(22) Filed: Jan. 20, 2021

(65) Prior Publication Data

US 2021/0221839 A1 Jul. 22, 2021

Related U.S. Application Data

(60) Provisional application No. 63/041,244, filed on Jun. 19, 2020, provisional application No. 62/964,075, filed on Jan. 21, 2020.

(51) Int. Cl.
  *C07K 1/107* (2006.01)
  *C07K 1/12* (2006.01)
  *C07K 14/195* (2006.01)

(52) U.S. Cl.
  CPC ............ *C07K 1/128* (2013.01); *C07K 14/195* (2013.01)

(58) Field of Classification Search
  None
  See application file for complete search history.

(56) References Cited

U.S. PATENT DOCUMENTS

| | | | |
|---|---|---|---|
| 5,707,804 A | 1/1998 | Mathies et al. |
| 5,851,840 A | 12/1998 | Sluka et al. |
| 6,153,442 A | 11/2000 | Pirio et al. |
| 6,248,518 B1 | 6/2001 | Parkhurst et al. |
| 6,255,083 B1 | 7/2001 | Williams |
| 6,762,048 B2 | 7/2004 | Williams |
| 6,787,308 B2 | 9/2004 | Balasubramanian et al. |
| 6,846,638 B2 | 1/2005 | Shipwash |
| 6,869,764 B2 | 3/2005 | Williams et al. |
| 6,936,702 B2 | 8/2005 | Williams et al. |
| 7,052,847 B2 | 5/2006 | Korlach et al. |
| 7,056,661 B2 | 6/2006 | Korlach et al. |
| 7,229,799 B2 | 6/2007 | Williams |
| 7,361,466 B2 | 4/2008 | Korlach et al. |
| 7,785,869 B2 | 8/2010 | Belgrader et al. |
| 7,968,702 B2 | 6/2011 | Wegener et al. |
| 8,034,623 B2 | 10/2011 | Oh et al. |
| 8,084,734 B2 | 12/2011 | Vertes et al. |
| 8,153,375 B2 | 4/2012 | Travers et al. |
| 8,192,961 B2 | 6/2012 | Williams |
| 8,252,910 B2 | 8/2012 | Korlach et al. |
| 8,257,954 B2 | 9/2012 | Clark et al. |
| 8,309,330 B2 | 11/2012 | Travers et al. |
| 8,354,252 B2 | 1/2013 | Wegener et al. |
| 8,420,366 B2 | 4/2013 | Clark et al. |
| 8,455,193 B2 | 6/2013 | Travers et al. |
| 8,530,154 B2 | 9/2013 | Williams |
| 8,581,179 B2 | 11/2013 | Franzen |
| 8,846,881 B2 | 9/2014 | Korlach et al. |
| 8,906,614 B2 | 12/2014 | Wegener et al. |
| 8,927,212 B2 | 1/2015 | Kong et al. |
| 8,980,584 B2 | 3/2015 | Williams |
| 9,062,091 B2 | 6/2015 | Bjornson et al. |
| 9,243,288 B2 | 1/2016 | Ness et al. |
| 9,404,146 B2 | 8/2016 | Travers et al. |
| 9,435,810 B2 | 9/2016 | Havranek et al. |
| 9,464,107 B2 | 10/2016 | Wegener et al. |
| 9,506,934 B2 | 11/2016 | Wong et al. |
| 9,542,527 B2 | 1/2017 | Travers et al. |
| 9,551,031 B2 | 1/2017 | Korlach et al. |
| 9,551,660 B2 | 1/2017 | Kong et al. |
| 9,566,335 B1 | 2/2017 | Emili et al. |
| 9,582,640 B2 | 2/2017 | Travers et al. |
| 9,600,626 B2 | 3/2017 | Travers et al. |
| 9,678,080 B2 | 6/2017 | Bjornson et al. |
| 9,719,073 B2 | 8/2017 | Emig et al. |
| 9,845,501 B2 | 12/2017 | Williams |
| 9,879,319 B2 | 1/2018 | Korlach et al. |
| 9,910,956 B2 | 3/2018 | Travers et al. |
| 9,957,291 B2 | 5/2018 | Sebo et al. |
| 10,023,605 B2 | 7/2018 | Bjornson et al. |

(Continued)

FOREIGN PATENT DOCUMENTS

| | | |
|---|---|---|
| EP | 3733687 A1 | 11/2020 |
| WO | WO 2005/044836 A2 | 5/2005 |

(Continued)

OTHER PUBLICATIONS

Schoffelen, Sanne et al; "Metal-free and ph-controlled introduction of azides in proteins." Chem. Sci. (2011) 2 p. 701-705.*
Koushik et al., Cerulean, Venus, and VenusY67C FRET reference standards. Biophys J. Dec. 15, 2006;91(12):L99-L101. doi: 10.1529/biophysj.106.096206. Epub Oct. 13, 2006. PMID: 17040988; PMCID: PMC1779932.
Saito et al., Dual-labeled oligonucleotide probe for sensing adenosine via FRET: a novel alternative to SNPs genotyping. Chem Commun (Camb). Jun. 7, 2007;(21):2133-5. doi: 10.1039/b618465k. Epub Feb. 28, 2007. PMID: 17520113.
Sato et al., Polyproline-rod approach to isolating protein targets of bioactive small molecules: isolation of a new target of indomethacin. J Am Chem Soc. Jan. 31, 2007; 129(4):873-80. doi: 10.1021/ja0655643. PMID: 17243824.
Stryer et al., Energy transfer: a spectroscopic ruler. Proc Natl Acad Sci U S A. Aug. 1967;58(2):719-26. doi: 10.1073/pnas.58.2.719. PMID: 5233469; PMCID: PMC335693.

(Continued)

*Primary Examiner* — Fred H Reynolds
(74) *Attorney, Agent, or Firm* — Wolf, Greenfield & Sacks, P.C.

(57) ABSTRACT

The present disclosure relates to compounds and methods for selective C-terminal functionalization of peptides. In certain embodiments, the compounds have improved water-solubility, and are suitable for use in connection with peptide sequencing methodologies.

16 Claims, 34 Drawing Sheets

Specification includes a Sequence Listing.

(56) References Cited

U.S. PATENT DOCUMENTS

| | | |
|---|---|---|
| 10,066,258 B2 | 9/2018 | Kong et al. |
| 10,150,872 B2 | 12/2018 | Zheng et al. |
| 10,161,002 B2 | 12/2018 | Korlach et al. |
| 10,481,162 B2 | 11/2019 | Emili et al. |
| 10,544,449 B2 | 1/2020 | Shen et al. |
| 10,545,153 B2 | 1/2020 | Marcotte et al. |
| 10,570,445 B2 | 2/2020 | Kong et al. |
| 10,676,788 B2 | 6/2020 | Shen et al. |
| 10,745,750 B2 | 8/2020 | Korlach et al. |
| 10,787,573 B2 | 9/2020 | Zheng et al. |
| 2005/0042633 A1 | 2/2005 | Williams |
| 2005/0266456 A1 | 12/2005 | Williams et al. |
| 2007/0072196 A1 | 3/2007 | Xu et al. |
| 2007/0219367 A1 | 9/2007 | Shchepinov et al. |
| 2009/0263802 A1 | 10/2009 | Drmanac |
| 2010/0009872 A1 | 1/2010 | Eid et al. |
| 2010/0029494 A1 | 2/2010 | Cherkasov et al. |
| 2010/0035254 A1 | 2/2010 | Williams |
| 2011/0003343 A1 | 1/2011 | Nikiforov et al. |
| 2011/0281776 A1 | 11/2011 | Eshoo et al. |
| 2012/0322692 A1 | 12/2012 | Pham et al. |
| 2013/0316912 A1 | 11/2013 | Bjornson et al. |
| 2014/0370519 A1 | 12/2014 | Vangbo et al. |
| 2016/0367991 A1 | 12/2016 | Petersen et al. |
| 2017/0136433 A1 | 5/2017 | Sun et al. |
| 2018/0211003 A1 | 7/2018 | Travers et al. |
| 2018/0299460 A1 | 10/2018 | Emili |
| 2018/0346507 A1 | 12/2018 | Sebo et al. |
| 2019/0010183 A1 | 1/2019 | Bjornson et al. |
| 2019/0249153 A1 | 8/2019 | Kamtekar et al. |
| 2020/0141944 A1 | 5/2020 | Emili et al. |
| 2020/0148727 A1 | 5/2020 | Tullman et al. |
| 2021/0134855 A1 | 5/2021 | Ghasemi et al. |
| 2021/0331170 A1 | 10/2021 | Rothberg et al. |
| 2021/0354134 A1 | 11/2021 | Rothberg et al. |
| 2021/0379591 A1 | 12/2021 | Rothberg et al. |

FOREIGN PATENT DOCUMENTS

| | | | |
|---|---|---|---|
| WO | WO 2007/070572 A2 | 6/2007 | |
| WO | WO 2010/065322 A1 | 6/2010 | |
| WO | WO 2010/115016 A2 | 10/2010 | |
| WO | WO 2019/040825 A1 | 2/2019 | |

OTHER PUBLICATIONS

Williams et al., An artificial processivity clamp made with streptavidin facilitates oriented attachment of polymerase-DNA complexes to surfaces. Nucleic Acids Res. Oct. 2008;36(18):e121. doi: 10.1093/nar/gkn531. Epub Aug. 22, 2008. PMID: 18723573; PMCID: PMC2566871.

Invitation to Pay Additional Fees dated May 10, 2021 for Application No. PCT/US2021/014189.

International Search Report and Written Opinion dated Jul. 2, 2021 for Application No. PCT/US2021/014189.

International Search Report and Written Opinion dated Aug. 16, 2021 for Application No. PCT/US2021/028471.

[No Author Listed] Broadpharm: "Safety Data Sheet Section I. Identification of the substance Product Name: Aminooxy-PEG1-azide Catalog No. BP-23596 Supplier", Dec. 5, 2017 (Dec. 5, 2017), p. 1, XP055799388, Retrieved from the Internet: URL:https://broadpharm.com/web3/images/MSDS PDF/MSDS%20BP-23596.pdf [retrieved on Apr. 28, 2021] the whole document.

Fabricius et al., Rapid and efficient C-terminal labeling of nanobodies for DNA-PAINT. Journal of Physics D: Applied Physics. Oct. 19, 2018;51(47):474005.

Glaser et al., Methods for 18F-labeling of RGD peptides: comparison of aminooxy [18F]fluorobenzaldehyde condensation with 'click labeling' using 2-[18F]fluoroethylazide, and S-alkylation with [18F]fluoropropanethiol. Amino Acids. Oct. 2009;37(4):717-24. doi: 10.1007/s00726-008-0200-0. Epub Nov. 15, 2008.

McKay et al., Click chemistry in complex mixtures: bioorthogonal bioconjugation. Chem Biol. Sep. 18, 2014;21(9):1075-101. doi: 10.1016/j.chembiol.2014.09.002.

Nakajima et al., Mass spectrometry-based sequencing of protein C-terminal peptide using α-carboxyl group-specific derivatization and COOH capturing. Analytical biochemistry. Sep. 15, 2012;428(2):167-72.

Patterson et al., Finding the right (bioorthogonal) chemistry. ACS Chem Biol. Mar. 21, 2014;9(3):592-605. doi: 10.1021/cb400828a. Epub Jan. 30, 2014.

Xu et al., Chemoenzymatic labeling of protein C-termini for positive selection of C-terminal peptides. ACS Chem Biol. Oct. 21, 2011;6(10):1015-20. doi: 10.1021/cb200164h. Epub Aug. 10, 2011. Author Manuscript, 12 pages.

Zhang et al., Protein C-terminal modification through thioacid/azide amidation. Bioconjug Chem. Feb. 2009;20(2):197-200. doi: 10.1021/bc800488n.

Zhang et al., Recent progress in quantitative glycoproteomics. Glycoconj J. Aug. 2012;29(5-6):249-58. doi: 10.1007/s10719-012-9398-x. Epub Jun. 15, 2012.

* cited by examiner

Reaction 3

Reaction 4

*Q24 DNA Linker*

*Peptide-Q24ds-SV complex*

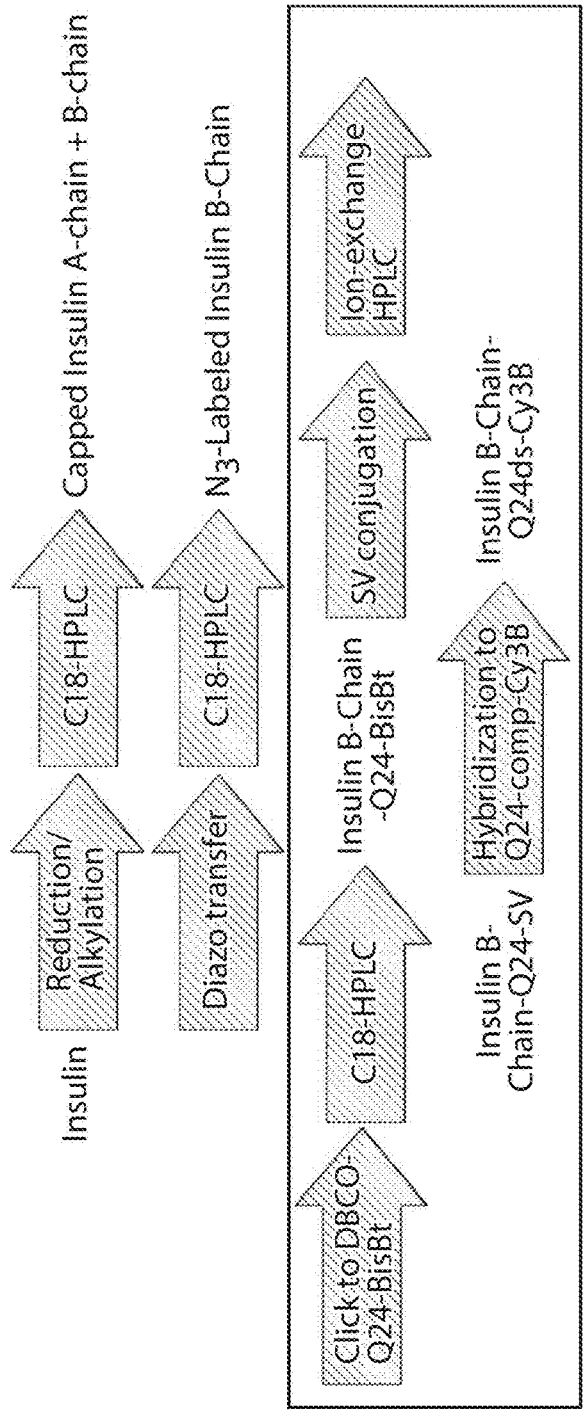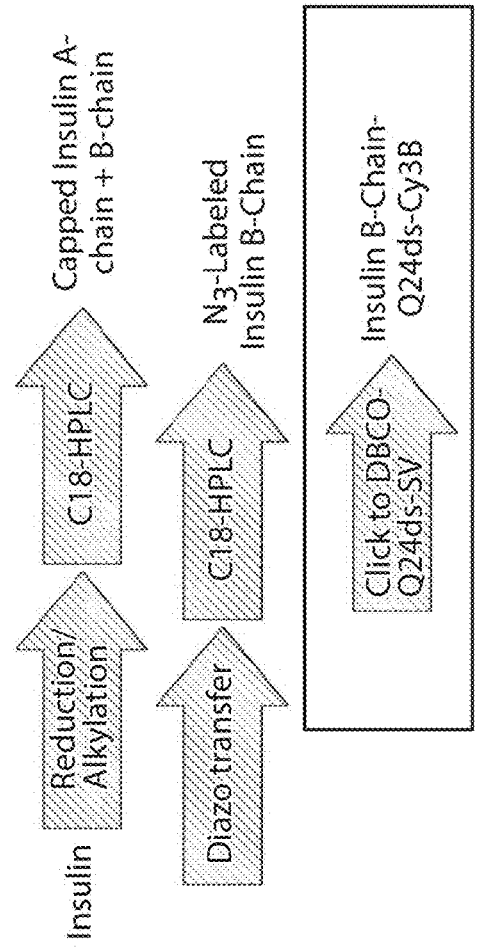
FIG. 22A
FIG. 22B

SEQUENCE LISTING

<160> NUMBER OF SEQ ID NOS: 13

<210> SEQ ID NO 1
<211> LENGTH: 18
<212> TYPE: PRT
<213> ORGANISM: Artificial Sequence
<220> FEATURE:
<223> OTHER INFORMATION: Synthetic

<400> SEQUENCE: 1

Ile Asn Thr Ile Tyr Leu Gly Gly Pro Phe Ser Pro Asn Val Leu Asn
1               5                   10                  15

Trp Arg

<210> SEQ ID NO 2
<211> LENGTH: 25
<212> TYPE: DNA
<213> ORGANISM: Artificial Sequence
<220> FEATURE:
<223> OTHER INFORMATION: Synthetic

<400> SEQUENCE: 2
ccacgcgtgg aacccttggg atcca                                              25

<210> SEQ ID NO 3
<211> LENGTH: 22
<212> TYPE: PRT
<213> ORGANISM: Artificial Sequence
<220> FEATURE:
<223> OTHER INFORMATION: Synthetic

<400> SEQUENCE: 3

Leu Leu Cys Phe Leu Val Leu Thr Ser Leu Ser His Ala Phe Gly Gln
1               5                   10                  15

Thr Asp Met Ser Arg Lys
            20

<210> SEQ ID NO 4
<211> LENGTH: 13
<212> TYPE: PRT
<213> ORGANISM: Artificial Sequence
<220> FEATURE:
<223> OTHER INFORMATION: Synthetic

<400> SEQUENCE: 4

Tyr Ala Ala Trp Ala Ala Phe Ala Asp Asp Asp Trp Lys
1               5                   10

<210> SEQ ID NO 5
<211> LENGTH: 6
<212> TYPE: PRT
<213> ORGANISM: Artificial Sequence
<220> FEATURE:
<223> OTHER INFORMATION: Synthetic

<400> SEQUENCE: 5

Ala Asp Asp Asp Trp Lys
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic

<400> SEQUENCE: 6

Asp Asp Asp Trp Lys
1               5

<210> SEQ ID NO 7
<211> LENGTH: 10
<212> TYPE: PRT
<213> ORGANISM: Artificial Sequence
<220> FEATURE:

```
<223> OTHER INFORMATION: Synthetic

<400> SEQUENCE: 7

Gly Tyr Ser Ile Phe Ser Tyr Ala Thr Lys
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic

<400> SEQUENCE: 8

Lys Leu Ile Ser Glu Glu Asp Leu Lys Ala Arg
1               5                   10

<210> SEQ ID NO 9
<211> LENGTH: 223
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (31)..(31)
<223> OTHER INFORMATION: X may be Lys or Glu

<400> SEQUENCE: 9

Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Xaa Ser
                20                  25                  30

Asp Thr Ser Tyr Val Ser Leu Lys Ala Pro Leu Thr Lys Pro Leu Lys
            35                  40                  45

Ala Phe Thr Val Cys Leu His Phe Tyr Thr Glu Leu Ser Ser Thr Arg
        50                  55                  60

Gly Tyr Ser Ile Phe Ser Tyr Ala Thr Lys Arg Gln Asp Asn Glu Ile
65                  70                  75                  80

Leu Ile Phe Trp Ser Lys Asp Ile Gly Tyr Ser Phe Thr Val Gly Gly
                85                  90                  95

Ser Glu Ile Leu Phe Glu Val Pro Glu Val Thr Val Ala Pro Val His
                100                 105                 110

Ile Cys Thr Ser Trp Glu Ser Ala Ser Gly Ile Val Glu Phe Trp Val
            115                 120                 125

Asp Gly Lys Pro Arg Val Arg Lys Ser Leu Lys Lys Gly Tyr Thr Val
        130                 135                 140

Gly Ala Glu Ala Ser Ile Ile Leu Gly Gln Glu Gln Asp Ser Phe Gly
145                 150                 155                 160

Gly Asn Phe Glu Gly Ser Gln Ser Leu Val Gly Asp Ile Gly Asn Val
                165                 170                 175

Asn Met Trp Asp Phe Val Leu Ser Pro Asp Glu Ile Asn Thr Ile Tyr
                180                 185                 190

Leu Gly Gly Pro Phe Ser Pro Asn Val Leu Asn Trp Arg Ala Leu Lys
            195                 200                 205

Tyr Glu Val Gln Gly Glu Val Phe Thr Lys Pro Gln Leu Trp Pro
        210                 215                 220

<210> SEQ ID NO 10
<211> LENGTH: 6
```

```
<212> TYPE: PRT
<213> ORGANISM: Artificial Sequence
<220> FEATURE:
<223> OTHER INFORMATION: Synthetic

<400> SEQUENCE: 10

Ala Phe Val Phe Pro Lys
1               5

<210> SEQ ID NO 11
<211> LENGTH: 12
<212> TYPE: PRT
<213> ORGANISM: Artificial Sequence
<220> FEATURE:
<223> OTHER INFORMATION: Synthetic

<400> SEQUENCE: 11

Arg Gln Asp Asn Glu Ile Leu Ile Phe Trp Ser Lys
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic

<400> SEQUENCE: 12

Glu Ser Asp Thr Ser Tyr Val Ser Leu Lys
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic

<400> SEQUENCE: 13

Tyr Glu Val Gln Gly Glu Val Phe Thr Lys
1               5                   10
```

COMPOUNDS AND METHODS FOR SELECTIVE C-TERMINAL LABELING

CROSS REFERENCE TO RELATED APPLICATIONS

This application claims priority under 35 U.S.C. § 119(e) to U.S. provisional patent applications U.S. Ser. No. 62/964,075, filed Jan. 21, 2020, and U.S. Ser. No. 63/041,244, filed Jun. 19, 2020, the entire contents of which are incorporated herein by reference.

TECHNICAL FIELD

The present disclosure relates to compounds and methods for selective C-terminal functionalization of peptides. In certain embodiments, the compounds have improved water-solubility, and are suitable for use in connection with peptide sequencing methodologies.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Mar. 31, 20, is named R070870091US02-SEQ and is 4 kilobytes in size.

BACKGROUND

Array-based platforms are widely used in massively parallel technologies for detecting and analyzing biomolecules, such as proteins and peptides. Examples of these platforms include microarrays used in biosensing and pixel arrays used in single molecule sequencing. Arrays generally include a collection of exceptionally small regions on the surface of a single device, with each region capable of independently assaying a sample. These regions can include selectively functionalized surface portions that are reactive toward a complementary functional moiety of a biomolecule, which permits immobilization of the biomolecule to the surface.

SUMMARY

In one aspect, the present disclosure provides a method of selective C-terminal functionalization of a peptide, comprising:

a. reacting a plurality of peptides of Formula (I):

P—R(CO$_2$H)$_n$      (I)

or salts thereof;
with a compound of Formula (II):

HX-L$_1$-R$_1$      (II)

to obtain a plurality of compounds of Formula (III):

P—R$+$CO—X—L$_1$—R$_1$]$_n$      (III)

or salts thereof; and
b. reacting the plurality of compounds of Formula (III), or salts thereof, with a compound of Formula (IV):

R$_2$-L$_2$-Z      (IV)

to obtain a plurality of compounds of Formula (V):

P—R$+$CO—X—L$_1$—Y—L$_2$—Z]$_n$      (V)

or salts thereof; wherein m, n, P, R(CO$_2$H)$_n$, HX, X, L$_1$, L$_2$, R$_1$, R$_2$, Y and Z are defined herein.

In another aspect, the present disclosure provides a method of selective C-terminal amine functionalization of a peptide, comprising:

a. reacting a plurality of peptides of Formula (VI):

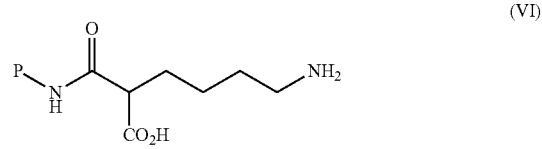

or salts thereof, with a compound of Formula (VII):

to obtain a plurality of compounds of Formula (VIII):

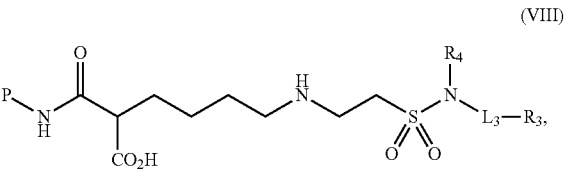

or salts thereof; and
b. reacting the plurality of compounds of Formula (VIII), or salts thereof, with a compound of Formula (IX):

R$_5$-L$_4$-Z$_1$;      (IX)

to afford a plurality of compounds of Formula (X):

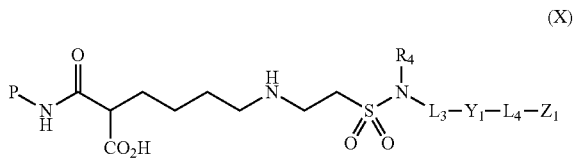

or salts thereof; wherein P, L$_3$, L$_4$, R$_3$, R$_4$, Y$_1$, and Z$_1$ are as defined herein.

In another aspect, the present disclosure provides a method of selective N-functionalization of a peptide, comprising reacting a plurality of peptides of Formula (XI):

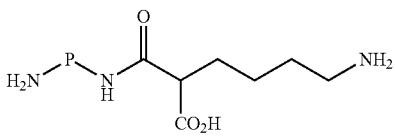

(XI)

or salts thereof, wherein each P independently is a peptide having an N-terminal amine, with a compound of Formula (XII):

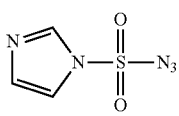

(XII)

under conditions (a), comprising $Cu^{2+}$ and a buffer having a pH of about 7-8.5; to obtain a plurality of N-terminal azido compounds of Formula (XIIIa):

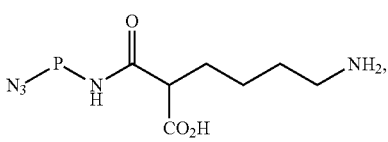

(XIIIa)

or salts thereof; or under conditions (b), comprising $Cu^{2+}$ and a buffer having a pH of about 10-11; to obtain a plurality of ε-azido compounds of the Formula (XIIIb):

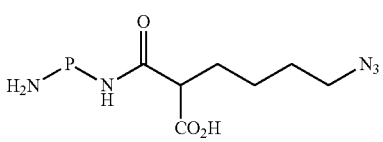

(XIIIb)

or salts thereof, wherein P is as defined herein.

In some embodiments, the method further comprises reacting the plurality of compounds of Formula (XIIIb) or salts thereof with a compound of Formula (XIV):

(XIV)

wherein $R_6$ is a moiety comprising an alkyne or a strained alkene; $L_5$ is a linker or is absent; and $Z_2$ is a water-soluble moiety;

to obtain a plurality of compounds of Formula (XV), or salts thereof:

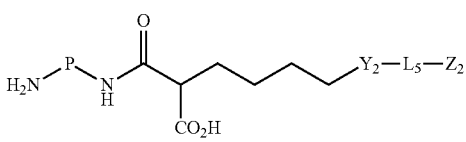

(XV)

wherein $Y_2$ is a moiety resulting from a click reaction with the azide moiety of Formula (XIIIb) and $R_6$.

In some aspects, the present disclosure provides a method of selective functionalization in accordance with any one of the methods described herein, wherein the method comprises reacting a single peptide molecule in place of a plurality of peptides. Accordingly, in some embodiments, the method comprises reacting a single polypeptide of any one of Formulae (I), (VI), and (XI) in accordance with the methods described herein.

BRIEF DESCRIPTION OF THE DRAWINGS

FIG. 3A shows representative functionalization of aspartic acid and glutamic acid terminated peptides. FIG. 3B shows representative functionalization of lysine and arginine terminated peptides. FIG. 3C shows an exemplary protection of sulfide moieties prior to functionalization of a lysine terminated peptide (Reaction 1), and an example of competitive intramolecular cyclization, which can be overcome using high concentrations of nucleophile and coupling reagent (Reaction 2). FIG. 3D shows model functionalization of a lysine terminated peptide (Reaction 3), and model functionalization of an arginine terminated peptide having internal glutamic acid and aspartic acid residues (Reaction 4).

FIG. 5A and FIG. 5B show binding events to the N-terminus of QP126. The red arrow denotes when enzyme (peptidase) is added, after which a change in pulsing behavior is observed due to binding of the ClpS (ATP-dependent Clp protease adaptor protein) to a different amino acid. FIG. 5C shows full length CRP (C-reactive protein) sequence with bold fragments that were tagged.

FIG. 7A shows site-selective diazo transfer. FIG. 7B shows site-selective diazo transfer using a dipeptide followed by hydrolysis.

FIG. 10A shows a representative example of peptide sequencing by iterative cycles of terminal amino acid recognition and cleavage. FIG. 10B shows a representative example of dynamic peptide sequencing using a labeled amino acid recognition molecule and an exopeptidase in a single reaction mixture.

FIG. 22A-B show sample preparation workflows: FIG. 22A shows version 1 of an insulin sample preparation with a 5-step protocol for preparing the final peptide conjugate. FIG. 22B shows version 2 of an insulin sample preparation with improved 1-step conjugate.

DETAILED DESCRIPTION

Figure 1:
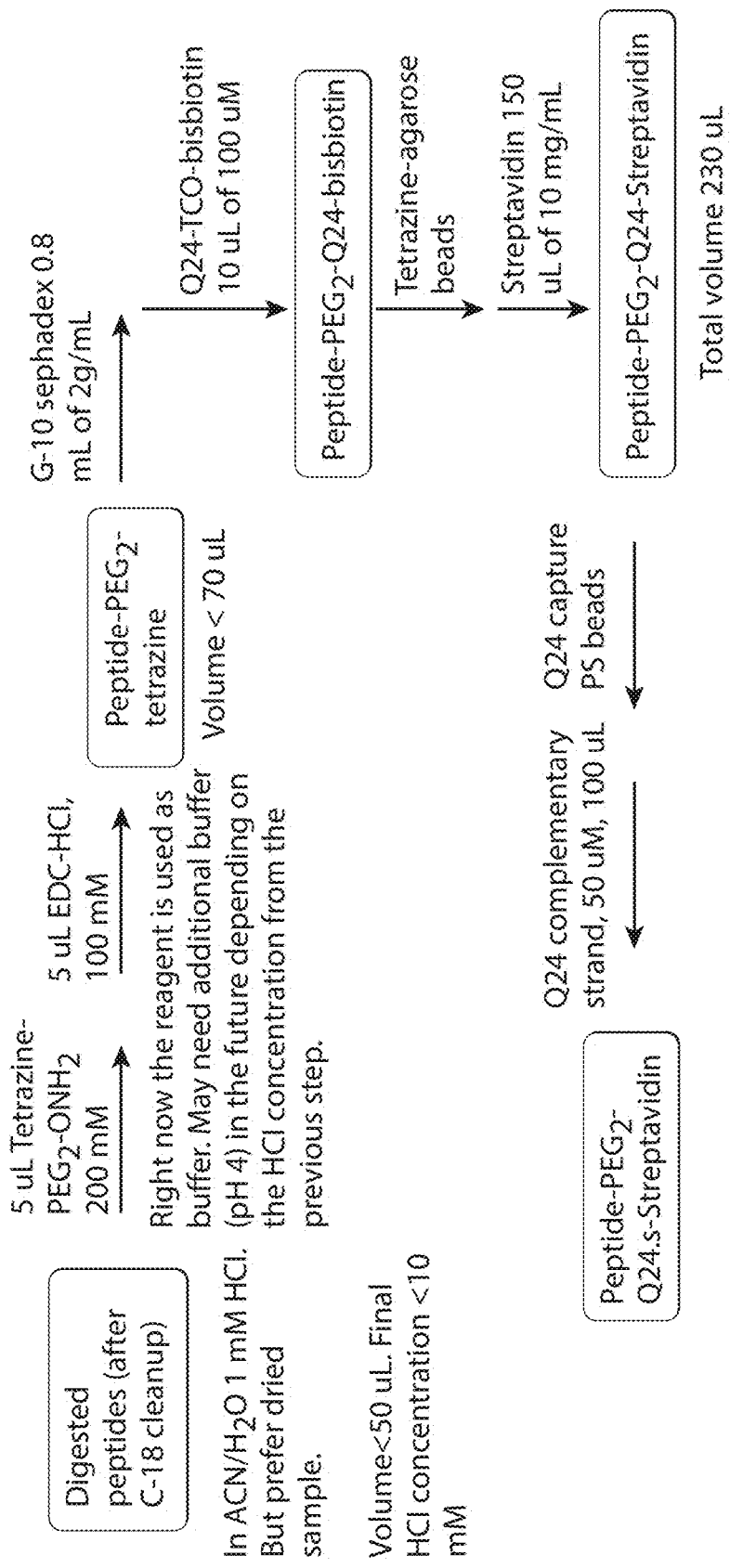
FIG. 1. shows a representative C-terminal carboxylate coupling procedure.
Figure 2:
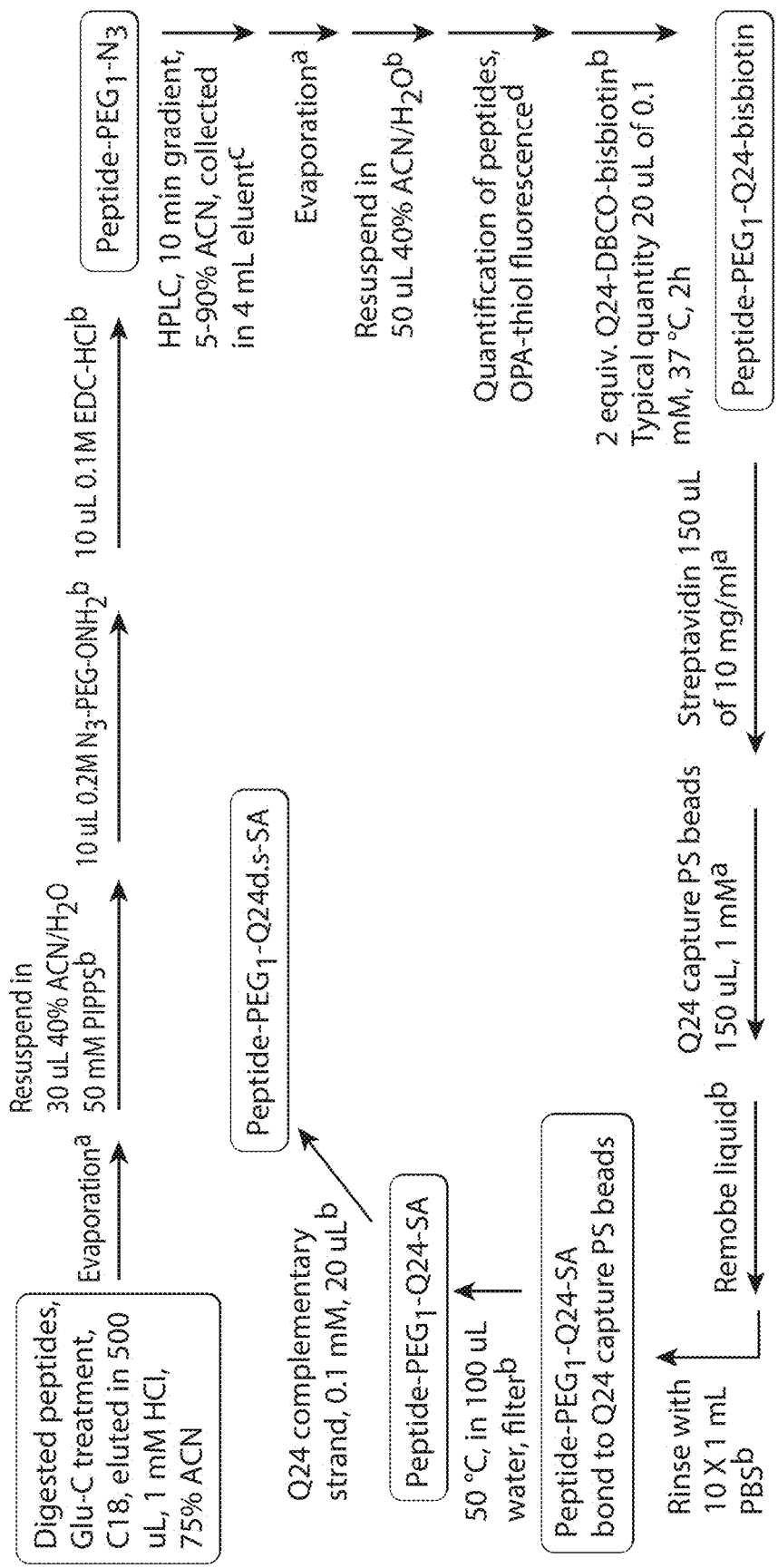
FIG. 2. shows a representative C-terminal carboxylate coupling procedure.
Figure 3A:
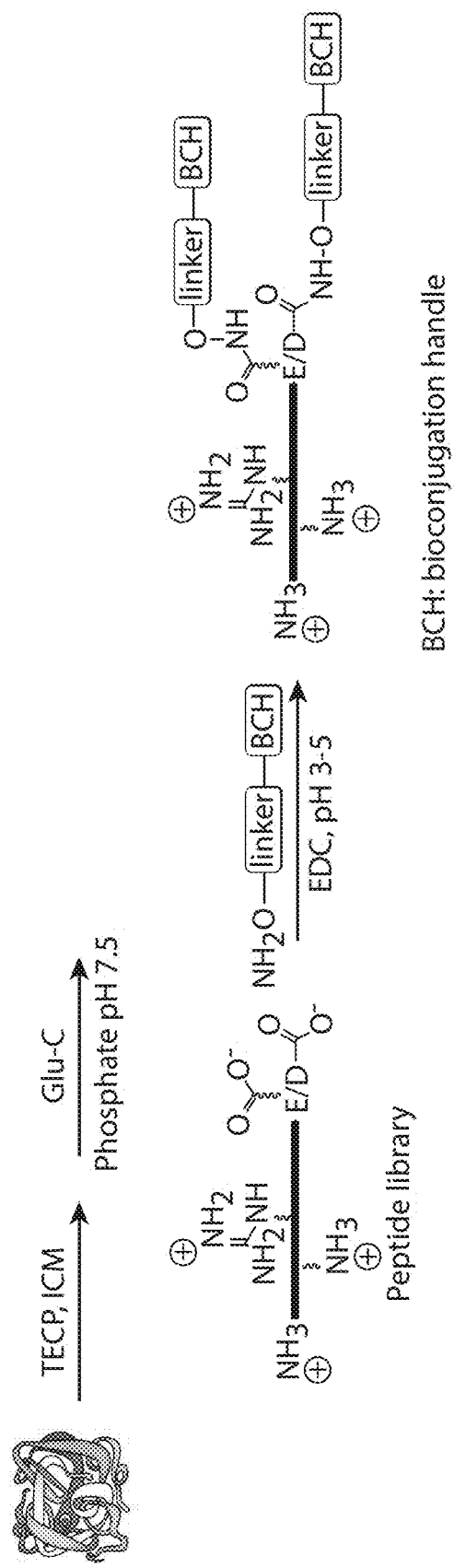
FIG. 3A-D. show representative C-terminal coupling procedures.
Figure 3B:
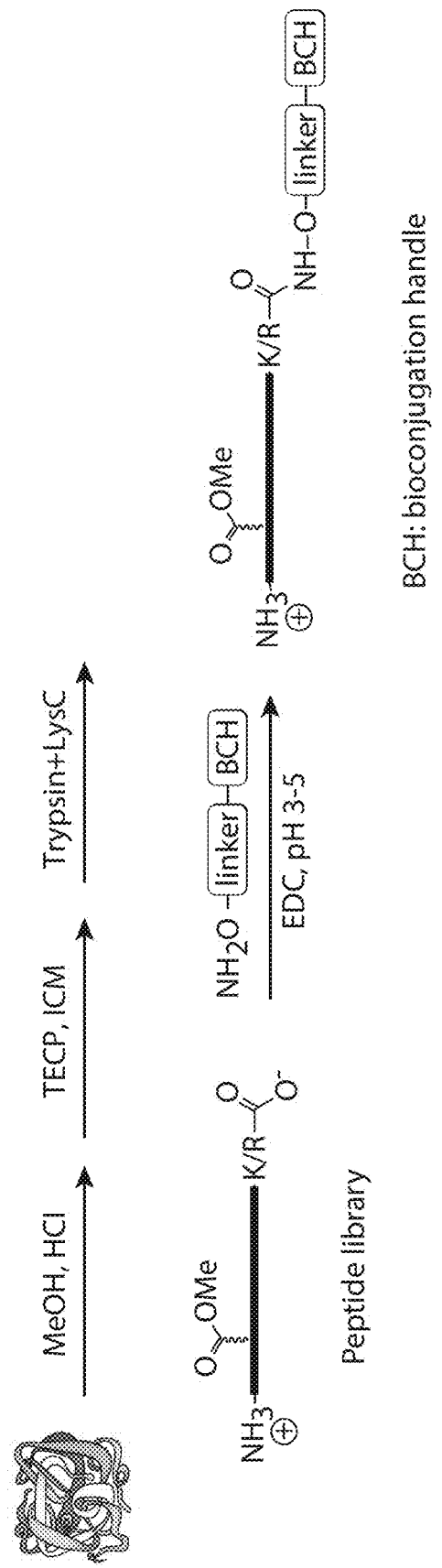
Figure 3C:
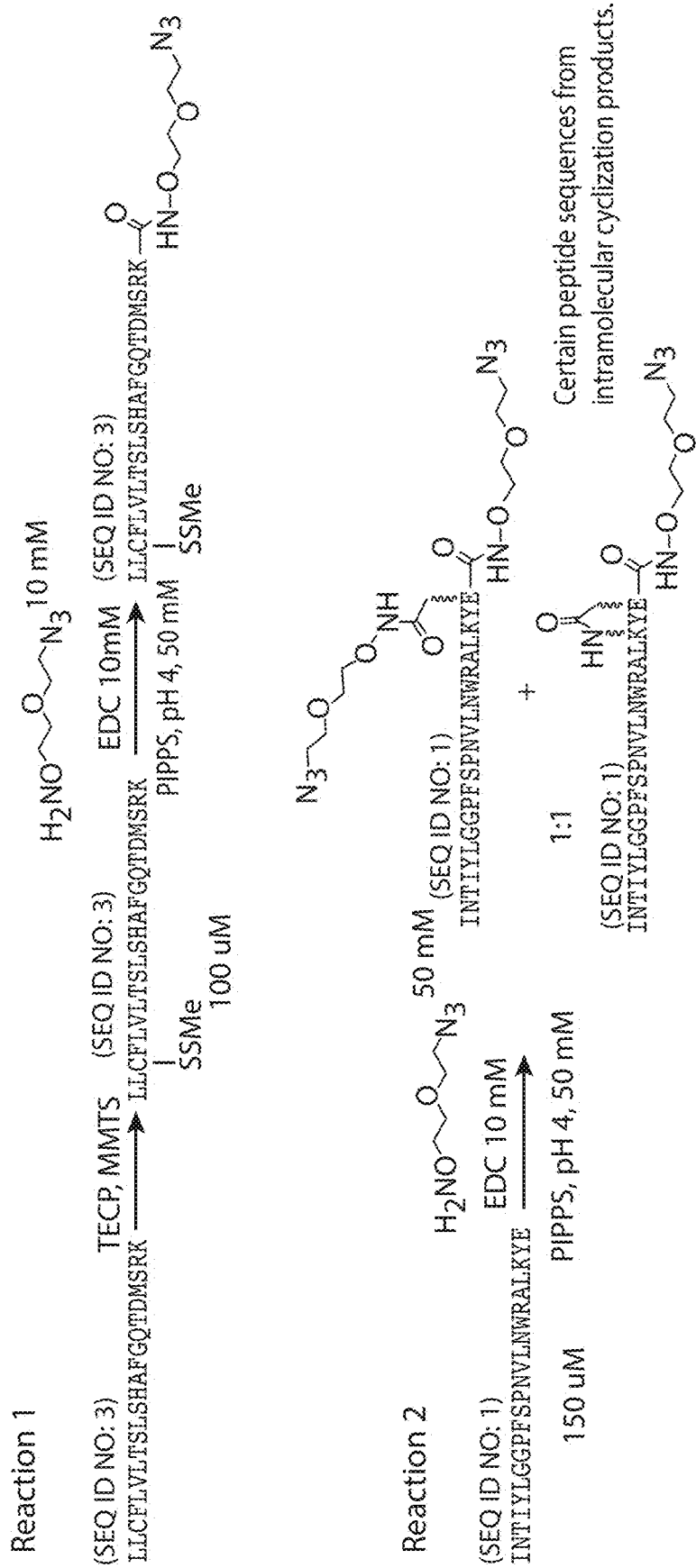
Figure 3D:
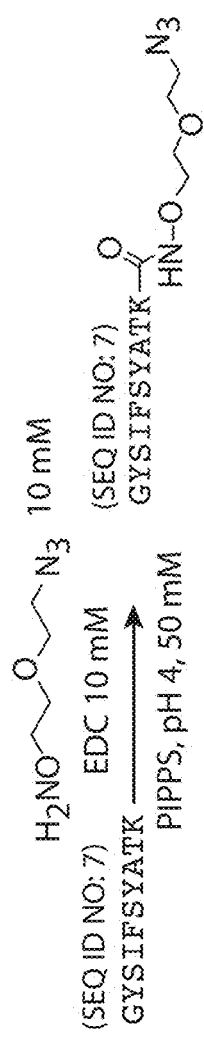
Figure 3D:
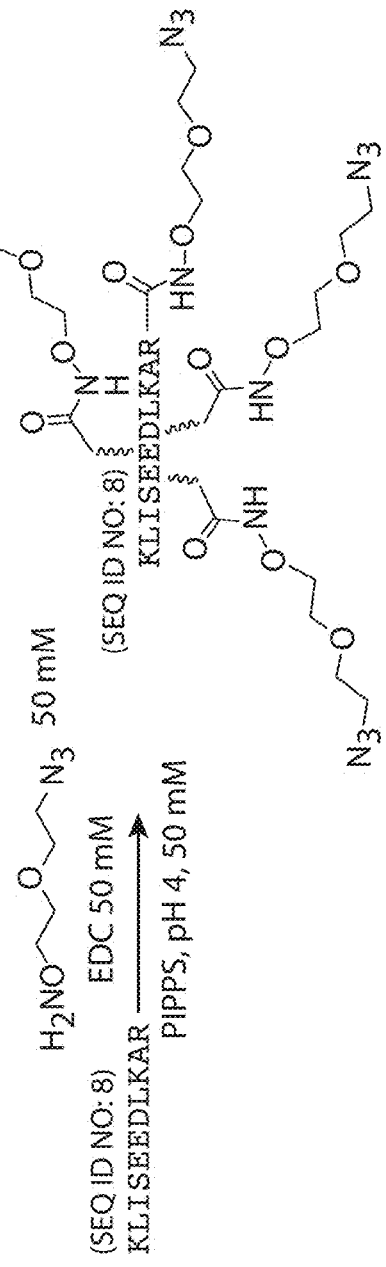

Aspects of the disclosure relate to methods and compositions for functionalizing a peptide, e.g., a single peptide molecule or a plurality of peptide molecules. In some embodiments, the disclosure relates to the functionalization of a terminal end or an amino acid side-chain of a peptide. In some embodiments, as described herein, functionalization can impart an attachment functionality to the peptide. For example, in some embodiments, a functionalized peptide in accordance with the application comprises a functional moiety (e.g., biotin or bis-biotin) configured for attachment to a complementary functional moiety (e.g., an avidin protein). In some embodiments, the complementary functional moiety is attached to a surface.

Accordingly, in some aspects, the disclosure relates to preparing a peptide for immobilization to a surface. In some aspects, the disclosure provides methods of immobilizing peptides to a surface of a solid support. In some embodiments, the solid support comprises a plurality of sample wells formed at the surface of the solid support. In some embodiments, each sample well of the plurality is configured to immobilize a single peptide molecule therein. In some embodiments, a plurality of peptides is contacted to the solid support to prepare an array of sample wells, where each sample well contains a single peptide molecule attached to a surface of the sample well.

In some embodiments, methods and compositions provided herein can be used to modify a terminal end or other functional group of a peptide with one or more water-soluble moieties that enhance solubility of the peptide in an aqueous solution. In some embodiments, a water-soluble moiety is useful for short peptides that result from fragmentation of a protein (e.g., via enzymatic digestion, as described herein), as short peptides are relatively insoluble in an aqueous solution. For example, in some embodiments, functionalization of a peptide (or a plurality of peptides) can comprise conjugating a water-soluble moiety to the polypeptides. Examples of water-soluble moieties include, without limitation, oligonucleotides, single- or double-stranded nucleic acids (e.g., comprising DNA, RNA, and variants thereof), polyol and polyether compounds (e.g., PEG), sugar polymers, and other charged polymers.

Methods

C-Terminal Carboxylate Functionalization

In one aspect, the present disclosure provides a method of selective C-terminal functionalization of a peptide, comprising:

a. reacting a plurality of peptides of Formula (I):

P—R(CO$_2$H)$_n$ (I)

or salts thereof;
with a compound of Formula (II):

HX-L$_1$-R$_1$ (II)

to obtain a plurality of compounds of Formula (III):

P—R—[CO—X—L$_1$—R$_1$]$_n$ (III)

or salts thereof; and b. reacting the plurality of compounds of Formula (III), or salts thereof, with a compound of Formula (IV):

R$_2$-L$_2$-Z (IV)

to obtain a plurality of compounds of Formula (V):

P—R—[CO—X—L$_1$—Y—L$_2$—Z]$_n$ (V)

or salts thereof; wherein m, n, P, R(CO$_2$H)$_n$, HX, X, L$_1$, L$_2$, R$_1$, R$_2$, Y and Z are defined as follows.

m is an integer of 1-25, inclusive. In certain embodiments, m is 1-10, inclusive. In certain embodiments, m is 5-10, inclusive. In certain embodiments, m is 1-5, inclusive. In certain embodiments, m is 1, 2, 3, 4, 5, 6, 7 8 9, 10, 11, 12, 13, 14, 15, 16, 17, 18, 19, 20, 21, 22, 23, 24, or 25.

n is 1 or 2. In certain embodiments, n is 1. In certain embodiments, n is 2.

Each P independently is a peptide. In certain embodiments, P has 2-100 amino acid residues. In certain embodiments, P has 2-30 amino acid residues.

Each R(CO$_2$H)$_n$ independently is an amino acid residue having n carboxylate moieties. n is 1 or 2. In certain embodiments, n is 1. When n is 1, R(CO$_2$H)$_n$ is lysine or arginine. In a particular embodiment, R(CO$_2$H)$_n$ is lysine. In another particular embodiment, R(CO$_2$H)$_n$ is arginine. In certain embodiments, n is 2. When n is 2, R(CO$_2$H)$_n$ is glutamic acid or aspartic acid. In a particular embodiment, R(CO$_2$H)$_n$ is glutamic acid. In another particular embodiment, R(CO$_2$H)$_n$ is aspartic acid.

HX is nucleophilic moiety that is capable of being acylated, wherein H is a proton. X is one or more heteroatoms. In certain embodiments, X is O, S, or NH, or NO.

L$_1$ is a linker. In certain embodiments, L$_1$ is a substituted or unsubstituted aliphatic chain, wherein one or more carbon atoms are optionally, independently replaced by a heteroatom, an aryl, heteroaryl, cycloalkyl, or heterocyclyl moiety. In certain embodiments, L$_1$ is polyethylene glycol (PEG). In other embodiments, L$_1$ is a peptide, or an oligonucleotide. In certain embodiments, L$_1$ is less than 5 nm. In certain embodiments L$_1$ is less than 1 nm.

L$_2$ is a linker, or is absent. In certain embodiments, L$_2$ is absent. In certain embodiments, L$_2$ is a substituted or unsubstituted aliphatic chain, wherein one or more carbon atoms are optionally, independently replaced by a heteroatom, an aryl, heteroaryl, cycloalkyl, or heterocyclyl moiety. In certain embodiments, L$_2$ is polyethylene glycol (PEG). In other embodiments, L$_2$ is a peptide, or an oligonucleotide. In certain embodiments L$_2$ is between 5-20 nm, inclusive.

R$_1$ is a moiety comprising a click chemistry handle. In certain embodiments, R$_1$ is a moiety comprising an azide, tetrazine, nitrile oxide, alkyne or strained alkene. In certain embodiments, the alkyne is a primary alkyne. In certain embodiments, the alkyne is a cyclic (e.g., mono- or polycyclic) alkyne (e.g., diarylcyclooctyne, or bicycle[6.1.0]nonyne). In certain embodiments, the strained alkene is trans-cyclooctene. In certain embodiments, R$_1$ is a moiety comprising an azide. In certain embodiments, the tetrazine comprises the structure:

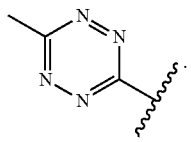 [SMILES: *c1nnc(C)nn1]

R$_2$ is a moiety comprising a click chemistry handle that is complementary to R$_1$. The click chemistry handle of R$_2$ is capable of undergoing a click reaction (i.e., an electrocyclic reaction to form a 5-membered heterocyclic ring) with R$_1$. For example, when R$_1$ comprises an azide, nitrile oxide, or a tetrazine, then R$_2$ may comprise an alkyne or a strained alkene. Conversely, when R$_1$ comprises an alkyne or a strained alkene, then R$_2$ may comprise an azide, nitrile oxide, or tetrazine. In certain embodiments, R$_2$ is a moiety comprising an azide, tetrazine, nitrile oxide, alkyne or strained alkene. In certain embodiments, the alkyne is a primary alkyne. In certain embodiments, the alkyne is a cyclic (e.g., mono- or polycyclic) alkyne (e.g., diarylcyclooctyne, or bicycle[6.1.0]nonyne). In certain particular embodiments, R$_2$ comprises BCN. In other particular embodiments, R$_2$ comprises DBCO. In certain embodiments, the strained alkene is trans-cyclooctene. In certain embodiments, the tetrazine comprises the structure:

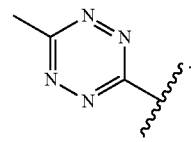 [SMILES: *c1nnc(C)nn1]

Y is a moiety resulting from the click reaction of R$_1$ and R$_2$. Y is a 5-membered heterocyclic ring resulting from an electrocyclic reaction (e.g., 3+2 cycloaddition, or 4+2 cycloaddition) between the reactive click chemistry handles of R$_1$ and R$_2$. In certain embodiments, Y is a diradical comprising a 1,2,3-triazolyl, 4,5-dihydro-1,2,3-triazolyl, isoxazolyl, 4,5-dihydroisoxazolyl, or 1,4-dihydropyridazyl moiety.

Z is a water-soluble moiety. In certain embodiments, Z imparts water-solubility to the compound to which it is attached. In certain embodiments, Z comprises polyethylene glycol (PEG). In certain embodiments, Z comprises single-stranded DNA. In certain particular embodiments, Z comprises Q24. In certain embodiments, Z comprises double-stranded DNA. In certain embodiments (e.g., compounds of Formula (V)), Z further comprises biotin (e.g., bisbiotin). When Z comprises biotin (e.g., bisbiotin), Z may further comprise streptavidin. In certain embodiments, Z comprises double-stranded DNA. In some embodiments, the moieties of Z are capable of intermolecularly binding another molecule or surface, e.g., to anchor a compound comprising Z to the molecule or surface.

In certain embodiments, the compound of Formula (II) is of Formula (IIa):

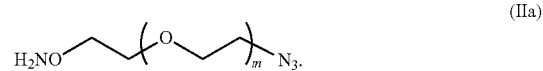

(IIa)

In certain embodiments, Formula (III) is of Formula (IIIa):

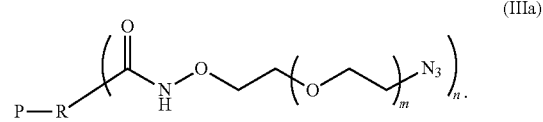

(IIIa)

In certain embodiments, n is 1. In certain embodiments, n is 2. In certain embodiments, m is 1. In certain embodiments, m is 5.

Figure 18A:
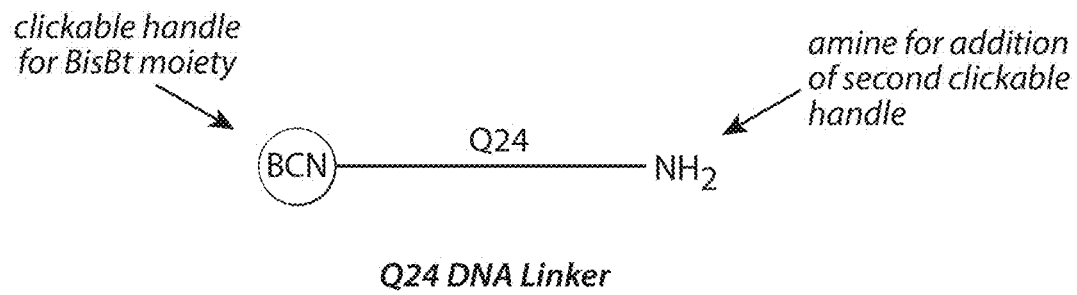
FIG. 18A-B show schemes for a Q24 DNA linker (FIG. 18A) and a full Peptide-DNA-SV conjugate (FIG. 18B). The five-membered triazole moieties shown in FIG. 18B represent any triazole moiety, such as those derived from unsubstituted, substituted, or cyclic alkyne moieties.
Figure 18B:
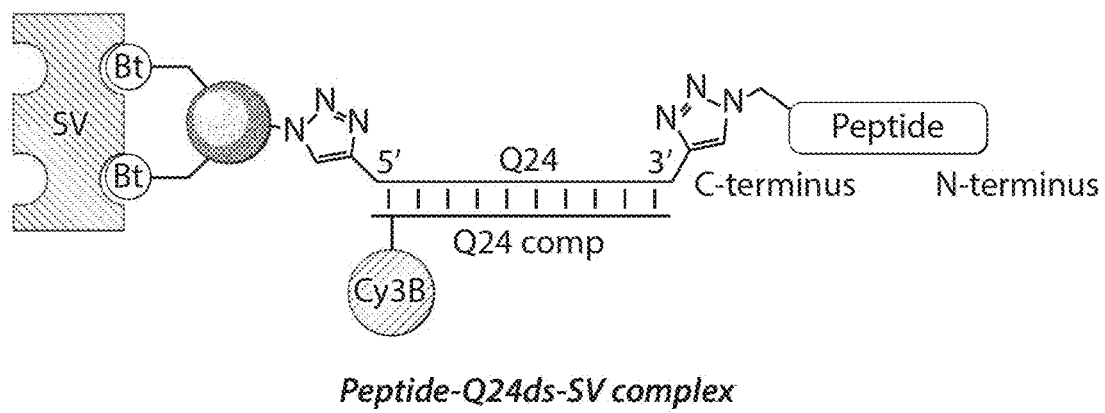
Figure 20:
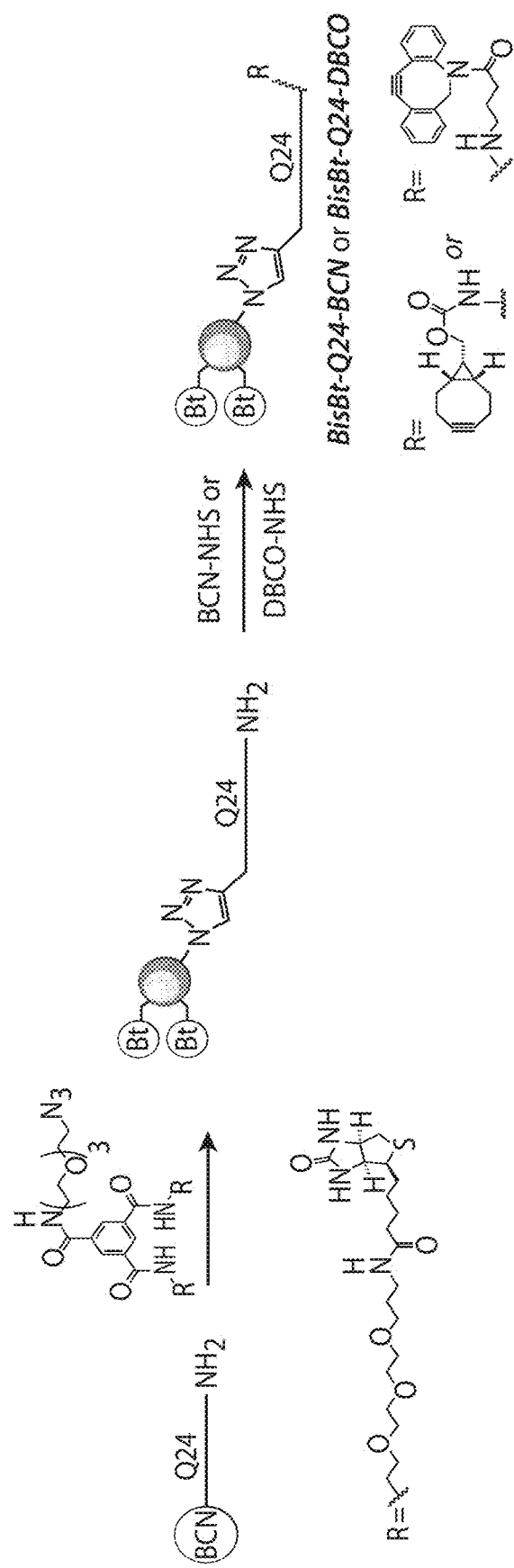
FIG. 20 shows a synthesis scheme for the completion of the Q24-BisBt-BCN or Q24-BisBt-DBCO DNA linkers.

In certain embodiments, Formula (IV) comprises TCO, and single-stranded DNA. In certain embodiments, Formula (IV) further comprises biotin (e.g., bisbiotin). In certain embodiments, Formula (IV) is Q24-BisBt-BCN. In certain embodiments, Formula (IV) is Q24-BisBt-DBCO. In certain embodiments, Formula (IV) is Q24-BisBt-TCO. Generally, Formula (IV) may comprise a branching moiety (e.g., a 1, 3, 5-tricarboxylate moiety), wherein two branches are direct or indirect attachments to biotin moieties, and the third branch is an attachment to the water soluble moiety (e.g., a polynucleotide such as Q24). As shown in FIG. 18B and FIG. 20, in certain embodiments Formula (IV) comprises a triazole moiety derived from the click-coupling of fragments comprising (i) a bisbiotin-azide functionalized linker and (ii) an alkyne (e.g., BCN)-functionalized polynucleotide (e.g.

Q24). The click-coupled product may be derivatived to introduce a further click handle $R_2$, such as BCN or DBCO.

In certain embodiments, Formula (V) is of Formula (Va):

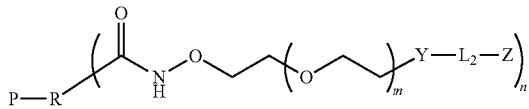
(Va)

wherein m, n is 1 or 2; and $L_2$, Y, and Z are as defined above. In certain particular embodiments, n is 1. In certain particular embodiments, n is 2. In certain particular embodiments, m is 1. In certain particular embodiments, m is 5. In certain particular embodiments, $L_2$ is absent. In certain embodiments, Y comprises a moiety selected from 1,2,3-triazolyl, 4,5-dihydro-1,2,3-triazolyl, isoxazolyl, 4,5-dihydroisoxazolyl, and 1,4-dihydropyridazyl. In certain embodiments, Z comprises single-stranded DNA. In certain embodiments, Z comprises double-stranded DNA. In certain embodiments, Z comprises biotin (e.g., bisbiotin). In certain embodiments, Z further comprises streptavidin.

In certain embodiments, the reaction of step (a) is performed in the presence of a carbodiimide reagent. In certain embodiments, the carbodiimide reagent is water soluble. In a particular embodiment, the carbodiimide reagent is 1-Ethyl-3-(3-dimethylaminopropyl)carbodiimide (EDC). In certain embodiments, the reaction of step (a) is performed at a pH in the range of 3-5. In certain embodiments (e.g., when to total peptide concentration below 1 mM), the concentration of EDC is about 10 mM and the concentration of the compound of Formula (II) is about 20 mM. In certain embodiments (e.g., in connection with Trypsin/LysC digestion, as described below) the concentration of the compound of Formula (II) is about may be about 50 mM and the concentration of EDC may be about 25 mM to suppress C-terminal intramolecular cyclization.

In certain embodiments of step (a), the plurality of compounds of Formula (III) 15 enriched prior to step (b), for example, by passing the compounds through a G10 sephadex column and/or passing the compounds through a C18 resin column. The use of C18 resin-based enrichment is particularly useful when the compound of Formula (II) is greater than about 200 g/mol. When G-10 sephadex is used in the enrichment, the elution buffer may be 0.5×PBS (pH 7.0). When C18 resin is used in the enrichment, the elution buffer may be 0.1% formic acid with 80% acetonitrile in water. The C18 eluent may be dried and the residue resuspended in 0.5×PBS prior to step (b).

In certain embodiments of step (b), the click reaction between the plurality of compounds of Formula (III) and the compound of Formula (IV) is uncatalyzed. In certain embodiments, the click reaction is catalyzed, for example, using a copper salt (e.g., a $Cu^+$ salt, or a $Cu^{2+}$ salt that is reduced in situ to a $Cu^+$ salt). Suitable $Cu^{2+}$ salts include $CuSO_4$. In certain embodiments, the reaction of step (b) comprises heating the reaction mixture.

In certain embodiments, the compound of Formula (IV) is added to the plurality of compounds of Formula (III). In certain embodiments, the total concentration of the compound of Formula (IV) and the plurality of compounds of Formula (III) is maintained in the range between 10 μM to 1 mM.

In certain embodiments of step (b), when Z comprises single-stranded DNA, the method further comprises hybridizing a complementary DNA strand to the single-stranded DNA to obtain a compound wherein Z comprises double-stranded DNA. In certain embodiments, the single-stranded DNA is Q24 and the complementary DNA strand is a Cy3B-labeled Q24 complementary strand.

In certain embodiments of step (b), when Z comprises biotin (e.g., bisbiotin), the method further comprises contacting the biotin (e.g., bisbiotin) with streptavidin to obtain a compound wherein Z comprises biotin (e.g., bisbiotin) and streptavidin.

In certain embodiments, the plurality of peptides of Formula (I), or salts thereof, is obtained by subjecting a protein to enzymatic digestion to obtain a digestive mixture comprising the plurality of peptides of Formula (I), or salts thereof. In certain embodiments, the enzymatic digestion comprises cleaving the C-terminal bonds of aspartic acid and/or glutamic acid residues of the protein. In certain specific embodiments, the enzymatic digestion is Glu-C digestion.

In certain embodiments, the total concentration of the plurality of peptides of Formula (I), or salts thereof, after digestion of 20 μg protein is below 100 μM.

In certain embodiments, the enzymatic digestion is performed in phosphate buffer (pH 7.8) or ammonium bicarbonate buffer (pH 4.0).

In certain embodiments, the enzymatic digestion comprises cleaving the C-terminal bonds of lysine and/or arginine residues of the protein. In certain specific embodiments, the enzymatic digestion is Trypsin+Lys-C digestion.

In certain embodiments, the carboxylic acid moieties of the protein, if present, are protected prior to the enzymatic digestion. For example, the carboxylic acid moieties of the protein, if present, may be esterified prior to enzymatic digestion. In certain specific embodiments, the esterified carboxylic acids are methyl esters.

In certain embodiments, the sulfide moieties of the protein are protected prior to enzymatic digestion. In certain specific embodiments, the sulfide moieties are protected by exposing the protein to tris(carboxyethyl)phosphine (TCEP) and iodoacetamide (ICM), or maleimide.

In certain particular embodiments, TCEP is present in the form of a hydrochloride salt, i.e., TCEP.HCl.

In certain embodiments, the method further comprises the step of enriching the digestive mixture prior to step (a).

C-Terminal Amine Functionalization

In another aspect, the present disclosure provides a method of selective C-terminal amine functionalization of a peptide, comprising:

a. reacting a plurality of peptides of Formula (VI):

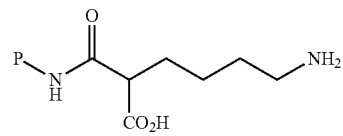
(VI)

or salts thereof, with a compound of Formula (VII):

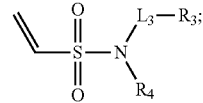
(VII)

to obtain a plurality of compounds of Formula (VIII):

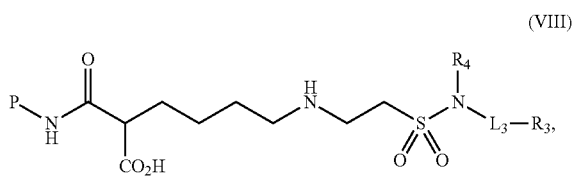
(VIII)

or salts thereof; and b. reacting the plurality of compounds of Formula (VIII), or salts thereof, with a compound of Formula (IX):

(IX)

to afford a plurality of compounds of Formula (X):

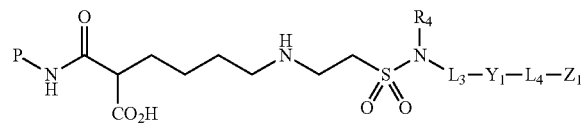
(X)

or salts thereof; wherein P, $L_3$, $L_4$, $R_3$, $R_4$, $Y_1$, and $Z_1$ are as defined below.

Each P independently is a peptide. In certain embodiments, P has 2-100 amino acid residues. In certain embodiments, P has 2-30 amino acid residues.

$L_3$ is a linker. In certain embodiments, $L_3$ is a substituted or unsubstituted aliphatic chain, wherein one or more carbon atoms are optionally, independently replaced by a heteroatom, an aryl, heteroaryl, cycloalkyl, or heterocyclyl moiety. In certain embodiments, $L_3$ is polyethylene glycol (PEG). In other embodiments, $L_3$ is a peptide, or an oligonucleotide.

$L_4$ is a linker, or is absent. In certain embodiments, $L_4$ is absent. In certain embodiments, $L_4$ is a substituted or unsubstituted aliphatic chain, wherein one or more carbon atoms are optionally, independently replaced by a heteroatom, an aryl, heteroaryl, cycloalkyl, or heterocyclyl moiety. In certain embodiments, $L_4$ is polyethylene glycol (PEG). In other embodiments, $L_4$ is a peptide, or an oligonucleotide.

$R_3$ is a moiety comprising a click chemistry handle. In certain embodiments, $R_3$ is a moiety comprising an azide, tetrazine, nitrile oxide, alkyne or strained alkene. In certain embodiments, the alkyne is a primary alkyne. In certain embodiments, the alkyne is a cyclic (e.g., mono- or polycyclic) alkyne (e.g., diarylcyclooctyne, or bicycle[6.1.0]nonyne). In certain embodiments, the strained alkene is trans-cyclooctene. In certain embodiments, $R_1$ is a moiety comprising an azide. In certain embodiments, the tetrazine comprises the structure:

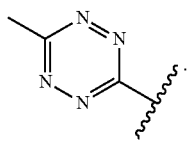 [SMILES: *c1nnc(C)nn1]

$R_4$ is substituted or unsubstituted aryl or substituted or unsubstituted heteroaryl. In certain embodiments, $R_4$ is substituted or unsubstituted phenyl. In certain particular embodiments, $R_4$ is phenyl. In certain particular embodiments, $R_4$ is 4-nitrophenyl.

$R_5$ is a moiety comprising a click chemistry handle that is complementary to $R_3$. The click chemistry handle of $R_5$ is capable of undergoing a click reaction (i.e., an electrocyclic reaction to form a 5-membered heterocyclic ring) with $R_3$. For example, when $R_3$ comprises an azide, nitrile oxide, or a tetrazine, then $R_5$ may comprise an alkyne or a strained alkene. Conversely, when $R_3$ comprises an alkyne or a strained alkene, then $R_5$ may comprise an azide, nitrile oxide, or tetrazine. In certain embodiments, $R_5$ is a moiety comprising an azide, tetrazine, nitrile oxide, alkyne or strained alkene. In certain embodiments, the alkyne is a primary alkyne. In certain embodiments, the alkyne is a cyclic (e.g., mono- or polycyclic) alkyne (e.g., diarylcyclooctyne, or bicycle[6.1.0]nonyne). In certain particular embodiments, $R_5$ comprises BCN. In other particular embodiments, $R_5$ comprises DBCO. In certain embodiments, the strained alkene is trans-cyclooctene. In certain embodiments, the tetrazine comprises the structure:

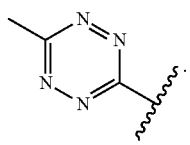 [SMILES: *c1nnc(C)nn1]

$Y_1$ is a moiety resulting from the click reaction of $R_3$ and $R_5$. $Y_1$ is a 5-membered heterocyclic ring resulting from an electrocyclic reaction (e.g., 3+2 cycloaddition, or 4+2 cycloaddition) between the reactive click chemistry handles of $R_3$ and $R_5$. In certain embodiments, $Y_1$ is a diradical comprising a 1,2,3-triazolyl, 4,5-dihydro-1,2,3-triazolyl, isoxazolyl, 4,5-dihydroisoxazolyl, or 1,4-dihydropyridazyl moiety.

$Z_1$ is a water-soluble moiety. In certain embodiments, $Z_1$ imparts water-solubility to the compound to which it is attached. In certain embodiments, $Z_1$ comprises polyethylene glycol (PEG). In certain embodiments, $Z_1$ comprises single-stranded DNA. In certain particular embodiments, $Z_1$ comprises Q24. In certain embodiments, $Z_1$ comprises single-stranded DNA. In certain embodiments (e.g., compounds of Formula (V)), $Z_1$ further comprises biotin (e.g., bisbiotin). When $Z_1$ comprises biotin (e.g., bisbiotin), $Z_1$ may further comprise streptavidin. In certain embodiments, $Z_1$ comprises double-stranded DNA. In some embodiments, the moieties of $Z_1$ are capable of intermolecularly binding another molecule or surface, e.g., to anchor a compound comprising $Z_1$ to the molecule or surface.

In certain embodiments, the compound of Formula (VII) is selected from:

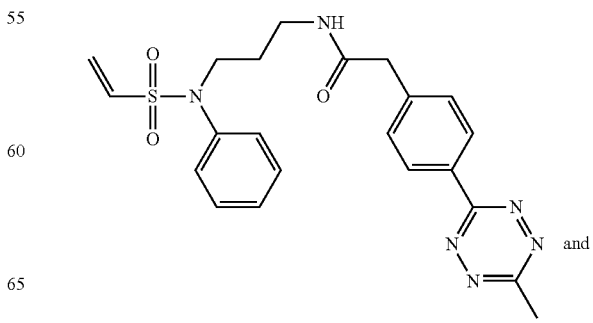

and

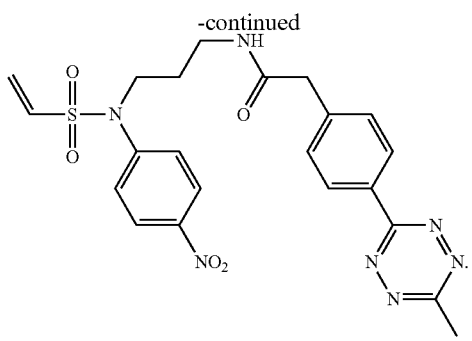

In certain embodiments, Formula (VIII) is of Formula (VIIIa) or Formula (VIIIb)

(a) is performed in pH 9.5 buffer/acetonitrile (1:3 v/v) at approximately 37° C. In certain embodiments, the reaction of step (a) is performed using a concentration of the compound of Formula (VII) of about 500 mM.

In certain embodiments, the plurality of compounds of Formula (VIII) is enriched prior to step (b). In certain embodiments, the enrichment comprises ethyl acetate/hexane extraction. Suitable ranges for ethyl acetate/hexane include, but are not limited to, 20 to 100 volume % ethyl acetate in hexanes. In certain embodiments, the volume of organic solvent used in the extraction is about 10× the volume of aqueous layer. Other water immiscible organic solvents can be used in the extraction, e.g., diethyl ether, dichloromethane, chloroform, benzene, toluene, and n-1-butanol.

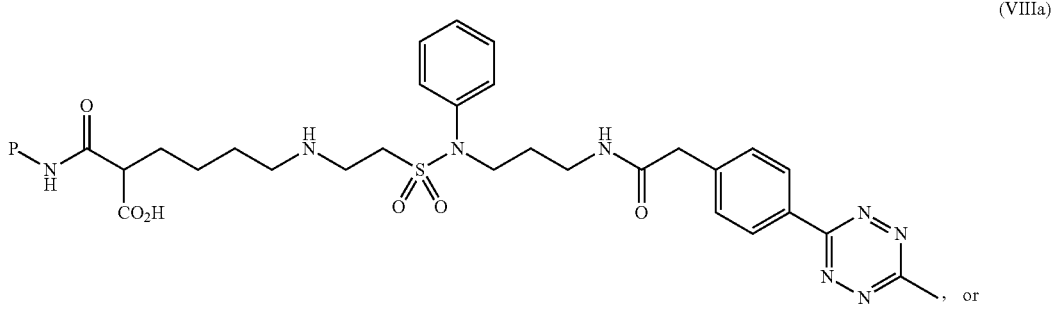

(VIIIa)

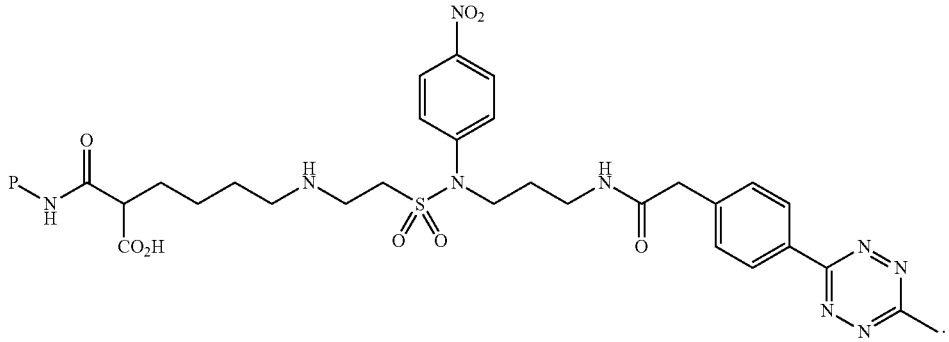

(VIIIb)

In certain embodiments, Formula (IX) comprises TCO, single-stranded DNA, and biotin (e.g., bisbiotin). In certain embodiments, Formula (IX) is Q24-BisBt-BCN. In certain embodiments, Formula (IX) is Q24-BisBt-DBCO. In certain embodiments, Formula (IX) is Q24-BisBt-TCO. Generally, Formula (IX) may comprise a branching moiety (e.g., a 1, 3, 5-tricarboxylate moiety), wherein two branches are direct or indirect attachments to biotin moieties, and the third branch is an attachment to the water soluble moiety (e.g., a polynucleotide such as Q24). As shown in FIG. 18B and FIG. 20, in certain embodiments Formula (IX) comprises a triazole moiety derived from the click-coupling of fragments comprising (i) a bisbiotin-azide functionalized linker and (ii) an alkyne (e.g., BCN)-functionalized polynucleotide (e.g. Q24). The click-coupled product may be derivatized to introduce a further click handle $R_5$, such as BCN or DBCO.

In certain embodiments, the reaction of step (a) is performed in the presence of a buffer having a concentration in the range of about 20 mM-500 mM and a pH in the range of about 9-11, and acetonitrile in the range of about 20-70% of total volume. In certain embodiments, the reaction of step In certain embodiments, the reaction of step (b) comprises reacting the compounds of Formula (VIII) with about one equivalent of the compound of Formula (IX). In certain embodiments, the reaction of step (b) comprises heating the reaction mixture.

In certain embodiments of step (b), when $Z_1$ comprises single-stranded DNA, the method further comprises hybridizing a complementary DNA strand to the single-stranded DNA to obtain a compound wherein $Z_1$ comprises double-stranded DNA. In certain embodiments, the single-stranded DNA is Q24 and the complementary DNA strand is a Cy3B-labeled Q24 complementary strand.

In certain embodiments of step (b), when $Z_1$ comprises biotin (e.g., bisbiotin), the method further comprises contacting the biotin (e.g., bisbiotin) with streptavidin to obtain a compound wherein $Z_1$ comprises biotin (e.g., bisbiotin) and streptavidin.

In certain embodiments, the plurality of peptides of Formula (VI), or salts thereof, is obtained by subjecting a protein to enzymatic digestion to obtain a digestive mixture comprising the plurality of peptides of Formula (VI), or salts thereof. The enzymatic digestion comprises cleaving the C-terminal bonds of lysine and/or arginine residues of the protein. In certain embodiments, the enzymatic digestion is performed using Trypsin, Lys-C, or a combination thereof. In certain embodiments, the enzymatic digestion comprises reacting the protein with Trypsin and Lys-C in Tris-HCl buffer (pH 8.5). In certain embodiments, the total concentration of the plurality of peptides of Formula (VI), or salts thereof, after digestion of 20 µg protein is below 100 µM.

In certain embodiments, the enzymatic digestion comprises reacting the protein with Trypsin, wherein the molar ratio of Trypsin:protein is in the range of 1:50 to 1:200, inclusive.

In certain embodiments, the sulfide moieties of the protein are protected prior to enzymatic digestion. In certain specific embodiments, the sulfide moieties are protected by exposing the protein to tris(carboxyethyl)phosphine (TCEP) and iodoacetamide (ICM), or maleimide.

In certain embodiments, the method further comprises the step of enriching the digestive mixture prior to step (a). In certain embodiments, the digestive mixture is used in the method of selective C-terminal amine functionalization of a peptide without enrichment or purification.

Selective Amine Functionalization Via Diazo Transfer

In another aspect, the present disclosure provides a method of selective N-functionalization of a peptide, comprising reacting a plurality of peptides of Formula (XI):

(XI)

or salts thereof, wherein each P independently is a peptide having an N-terminal amine, with a compound of Formula (XII):

(XII)

under conditions (a), comprising $Cu^{2+}$, or a precursor thereof, and a buffer having a pH of about 7-8.5; to obtain a plurality of N-terminal azido compounds of Formula (XIIIa):

(XIIIa)

or salts thereof; or under conditions (b), comprising $Cu^{2+}$, or a precursor thereof, and a buffer having a pH of about 10-11; to obtain a plurality of ε-azido compounds of the Formula (XIIIb):

(XIIIb)

or salts thereof.

In some embodiments, the compound of Formula (XII) is present in the form of a salt. In certain particular embodiments, the compound of Formula (XII) is imidazole-1-sulfonyl azide tetrafluoroborate. In some embodiments, the compound of Formula (XII), or salt thereof, is present in the form of a solution. In certain embodiments, the solution comprises a base (e.g., potassium hydroxide).

Each P independently is a peptide having an N-terminal amine. In certain embodiments, P has 2-100 amino acid residues. In certain embodiments, P has 2-30 amino acid residues.

In certain embodiments, conditions (a) comprise suitable $Cu^{2+}$ salts, for example $CuSO_4$. In certain embodiments, conditions (a) comprise reaction at about 25° C. for about 30-60 minutes. In a particular embodiment, conditions (a) comprise reaction at ambient temperature (e.g., about 25° C.) for about 60 minutes.

In certain embodiments, the compound of Formula (XII) is replaced by an aryl/heteroaryl sulfonyl azide compound that is not larger than 500 Da. For example, the compound of Formula (XII) may be replaced with a compound of Formula (XIIa):

(XIIa)

wherein $R_A$ is substituted or unsubstituted aryl, or substituted or unsubstituted heteroaryl.

In certain embodiments, conditions (b) include comprise phosphate or bicarbonate buffer at pH 10.5. In certain embodiments, conditions (b) comprise suitable $Cu^{2+}$ salts, for example $CuSO_4$. In certain embodiments, conditions (b) comprise about 2.4 molar equivalents of $CuSO_4$ relative to the compound of Formula (XI). In certain conditions (b) comprise about 20 molar equivalents of the compound of Formula (XII) relative to the compound of Formula (XI). In certain embodiments, conditions (b) comprise reaction at about 25° C. In certain embodiments, conditions (b) comprise reaction for about 30-60 minutes. In a particular embodiment, conditions (b) comprise reaction at ambient temperature (e.g., about 25° C.) for about 60 minutes.

In some embodiments, the compound of Formula (XIIa) is present in the form of a solution. In certain embodiments, the solution comprises a base (e.g., potassium hydroxide).

In certain embodiments, the N-terminal:ε selectivity under conditions (b) is at least about 90%.

In certain embodiments, methods utilizing diazo transfer chemistry as described herein further comprise the step of quenching (i.e., neutralizing) unreacted sulfonyl azide reagent by addition of a material which neutralizes the sulfonyl azide reagent. In certain embodiments, the material is a resin or bead, e.g., a polystyrene polyamine bead. Advantageously, a resin or bead may be removed by filtration.

In some embodiments, the plurality of peptides of Formula (XI), or salts thereof, is obtained by subjecting a protein to enzymatic digestion to obtain a digestive mixture comprising the plurality of peptides of Formula (XI), or salts thereof. The enzymatic digestion comprises cleaving the C-terminal bonds of aspartic acid and/or glutamic acid residues of the protein.

In some embodiments, the enzymatic digestion is Trypsin+Lys-C digestion. In some embodiments, the Trypsin+Lys-C digestion comprises reacting the protein with Trypsin and Lys-C at room temperature in pH 9.5 buffer.

In some embodiments, the method further comprises enriching the plurality of compounds of Formula (XIIIb), or salts thereof.

In some embodiments, the method further comprises reacting the plurality of compounds of Formula (XIIIb) or salts thereof with a compound of Formula (XIV):

$R_6-L_5-Z_2$ (XIV)

wherein $R_6$ is a moiety comprising an alkyne or a strained alkene; $L_5$ is a linker or is absent; and $Z_2$ is a water-soluble moiety;

to obtain a plurality of compounds of Formula (XV), or salts thereof:

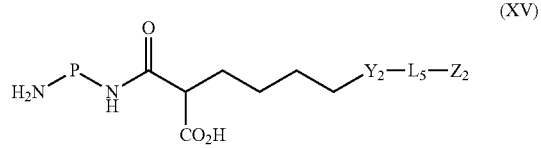

(XV)

wherein $Y_2$ is a moiety resulting from a click reaction with the azide moiety of Formula (XIIIb) and $R_6$.

$R_6$ is a moiety comprising a click chemistry handle that is complementary to the azide moiety of Formula (XIIIb) The click chemistry handle of $R_6$ is capable of undergoing a click reaction (i.e., an electrocyclic reaction to form a 5-membered heterocyclic ring) with the azide moiety of Formula (XIIIb) In certain embodiments, $R_6$ comprises an alkyne or a strained alkene. In certain embodiments, the alkyne is a primary alkyne. In certain embodiments, the alkyne is a cyclic (e.g., mono- or polycyclic) alkyne (e.g., diarylcyclooctyne, or bicycle[6.1.0]nonyne). In certain particular embodiments, $R_6$ comprises BCN. In other particular embodiments, $R_6$ comprises DBCO. In certain embodiments, the strained alkene is trans-cyclooctene.

In certain embodiments, $L_5$ is absent. In certain embodiments, $L_5$ is a substituted or unsubstituted aliphatic chain, wherein one or more carbon atoms are optionally replaced by a heteroatom, an aryl, heteroaryl, cycloalkyl, or heterocyclyl moiety. In certain embodiments, $L_5$ is polyethylene glycol (PEG). In other embodiments, $L_5$ is a peptide, or an oligonucleotide.

In certain embodiments, $Z_2$ comprises PEG. In certain embodiments, $Z_2$ comprises single-stranded DNA. In certain embodiments, $Z_2$ comprises double-stranded DNA. In certain embodiments, $Z_2$ further comprises biotin (e.g., bisbiotin). In certain embodiments, when $Z_2$ comprises single-stranded DNA, the method further comprises hybridizing a complementary DNA strand to the single-stranded DNA to obtain a compound wherein $Z_2$ comprises double-stranded DNA. In certain embodiments, the single-stranded DNA is Q24 and the complementary DNA strand is Cy3B.

In certain embodiments, the compound of Formula (XIV) comprises TCO, single-stranded DNA, and biotin (e.g., bisbiotin). In certain embodiments, Formula (XIV) is Q24-BisBt-BCN. In certain embodiments, Formula (XIV) is Q24-BisBt-DBCO. In certain embodiments, Formula (XIV) is Q24-BisBt-TCO. Generally, Formula (XIV) may comprise a branching moiety (e.g., a 1, 3, 5-tricarboxylate moiety), wherein two branches are direct or indirect attachments to biotin moieties, and the third branch is an attachment to the water soluble moiety (e.g., a polynucleotide such as Q24). As shown in FIG. 18B and FIG. 20, in certain embodiments Formula (XIV) comprises a triazole moiety derived from the click-coupling of fragments comprising (i) a bisbiotin-azide functionalized linker and (ii) an alkyne (e.g., BCN)-functionalized polynucleotide (e.g. Q24). The click-coupled product may be derivatived to introduce a further click handle $R_6$, such as BCN or DBCO.

In certain embodiments, the compound of Formula (XIV) comprises DBCO, single-stranded DNA, and streptavidin (SV). In certain particular embodiments, the compound of Formula (XIV) is DBCO-Q24-SV.

In certain embodiments, when $Z_2$ comprises biotin (e.g., bisbiotin), the method further comprises contacting the biotin (e.g., bisbiotin) with streptavidin to obtain a compound wherein $Z_2$ comprises biotin (e.g., bisbiotin) and streptavidin. In other embodiments, when $Z_2$ comprises streptavidin, the method further comprises contacting the streptavidin with biotin (e.g., bisbiotin) to obtain a compound wherein $Z_2$ comprises streptavidin and biotin (e.g., bisbiotin).

Click Chemistry

In certain embodiments, the reaction used to conjugate the host to the tag is a "click chemistry" reaction (e.g., the Huisgen alkyne-azide cycloaddition). It is to be understood that any "click chemistry" reaction known in the art can be used to this end. Click chemistry is a chemical approach introduced by Sharpless in 2001 and describes chemistry tailored to generate substances quickly and reliably by joining small units together. See, e.g., Kolb, Finn and Sharpless Angewandte Chemie International Edition (2001) 40: 2004-2021; Evans, Australian Journal of Chemistry (2007) 60: 384-395). Exemplary coupling reactions (some of which may be classified as "click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgen cycloaddition; thiol-yne addition; imine formation; Michael additions (e.g., maleimide addition); and Diels-Alder reactions (e.g., tetrazine [4+2] cycloaddition).

The term "click chemistry" refers to a chemical synthesis technique introduced by K. Barry Sharpless of The Scripps Research Institute, describing chemistry tailored to generate covalent bonds quickly and reliably by joining small units comprising reactive groups together. See, e.g., Kolb, Finn and Sharpless Angewandte Chemie International Edition (2001) 40: 2004-2021; Evans, Australian Journal of Chemistry (2007) 60: 384-395). Exemplary reactions include, but are not limited to, azide-alkyne Huisgen cycloaddition; and Diels-Alder reactions (e.g., tetrazine [4+2] cycloaddition). In some embodiments, click chemistry reactions are modular, wide in scope, give high chemical yields, generate inoffensive byproducts, are stereospecific, exhibit a large thermodynamic driving force >84 kJ/mol to favor a reaction with a single reaction product, and/or can be carried out under physiological conditions. In some embodiments, a click chemistry reaction exhibits high atom economy, can be carried out under simple reaction conditions, use readily available starting materials and reagents, uses no toxic solvents or use a solvent that is benign or easily removed (preferably water), and/or provides simple product isolation by non-chromatographic methods (crystallization or distillation).

The term "click chemistry handle," as used herein, refers to a reactant, or a reactive group, that can partake in a click chemistry reaction. For example, a strained alkyne, e.g., a cyclooctyne, is a click chemistry handle, since it can partake in a strain-promoted cycloaddition (see, e.g., Table 1). In general, click chemistry reactions require at least two molecules comprising click chemistry handles that can react with each other. Such click chemistry handle pairs that are reactive with each other are sometimes referred to herein as partner click chemistry handles. For example, an azide is a partner click chemistry handle to a cyclooctyne or any other alkyne. Exemplary click chemistry handles suitable for use according to some aspects of this invention are described herein, for example, in Tables 1 and 2. Other suitable click chemistry handles are known to those of skill in the art.

TABLE 1

Exemplary click chemistry handles and reactions.

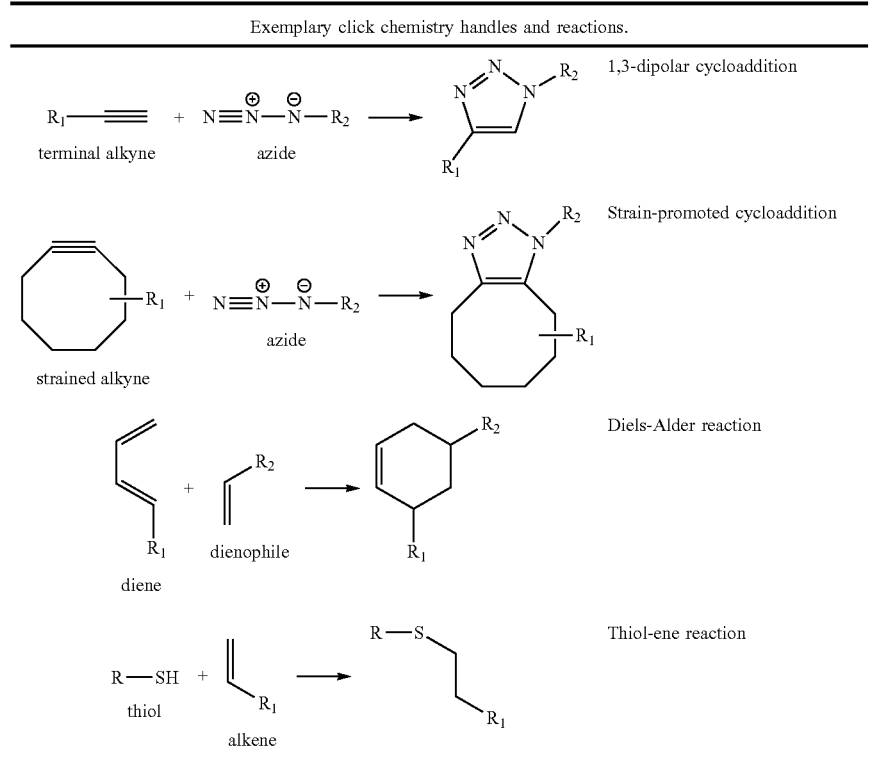

In some embodiments, click chemistry handles are used that can react to form covalent bonds in the presence of a metal catalyst, e.g., copper (II). In some embodiments, click chemistry handles are used that can react to form covalent bonds in the absence of a metal catalyst. Such click chemistry handles are well known to those of skill in the art and include the click chemistry handles described in Becer, Hoogenboom, and Schubert, *Click Chemistry beyond Metal-Catalyzed Cycloaddition*, Angewandte Chemie International Edition (2009) 48: 4900-4908.

TABLE 2

Exemplary click chemistry handles and reactions.

| | Reagent A | Reagent E | Mechanism | Notes, on reaction[a] | Reference |
|---|---|---|---|---|---|
| 0 | azide | alkyne | Cu-catalyzed [3 + 2] azide-alkyne cycloaddition (CuAAC) | 2 h at 60° C. in $H_2O$ | [9] |
| 1 | azide | cycloectyne | strain-promoted [3 + 2] azide-alkyne cycloaddition (SPAAC) | 1 h at RT | [6-8, 10, 11] |
| 2 | azide | activated alkyne | [3 + 2] Huisgen cycloaddition | 4 h at 50° C. | [12] |
| 3 | azide | electron-deficient alkyne | [3 + 2] cycloaddition | 12 h. at RT in $H_2O$ | [13] |

TABLE 2-continued

Exemplary click chemistry handles and reactions.

| | Reagent A | Reagent E | Mechanism | Notes, on reaction[a] | Reference |
|---|---|---|---|---|---|
| 4 | azide | aryne | [3 + 2] cycloaddition | 4 h at RT in THF with crown ether or 24 h at RT in $CH_2CN$ | [14, 15] |
| 5 | tetrazine | alkene | Diels-Alder retro-[4 + 2] cycloaddition | 40 min at 25° C. (100% yield) $N_2$ is the only by-product | [36-38] |
| 6 | tetrazole | alkene | 1,3-dipolar cycloaddition (photoclick) | few min UV irradiation and then overnight at 4° C. | [39, 40] |
| 7 | dithioester | diene | hetero-Diels-Alder cycloaddition | 10 min at RT | [43] |
| 8 | anthracene | maleimide | [4 + 2] Diesl-Alder reaction | 2. days at reflux in toluene | [41] |
| 9 | thiol | alkene | radical addition (thio click) | 30 min UV (quantiative conv.) or 24 h UV irradiation (>96%) | [19-23] |
| 10 | thiol | enone | Michael addition | 24 h at RT in $CH_2CN$ | [27] |
| 11 | thiol | maleimide | Michael addition | 1 h at 40° C. in THF or 16 h at RT in dioxane | [24-26] |
| 12 | thiol | para-fluoro | nucleophilic substitution | overnight at RT in DMF or 60 min at 40° C. in DMF | [32] |
| 13 | amine | para-fluoro | nucleophilic substitution | 20 min MW at 95° C. in NMP as solvent | [30] |

[a]RT = room temperature, DMF = N,N-dimethylformamide, NMP = N-methylpyrolidone, THF = tetrahydrofuran, $CH_2CN$ = acetonitrile.

From Becer, Hoogenboom, and Schubert, *Click Chemistry Beyond Metal-Catalyzed Cycloaddition, Angewandte Chemie International Edition* (2009) 48: 4900-4908.

Additional click chemistry handles suitable for use in methods of conjugation described herein are well known to those of skill in the art, and such click chemistry handles include, but are not limited to, the click chemistry reaction partners, groups, and handles described in PCT/US2012/044584 and references therein, which references are incorporated herein by reference for click chemistry handles and methodology.

Compounds

In certain aspects, the present disclosure provides compounds of Formulae (II), (IIa), (III), (IIIa), (IV), (V), (Va), (VII), (VIII), (VIIIa), (VIIIb), (XIV), (X), (XI), (XII), (XIIIa), (XIIIb), (XV), and salts thereof, as described herein in various embodiments.

In certain embodiments, the compounds are water soluble.

In certain embodiments, the compounds are useful for applications relating to the analysis of proteins and peptides, such as peptide sequencing. For example, in certain embodiments, compounds of Formulae (V), (X), (XV), and salts thereof, may be covalently or non-covalently attached to a surface.

Peptide Surface Immobilization

In certain single molecule analytical methods, a molecule to be analyzed is immobilized onto surfaces such that the molecule may be monitored without interference from other reaction components in solution. In some embodiments, surface immobilization of the molecule allows the molecule to be confined to a desired region of a surface for real-time monitoring of a reaction involving the molecule.

Accordingly, in some aspects, the application provides methods of immobilizing a peptide to a surface by attaching any one of the compounds described herein to a surface of a solid support. In some embodiments, the methods comprise contacting a compound of Formula (V), (X), (XV), or a salt thereof, to a surface of a solid support. In some embodiments, the surface is functionalized with a complementary functional moiety configured for attachment (e.g., covalent or non-covalent attachment) to a functionalized terminal end of a peptide. In some embodiments, the solid support comprises a plurality of sample wells formed at the surface of the solid support. In some embodiments, the methods comprise immobilizing a single peptide to a surface of each of a plurality of sample wells. In some embodiments, confining a single peptide per sample well is advantageous for single molecule detection methods, e.g., single molecule peptide sequencing.

As used herein, in some embodiments, a surface refers to a surface of a substrate or solid support. In some embodiments, a solid support refers to a material, layer, or other structure having a surface, such as a receiving surface, that is capable of supporting a deposited material, such as a functionalized peptide described herein. In some embodiments, a receiving surface of a substrate may optionally have one or more features, including nanoscale or microscale recessed features such as an array of sample wells. In some embodiments, an array is a planar arrangement of elements such as sensors or sample wells. An array may be one or two dimensional. A one dimensional array is an array having one column or row of elements in the first dimension and a plurality of columns or rows in the second dimension. The number of columns or rows in the first and second dimensions may or may not be the same. In some embodiments, the array may include, for example, $10^2$, $10^3$, $10^4$, $10^5$, $10^6$, or $10^7$ sample wells.

Figure 9:
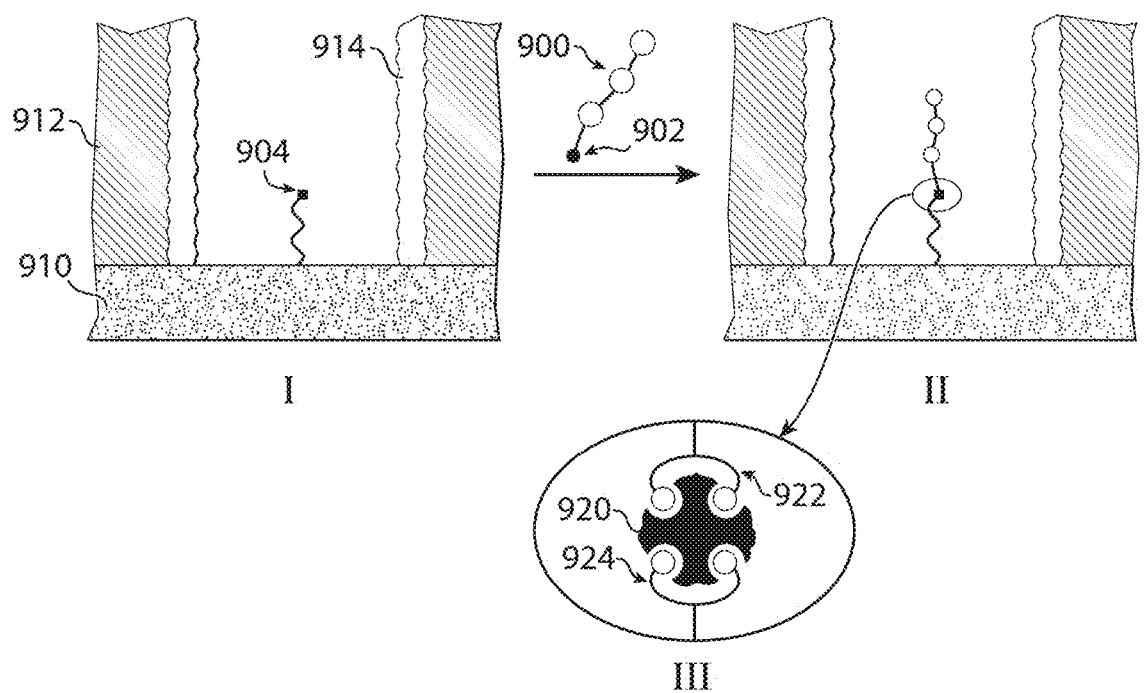
FIG. 9 shows a representative example of peptide surface immobilization.

An example scheme of peptide surface immobilization is depicted in FIG. 9. As shown, panels (I)-(II) depict a process of immobilizing a peptide 900 that comprises a functionalized terminal end 902. In panel (I), a solid support comprising a sample well is shown. In some embodiments, the sample well is formed by a bottom surface comprising a non-metallic layer 910 and side wall surfaces comprising a metallic layer 912. In some embodiments, non-metallic layer 910 comprises a transparent layer (e.g., glass, silica). In some embodiments, metallic layer 912 comprises a metal oxide surface (e.g., titanium dioxide). In some embodiments, metallic layer 912 comprises a passivation coating 914 (e.g., a phosphorus-containing layer, such as an organophosphonate layer). As shown, the bottom surface comprising non-metallic layer 910 comprises a complementary functional moiety 904. Methods of selective surface modification and functionalization are described in further detail in U.S. Patent Publication No. 2018/0326412 and U.S. Provisional Application No. 62/914,356, the contents of each of which are hereby incorporated by reference.

In some embodiments, peptide 900 comprising functionalized terminal end 902 is contacted with complementary functional moiety 904 of the solid support to form a covalent or non-covalent linkage group. In some embodiments, functionalized terminal end 902 and complementary functional moiety 904 comprise partner click chemistry handles, e.g., which form a covalent linkage group between peptide 900 and the solid support. Suitable click chemistry handles are described elsewhere herein. In some embodiments, functionalized terminal end 902 and complementary functional moiety 904 comprise non-covalent binding partners, e.g., which form a non-covalent linkage group between peptide 900 and the solid support. Examples of non-covalent binding partners include complementary oligonucleotide strands (e.g., complementary nucleic acid strands, including DNA, RNA, and variants thereof), protein-protein binding partners (e.g., barnase and barstar), and protein-ligand binding partners (e.g., biotin and streptavidin).

In panel (II), peptide 900 is shown immobilized to the bottom surface through a linkage group formed by contacting functionalized terminal end 902 and complementary functional moiety 904. In this example, peptide 900 is attached through a non-covalent linkage group, which is depicted in the zoomed region of panel (III). As shown, in some embodiments, the non-covalent linkage group comprises an avidin protein 920. Avidin proteins are biotin-binding proteins, generally having a biotin binding site at each of four subunits of the avidin protein. Avidin proteins include, for example, avidin, streptavidin, traptavidin, tamavidin, bradavidin, xenavidin, and homologs and variants thereof. In some embodiments, avidin protein 920 is streptavidin. The multivalency of avidin protein 920 can allow for various linkage configurations, as each of the four binding sites are independently capable of binding a biotin molecule (shown as white circles).

As shown in panel (III), in some embodiments, the non-covalent linkage is formed by avidin protein 920 bound to a first bis-biotin moiety 922 and a second bis-biotin moiety 924. In some embodiments, functionalized terminal end 902 comprises first bis-biotin moiety 922, and complementary functional moiety 904 comprises second bis-biotin moiety 924. In some embodiments, functionalized terminal end 902 comprises avidin protein 920 prior to being contacted with complementary functional moiety 904. In some embodiments, complementary functional moiety 904 comprises avidin protein 920 prior to being contacted with functionalized terminal end 902.

In some embodiments, functionalized terminal end 902 comprises first bis-biotin moiety 922 and a water-soluble moiety, where the water-soluble moiety forms a linkage between first bis-biotin moiety 922 and an amino acid (e.g., a terminal amino acid) of peptide 900. Water-soluble moieties are described in detail elsewhere herein.

Peptide Sequencing

In some embodiments, the compounds described herein may be subjected to peptide sequencing (also referred to as "polypeptide sequencing") by detecting single molecule binding interactions during a peptide degradation process. In some embodiments, the peptide being degraded is a compound of Formula (V), (X), (XV), or a salt thereof, that is covalently or non-covalently attached to a surface.

As used herein, sequencing a polypeptide refers to determining sequence information for a polypeptide. In some embodiments, this can involve determining the identity of each sequential amino acid for a portion (or all) of the polypeptide. However, in some embodiments, this can involve assessing the identity of a subset of amino acids within the polypeptide (e.g., and determining the relative position of one or more amino acid types without determining the identity of each amino acid in the polypeptide). In some embodiments, amino acid content information can be obtained from a polypeptide without directly determining the relative position of different types of amino acids in the polypeptide. The amino acid content alone may be used to infer the identity of the polypeptide that is present (e.g., by comparing the amino acid content to a database of polypeptide information and determining which polypeptide(s) have the same amino acid content).

In some aspects, peptide sequencing of the compounds of the disclosure may be performed by identifying one or more types of amino acids of a polypeptide. In some embodiments, one or more amino acids (e.g., terminal amino acids and/or internal amino acids) of the polypeptide are labeled (e.g., directly or indirectly, for example using a binding agent such as an amino acid recognition molecule) and the relative positions of the labeled amino acids in the polypeptide are determined. In some embodiments, the relative positions of amino acids in a polypeptide are determined using a series of amino acid labeling and cleavage steps. However, in some embodiments, the relative position of labeled amino acids in a polypeptide can be determined without removing amino acids from the polypeptide but by translocating a labeled polypeptide through a pore (e.g., a protein channel) and detecting a signal (e.g., a FRET signal) from the labeled amino acid(s) during translocation through the pore in order to determine the relative position of the labeled amino acids in the polypeptide molecule.

In some embodiments, the identity of a terminal amino acid (e.g., an N-terminal or a C-terminal amino acid) is assessed after which the terminal amino acid is removed and the identity of the next amino acid at the terminus is assessed, and this process is repeated until a plurality of successive amino acids in the polypeptide are assessed. In some embodiments, assessing the identity of an amino acid comprises determining the type of amino acid that is present. In some embodiments, determining the type of amino acid comprises determining the actual amino acid identity, for example by determining which of the naturally-occurring 20 amino acids is the terminal amino acid is (e.g., using a binding agent that is specific for an individual terminal amino acid). In some embodiments, the type of amino acid is selected from alanine, arginine, asparagine, aspartic acid, cysteine, glutamine, glutamic acid, glycine, histidine, isoleucine, leucine, lysine, methionine, phenylalanine, proline, selenocysteine, serine, threonine, tryptophan, tyrosine, and valine.

However, in some embodiments assessing the identity of a terminal amino acid type can comprise determining a subset of potential amino acids that can be present at the terminus of the polypeptide. In some embodiments, this can be accomplished by determining that an amino acid is not one or more specific amino acids (and therefore could be any of the other amino acids). In some embodiments, this can be accomplished by determining which of a specified subset of amino acids (e.g., based on size, charge, hydrophobicity, post-translational modification, binding properties) could be at the terminus of the polypeptide (e.g., using a binding agent that binds to a specified subset of two or more terminal amino acids). In some embodiments, assessing the identity of a terminal amino acid type comprises determining that an amino acid comprises a post-translational modification.

In some embodiments, a protein or polypeptide can be digested into a plurality of smaller polypeptides and sequence information can be obtained from one or more of these smaller polypeptides (e.g., using a method that involves sequentially assessing a terminal amino acid of a polypeptide and removing that amino acid to expose the next amino acid at the terminus). In some embodiments, methods of peptide sequencing may involve subjecting a polypeptide terminus to repeated cycles of terminal amino acid detection and terminal amino acid cleavage.

Figure 10A:
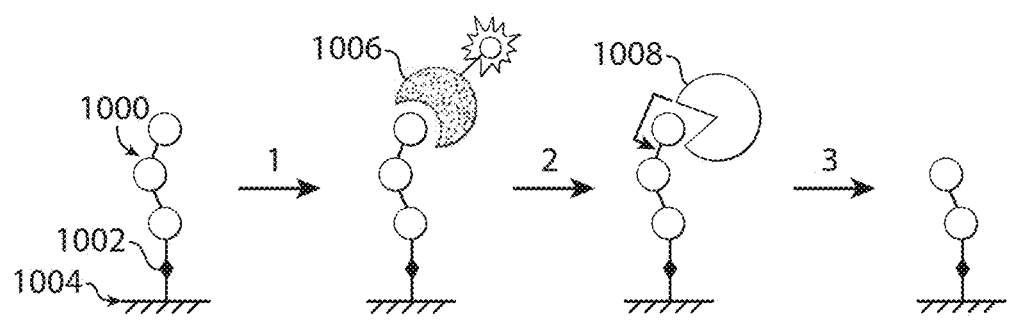
FIG. 10A-B show representative examples of peptide sequencing.

A non-limiting example of polypeptide sequencing by iterative terminal amino acid detection and cleavage is depicted in FIG. 10A. In some embodiments, polypeptide sequencing comprises providing a polypeptide 1000 that is immobilized to a surface 1004 of a solid support (e.g., attached to a bottom or sidewall surface of a sample well) through a linkage group 1002. In some embodiments, linkage group 1002 is formed by a covalent or non-covalent linkage between a functionalized terminal end of polypeptide 1000 and a complementary functional moiety of surface 1004. For example, in some embodiments, linkage group 1002 is formed by a non-covalent linkage between a biotin moiety of polypeptide 1000 (e.g., functionalized in accordance with the disclosure) and an avidin protein of surface 1004. In some embodiments, linkage group 1002 comprises a nucleic acid.

In some embodiments, polypeptide 1000 is immobilized to surface 1004 through a functionalization moiety at one terminal end such that the other terminal end is free for detecting and cleaving of a terminal amino acid in a sequencing reaction. Accordingly, in some embodiments, the reagents used in certain polypeptide sequencing reactions preferentially interact with terminal amino acids at the non-immobilized (e.g., free) terminus of polypeptide 1000. In this way, polypeptide 1000 remains immobilized over repeated cycles of detecting and cleaving. To this end, in some embodiments, linker 1002 may be designed according to a desired set of conditions used for detecting and cleaving, e.g., to limit detachment of polypeptide 1000 from surface 1004. Suitable linker compositions and techniques for functionalizing polypeptides (e.g., which may be used for immobilizing a polypeptide to a surface) are described in detail elsewhere herein.

In some embodiments, as shown in FIG. 10A, polypeptide sequencing can proceed by (1) contacting polypeptide 1000 with one or more amino acid recognition molecules that associate with one or more types of terminal amino acids. As shown, in some embodiments, a labeled amino acid recognition molecule 1006 interacts with polypeptide 1000 by associating with the terminal amino acid.

In some embodiments, the method further comprises identifying the amino acid (terminal or internal amino acid) of polypeptide 1000 by detecting labeled amino acid recognition molecule 1006. In some embodiments, detecting comprises detecting a luminescence from labeled amino acid recognition molecule 1006. In some embodiments, the luminescence is uniquely associated with labeled amino acid recognition molecule 1006, and the luminescence is thereby associated with the type of amino acid to which labeled amino acid recognition molecule 1006 selectively binds. As such, in some embodiments, the type of amino acid is identified by determining one or more luminescence properties of labeled amino acid recognition molecule 1006.

In some embodiments, polypeptide sequencing proceeds by (2) removing the terminal amino acid by contacting polypeptide 1000 with an exopeptidase 1008 that binds and cleaves the terminal amino acid of polypeptide 1000. Upon removal of the terminal amino acid by exopeptidase 1008, polypeptide sequencing proceeds by (3) subjecting polypeptide 1000 (having n−1 amino acids) to additional cycles of terminal amino acid recognition and cleavage. In some embodiments, steps (1) through (3) occur in the same reaction mixture, e.g., as in a dynamic peptide sequencing reaction. In some embodiments, steps (1) through (3) may be carried out using other methods known in the art, such as peptide sequencing by Edman degradation.

Edman degradation involves repeated cycles of modifying and cleaving the terminal amino acid of a polypeptide, wherein each successively cleaved amino acid is identified to determine an amino acid sequence of the polypeptide. Referring to FIG. 10A, peptide sequencing by conventional Edman degradation can be carried out by (1) contacting polypeptide 1000 with one or more amino acid recognition molecules that selectively bind one or more types of terminal amino acids. In some embodiments, step (1) further comprises removing any of the one or more labeled amino acid recognition molecules that do not selectively bind polypeptide 1000. In some embodiments, step (2) comprises modifying the terminal amino acid (e.g., the free terminal amino acid) of polypeptide 1000 by contacting the terminal amino acid with an isothiocyanate (e.g., PITC) to form an isothiocyanate-modified terminal amino acid. In some embodiments, an isothiocyanate-modified terminal amino acid is more susceptible to removal by a cleaving reagent (e.g., a chemical or enzymatic cleaving reagent) than an unmodified terminal amino acid.

In some embodiments, Edman degradation proceeds by (2) removing the terminal amino acid by contacting polypeptide 1000 with an exopeptidase 1008 that specifically binds and cleaves the isothiocyanate-modified terminal amino acid. In some embodiments, exopeptidase 1008 comprises a modified cysteine protease. In some embodiments, exopeptidase 1008 comprises a modified cysteine protease, such as a cysteine protease from *Trypanosoma cruzi* (see, e.g., Borgo, et al. (2015) *Protein Science* 24:571-579). In yet other embodiments, step (2) comprises removing the terminal amino acid by subjecting polypeptide 1000 to chemical (e.g., acidic, basic) conditions sufficient to cleave the isothiocyanate-modified terminal amino acid. In some embodiments, Edman degradation proceeds by (3) washing polypeptide 1000 following terminal amino acid cleavage. In some embodiments, washing comprises removing exopeptidase 1008. In some embodiments, washing comprises restoring polypeptide 1000 to neutral pH conditions (e.g., following chemical cleavage by acidic or basic conditions). In some embodiments, sequencing by Edman degradation comprises repeating steps (1) through (3) for a plurality of cycles.

In some embodiments, peptide sequencing can be carried out in a dynamic peptide sequencing reaction. In some embodiments, referring again to FIG. 10A, the reagents required to perform step (1) and step (2) are combined within a single reaction mixture. For example, in some embodiments, steps (1) and (2) can occur without exchanging one reaction mixture for another and without a washing step as in conventional Edman degradation. Thus, in this embodiments, a single reaction mixture comprises labeled amino acid recognition molecule 1006 and exopeptidase 1008. In some embodiments, exopeptidase 1008 is present in the mixture at a concentration that is less than that of labeled amino acid recognition molecule 1006. In some embodiments, exopeptidase 1008 binds polypeptide 1000 with a binding affinity that is less than that of labeled amino acid recognition molecule 1006.

Figure 10B:
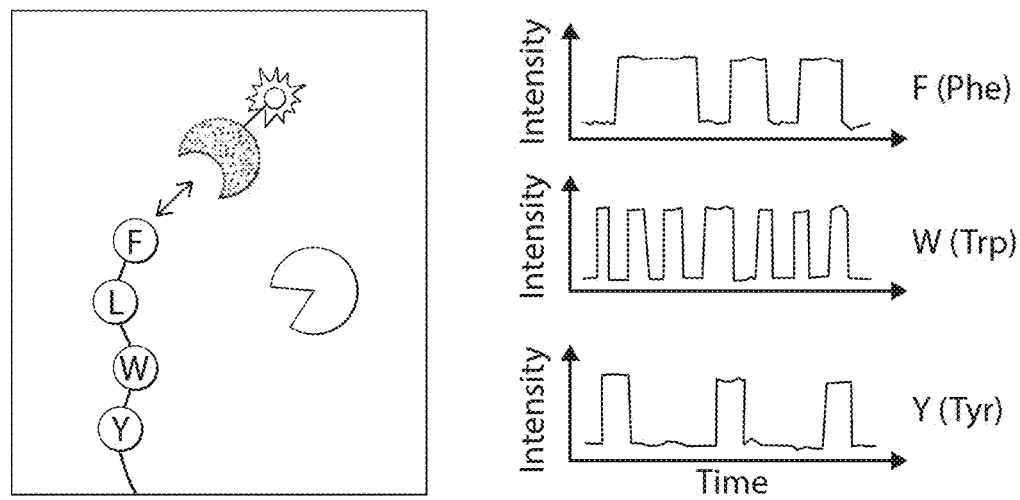

In some embodiments, dynamic polypeptide sequencing is carried out in real-time by evaluating binding interactions of terminal amino acids with labeled amino acid recognition molecules and a cleaving reagent (e.g., an exopeptidase). FIG. 10B shows an example of a method of sequencing in which discrete binding events give rise to signal pulses of a signal output. The inset panel (left) of FIG. 10B illustrates a general scheme of real-time sequencing by this approach. As shown, a labeled amino acid recognition molecule associates with (e.g., binds to) and dissociates from a terminal amino acid (shown here as phenylalanine), which gives rise to a series of pulses in signal output which may be used to identify the terminal amino acid. In some embodiments, the series of pulses provide a pulsing pattern (e.g., a characteristic pattern) which may be diagnostic of the identity of the corresponding terminal amino acid.

As further shown in the inset panel (left) of FIG. 10B, in some embodiments, a sequencing reaction mixture further comprises an exopeptidase. In some embodiments, the exopeptidase is present in the mixture at a concentration that is less than that of the labeled amino acid recognition molecule. In some embodiments, the exopeptidase displays broad specificity such that it cleaves most or all types of terminal amino acids. Accordingly, a dynamic sequencing approach can involve monitoring recognition molecule binding at a terminus of a polypeptide over the course of a degradation reaction catalyzed by exopeptidase cleavage activity.

FIG. 10B further shows the progress of signal output intensity over time (right panels). In some embodiments, terminal amino acid cleavage by exopeptidase(s) occurs with lower frequency than the binding pulses of a labeled amino acid recognition molecule. In this way, amino acids of a polypeptide may be counted and/or identified in a real-time sequencing process. In some embodiments, one type of amino acid recognition molecule can associate with more than one type of amino acid, where different characteristic patterns correspond to the association of one type of labeled amino acid recognition molecule with different types of terminal amino acids. For example, in some embodiments, different characteristic patterns (as illustrated by each of phenylalanine (F, Phe), tryptophan (W, Trp), and tyrosine (Y, Tyr)) correspond to the association of one type of labeled amino acid recognition molecule (e.g., ClpS protein) with different types of terminal amino acids over the course of degradation. In some embodiments, a plurality of labeled amino acid recognition molecules may be used, each capable of associating with different subsets of amino acids.

In some embodiments, dynamic peptide sequencing is performed by observing different association events, e.g., association events between an amino acid recognition molecule and an amino acid at a terminal end of a peptide, wherein each association event produces a change in magnitude of a signal, e.g., a luminescence signal, that persists for a duration of time. In some embodiments, observing different association events, e.g., association events between an amino acid recognition molecule and an amino acid at a terminal end of a peptide, can be performed during a peptide degradation process. In some embodiments, a transition from one characteristic signal pattern to another is indicative of amino acid cleavage (e.g., amino acid cleavage resulting from peptide degradation). In some embodiments, amino acid cleavage refers to the removal of at least one amino acid from a terminus of a polypeptide (e.g., the removal of at least one terminal amino acid from the polypeptide). In some embodiments, amino acid cleavage is determined by inference based on a time duration between characteristic signal patterns. In some embodiments, amino acid cleavage is determined by detecting a change in signal produced by association of a labeled cleaving reagent with an amino acid at the terminus of the polypeptide. As amino acids are sequentially cleaved from the terminus of the polypeptide during degradation, a series of changes in magnitude, or a series of signal pulses, is detected.

In some embodiments, signal pulse information may be used to identify an amino acid based on a characteristic pattern in a series of signal pulses. In some embodiments, a characteristic pattern comprises a plurality of signal pulses, each signal pulse comprising a pulse duration. In some embodiments, the plurality of signal pulses may be characterized by a summary statistic (e.g., mean, median, time decay constant) of the distribution of pulse durations in a characteristic pattern. In some embodiments, the mean pulse duration of a characteristic pattern is between about 1 millisecond and about 10 seconds (e.g., between about 1 ms and about 1 s, between about 1 ms and about 100 ms, between about 1 ms and about 10 ms, between about 10 ms and about 10 s, between about 100 ms and about 10 s, between about 1 s and about 10 s, between about 10 ms and about 100 ms, or between about 100 ms and about 500 ms). In some embodiments, different characteristic patterns corresponding to different types of amino acids in a single polypeptide may be distinguished from one another based on a statistically significant difference in the summary statistic. For example, in some embodiments, one characteristic pattern may be distinguishable from another characteristic pattern based on a difference in mean pulse duration of at least 10 milliseconds (e.g., between about 10 ms and about 10 s, between about 10 ms and about 1 s, between about 10 ms and about 100 ms, between about 100 ms and about 10 s, between about 1 s and about 10 s, or between about 100 ms and about 1 s). It should be appreciated that, in some embodiments, smaller differences in mean pulse duration between different characteristic patterns may require a greater number of pulse durations within each characteristic pattern to distinguish one from another with statistical confidence.

Preparation of Peptides for Functionalization

In some embodiments, peptides to be used in accordance with the methods of the disclosure (e.g., to be modified or functionalized using any one of the compounds of the disclosure, e.g., compounds of Formulae (II)-(IV), (VI), (VII), or (XII)-(XIV)) may be derived from, purified from, or isolated from any conceivable source.

For example, in some embodiments, a peptide sample is derived from, purified from, or isolated from a cell lysate, a single-cell, a population of cells, or a tissue. In some embodiments, a peptide sample is derived from, purified from, or isolated from a biological sample. In some embodiments, a a biological sample is a blood, saliva, sputum, feces, urine or buccal swab. In some embodiments, a biological sample is from a human, a non-human primate, a rodent, a dog, a cat, a horse, or any other mammal. In some embodiments, a biological sample is from a bacterial cell culture (e.g., an *E. coli* bacterial cell culture). A bacterial cell culture may comprise gram positive bacterial cells and/or gram negative bacterial cells.

In some embodiments, a peptide sample has been previously extracted via user-developed methods from metagenomic samples or environmental samples. In some embodiments, a peptide sample is derived from, purified from, or isolated from a blood sample, which may be a freshly drawn blood sample from a subject (e.g., a human subject) or a dried blood sample (e.g., preserved on solid media (e.g. Guthrie cards)). A blood sample may comprise whole blood, serum, plasma, red blood cells, and/or white blood cells.

In some embodiments, a biological sample (e.g., a biological sample comprising a peptide sample for use in the disclosure), may be lysed (e.g., disrupted, degraded and/or otherwise digested). In some embodiments, a biological sample comprising a peptide sample for use in the disclosure is lysed using any one of known physical or chemical methodologies to release the peptide sample from within cells or tissues. In some embodiments, a biological sample comprising a peptide sample for use in the disclosure is lysed using an electrolytic method, an enzymatic method, a detergent-based method, and/or mechanical homogenization. In some embodiments, a biological sample comprising a peptide sample for use in the disclosure requires multiple lysis methods performed in series. In some embodiments, a lysis method further includes use of a mill to grind a sample, sonication, surface acoustic waves (SAW), freeze-thaw cycles, heating, addition of detergents, addition of protein degradants (e.g., enzymes such as hydrolases or proteases), and/or addition of cell wall digesting enzymes (e.g., lysozyme or zymolase). Exemplary detergents (e.g., non-ionic detergents) for lysis include polyoxyethylene fatty alcohol ethers, polyoxyethylene alkylphenyl ethers, polyoxyethylene-polyoxypropylene block copolymers, polysorbates and alkylphenol ethoxylates, preferably nonylphenol ethoxylates, alkylglucosides and/or polyoxyethylene alkyl phenyl ethers. In some embodiments, lysis methods involve heating a sample for at least 1-30 min, 1-25 min, 5-25 min, 5-20 min, 10-30 min, 5-10 min, 10-20 min, or at least 5 min at a desired temperature (e.g., at least 60° C., at least 70° C., at least 80° C., at least 90° C., or at least 95° C.).

In some embodiments, a peptide sample for use in the disclosure is purified, e.g., following lysis of a biological sample, before terminal end functionalization of the peptides of the peptide sample. In some embodiments, a peptide sample is purified following terminal end functionalization by the methods described herein.

In some embodiments, a peptide sample is purified using chromatography (e.g., affinity chromatography that selectively binds the sample) or electrophoresis. In some embodiments, a peptide sample is purified in the presence of precipitating agents. In some embodiments, after a purification step or method, a peptide sample may be washed and/or released from a purification matrix (e.g., affinity chromatography matrix) using an elution buffer. In some embodiments, a purification step or method may comprise the use of a reversibly switchable polymer, such as an electroactive polymer. In some embodiments, a sample may be purified by electrophoretic passage of a sample through a porous matrix (e.g., cellulose acetate, agarose, acrylamide).

In some embodiments, a peptide sample may be fragmented before terminal end functionalization using the methods described herein. In some embodiments, a peptide sample may be fragmented to produce peptide fragments of any length. Fragmentation of proteins may, in some embodiments, be accomplished using chemical and/or enzymatic (e.g., proteolytic enzymes such as trypsin) methods. In some embodiments, mean fragment length may be controlled by reaction time, temperature, and concentration of sample and/or enzymes (e.g., restriction enzymes, transposases).

In some embodiments, a biological sample comprising a peptide sample for use in the disclosure is enriched for a target peptide to be terminally functionalized. In some embodiments, a biological sample is enriched for a target peptide using an electropheretic method. In some embodiments, a biological sample is enriched for a target peptide using affinity SCODA. In some embodiments, a biological sample is enriched for a target peptide using field inversion gel electrophoresis (FIGE). In some embodiments, a biological sample is enriched for a target peptide using pulsed field gel electrophoresis (PFGE). In some embodiments, the matrix used during enrichment (e.g., a porous media, electrophoretic polymer gel) comprises immobilized affinity agents (also known as 'immobilized capture probes') that bind to target peptide present in the biological sample. In some embodiments, a matrix used during enrichment comprises 1, 2, 3, 4, 5, or more unique immobilized capture probes, each of which binds to a unique target molecule and/or bind to the same target molecule with different binding affinities.

In some embodiments, an immobilized capture probe is a peptide capture probe (e.g., an aptamer or an antibody) that binds to a target peptide. In some embodiments, a peptide capture probe binds to a target peptide with a binding affinity of $10^{-9}$ to $10^{-8}$ M, $10^{-8}$ to $10^{-7}$ M, $10^{-7}$ to $10^{-6}$ M, $10^{-6}$ to $10^{-5}$ M, $10^{-5}$ to $10^{-4}$ M, $10^{-4}$ to $10^{-3}$ M, or $10^{-3}$ to $10^{1}$ M. In some embodiments, the binding affinity is in the picomolar to nanomolar range (e.g., between about $10^{-12}$ and about $10^{-9}$ M). In some embodiments, the binding affinity is in the nanomolar to micromolar range (e.g., between about $10^{-9}$ and about $10^{-6}$ M). In some embodiments, the binding affinity is in the micromolar to millimolar range (e.g., between about $10^{-6}$ and about $10^{-3}$ M). In some embodiments, the binding affinity is in the picomolar to micromolar range (e.g., between about $10^{-12}$ and about $10^{-6}$ M). In some embodiments, the binding affinity is in the nanomolar to millimolar range (e.g., between about $10^{-9}$ and about $10^{-3}$M). In some embodiments, a single peptide capture probe may be used to enrich a plurality of related target peptides that share at least 50%, 60%, 70%, 80%, 90% 95%, or 99% sequence identity. In some embodiments, a single peptide capture probe may be used to enrich a plurality of related target peptides (e.g., 2, 3, 4, 5, 6, 7, 8, 9, 10, 20, 30, 40, 50, or more related target proteins) that share at least 50%, 60%, 70%, 80%, 90% 95%, or 99% sequence homology.

In some embodiments, a target peptide to be functionalized may be released from the enrichment matrix after removal of non-target molecules. In some embodiments, a target peptide may be released from the enrichment matrix by increasing the temperature of the enrichment matrix. Adjusting the temperature of the matrix further influences migration rate as increased temperatures provide a higher capture probe stringency, requiring greater binding affinities between the target peptide and the capture probe. In some embodiments, when enriching related target molecules, the matrix temperature may be gradually increased in a stepwise manner in order to release and isolate target molecules in steps of ever-increasing homology. In some embodiments, temperature is increased by about 5%, 10%, 15%, 20%, 25%, 30%, 40%, 50%, or more in each step or over a period of time (e.g., 1-10 min, 1-5 min, or 4-8 min). In some embodiments, temperature is increased by 5%-10%, 5-15%, 5%-20%, 5%-25%, 5%-30%, 5%-40%, 5%-50%, 10%-25%, 20%-30%, 30%-40%, 35%-50%, or 40%-70% in each step or over a period of time (e.g., 1-10 min, 1-5 min, or 4-8 min). In some embodiments, temperature is increased by about 1° C., 2° C., 3° C., 4° C., 5° C., 6° C., 7° C., 8° C., 9° C., or 10° C. in each step or over a period of time (e.g., 1-10 min, 1-5 min, or 4-8 min). In some embodiments, temperature is increased by 1-10° C., 1-5° C., 2-5° C., 2-10° C., 3-8° C., 4-9° C., or 5-10° C. in each step or over a period of time (e.g., 1-10 min, 1-5 min, or 4-8 min).

Automated Methods

In certain embodiments, one or more of the methods described herein is automated. In certain embodiments, two, three, or four of the methods described herein are automated.

Any combination of automated methods may be performed using the same, or different, apparatuses. In certain embodiments, more than one automated method is performed in a single apparatus, wherein the apparatus comprises a plurality of cartridges or compartments, and wherein one or more method is performed in a single cartridge.

Figure 27:
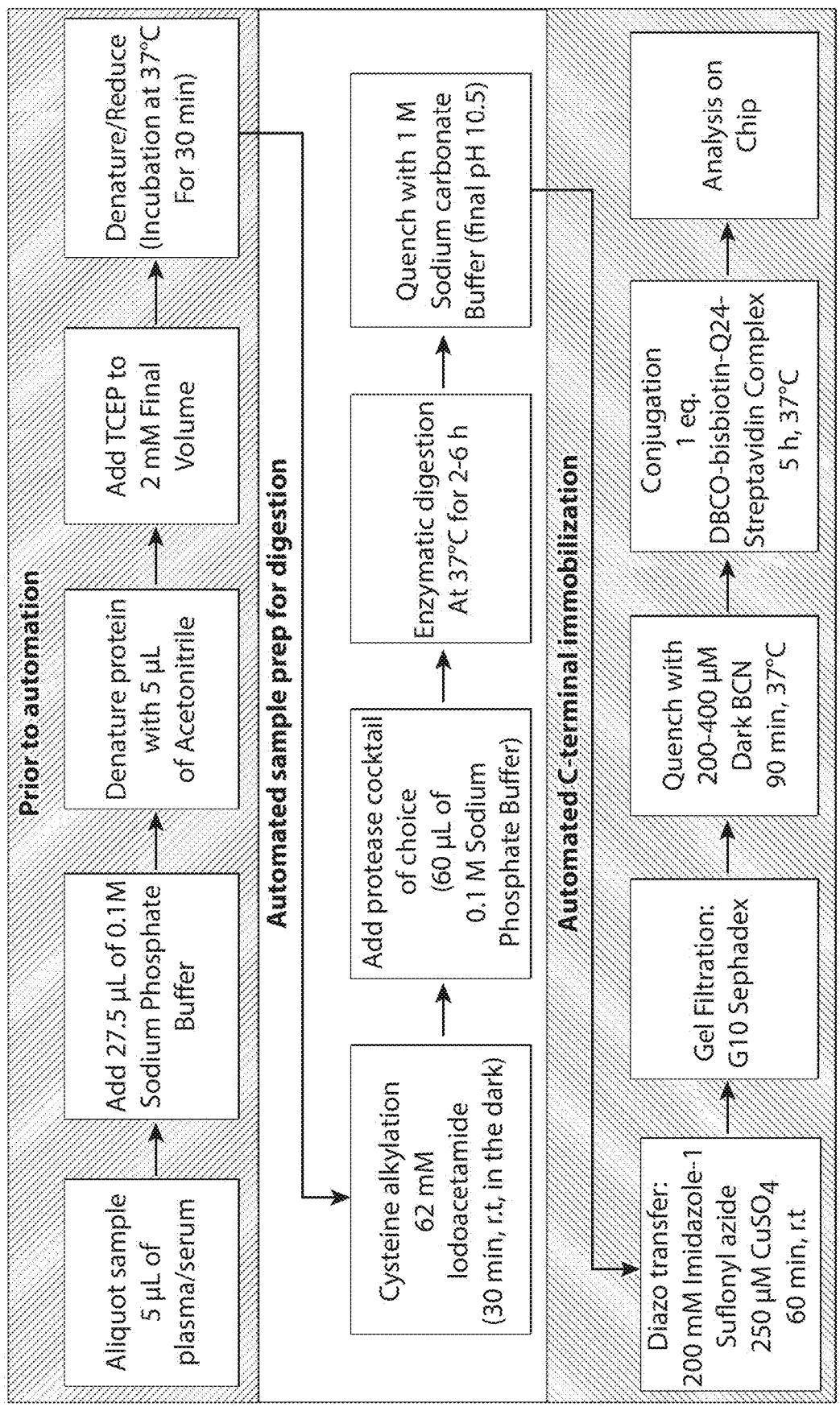
FIG. 27 shows an exemplary automated workflow using lysine derivatization.
Figure 28:
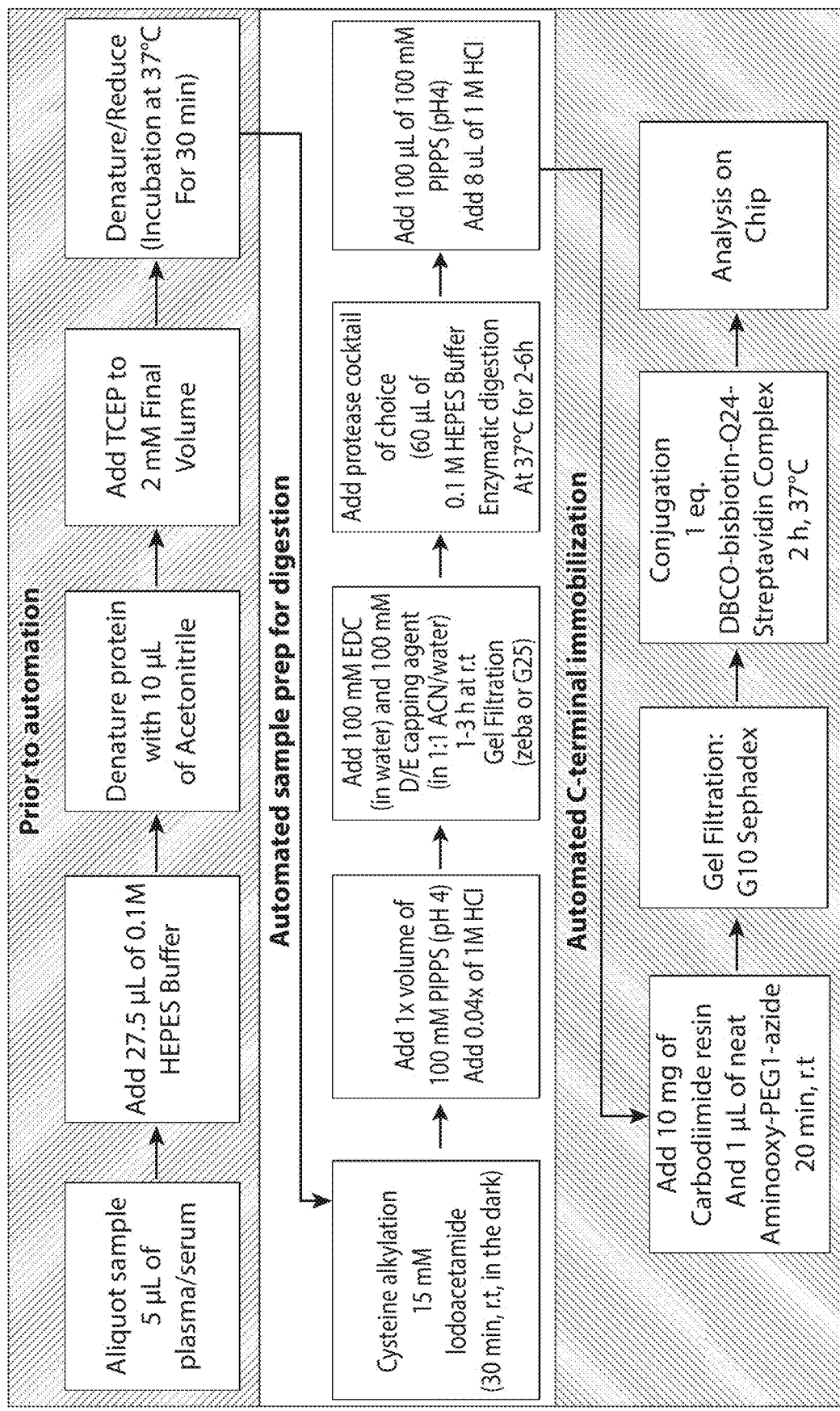
FIG. 28 shows an exemplary automated workflow using C-terminal modification.

Exemplary automation workflows are shown in FIGS. 27 and 28. These workflows depict steps performed prior to automated steps, as well as automated steps for sample prep (i.e., sample preparation) for digestion, and automated steps for C-terminal immobilization.

Definitions

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense (i.e., as "including, but not limited to").

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless defined otherwise, all technical and scientific terms used herein have the same meaning as is commonly understood by one of skill in the art to which this invention belongs. As used in the specification and claims, the singular form "a", "an", and "the" include plural references unless the context clearly dictates otherwise.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 20 carbon atoms ("$C_{1-20}$ alkyl") In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-10}$ alkyl (such as substituted $C_{1-6}$ alkyl, e.g., —$CH_2F$, —$CHF_2$, —$CF_3$ or benzyl (Bn)). An alkyl group may be branched or unbranched.

The term "alkenyl" refers to a radical of a straight-chain or branched hydrocarbon group having from 1 to 20 carbon atoms and one or more carbon-carbon double bonds (e.g., 1, 2, 3, or 4 double bonds). In some embodiments, an alkenyl group has 1 to 20 carbon atoms ("$C_{1-20}$ alkenyl"). In some embodiments, an alkenyl group has 1 to 12 carbon atoms ("$C_{1-12}$ alkenyl"). In some embodiments, an alkenyl group has 1 to 11 carbon atoms ("$C_{1-11}$ alkenyl"). In some embodiments, an alkenyl group has 1 to 10 carbon atoms ("$C_{1-10}$ alkenyl"). In some embodiments, an alkenyl group has 1 to 9 carbon atoms ("$C_{1-9}$ alkenyl"). In some embodiments, an alkenyl group has 1 to 8 carbon atoms ("$C_{1-8}$ alkenyl"). In some embodiments, an alkenyl group has 1 to 7 carbon atoms ("$C_{1-7}$ alkenyl"). In some embodiments, an alkenyl group has 1 to 6 carbon atoms ("$C_{1-6}$ alkenyl"). In some embodiments, an alkenyl group has 1 to 5 carbon atoms ("$C_{1-5}$ alkenyl"). In some embodiments, an alkenyl group has 1 to 4 carbon atoms ("$C_{1-4}$ alkenyl"). In some embodiments, an alkenyl group has 1 to 3 carbon atoms ("$C_{1-3}$ alkenyl"). In some embodiments, an alkenyl group has 1 to 2 carbon atoms ("$C_{1-2}$ alkenyl"). In some embodiments, an alkenyl group has 1 carbon atom ("$C_1$ alkenyl"). The one or more carbon-carbon double bonds can be internal (such as in 2-butenyl) or terminal (such as in 1-butenyl). Examples of $C_{1-4}$ alkenyl groups include methylidenyl ($C_1$), ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{1-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{1-20}$ alkenyl. In certain embodiments, the alkenyl group is a substituted $C_{1-20}$ alkenyl. In an alkenyl group, a C=C double bond for which the stereochemistry is not specified (e.g., —CH=$CHCH_3$ or

)

may be in the (F)- or (Z)-configuration.

The term "heteroalkenyl" refers to an alkenyl group, which further includes at least one heteroatom (e.g., 1, 2, 3, or 4 heteroatoms) selected from oxygen, nitrogen, or sulfur within (e.g., inserted between adjacent carbon atoms of) and/or placed at one or more terminal position(s) of the parent chain. In certain embodiments, a heteroalkenyl group refers to a group having from 1 to 20 carbon atoms, at least one double bond, and 1 or more heteroatoms within the parent chain ("heteroC$_{1-20}$ alkenyl"). In certain embodiments, a heteroalkenyl group refers to a group having from 1 to 12 carbon atoms, at least one double bond, and 1 or more heteroatoms within the parent chain ("heteroC$_{1-12}$ alkenyl"). In certain embodiments, a heteroalkenyl group refers to a group having from 1 to 11 carbon atoms, at least one double bond, and 1 or more heteroatoms within the parent chain ("heteroC$_{1-11}$ alkenyl"). In certain embodiments, a heteroalkenyl group refers to a group having from 1 to 10 carbon atoms, at least one double bond, and 1 or more heteroatoms within the parent chain ("heteroC$_{1-10}$ alkenyl"). In some embodiments, a heteroalkenyl group has 1 to 9 carbon atoms at least one double bond, and 1 or more heteroatoms within the parent chain ("heteroC$_{1-9}$ alkenyl"). In some embodiments, a heteroalkenyl group has 1 to 8 carbon atoms, at least one double bond, and 1 or more heteroatoms within the parent chain ("heteroC$_{1-8}$ alkenyl"). In some embodiments, a heteroalkenyl group has 1 to 7 carbon atoms, at least one double bond, and 1 or more heteroatoms within the parent chain ("heteroC$_{1-7}$ alkenyl"). In some embodiments, a heteroalkenyl group has 1 to 6 carbon atoms, at least one double bond, and 1 or more heteroatoms within the parent chain ("heteroC$_{1-6}$ alkenyl"). In some embodiments, a heteroalkenyl group has 1 to 5 carbon atoms, at least one double bond, and 1 or 2 heteroatoms within the parent chain ("heteroC$_{1-5}$ alkenyl"). In some embodiments, a heteroalkenyl group has 1 to 4 carbon atoms, at least one double bond, and 1 or 2 heteroatoms within the parent chain ("heteroC$_{1-4}$ alkenyl"). In some embodiments, a heteroalkenyl group has 1 to 3 carbon atoms, at least one double bond, and 1 heteroatom within the parent chain ("heteroC$_{1-3}$ alkenyl"). In some embodiments, a heteroalkenyl group has 1 to 2 carbon atoms, at least one double bond, and 1 heteroatom within the parent chain ("heteroC$_{1-2}$ alkenyl"). In some embodiments, a heteroalkenyl group has 1 to 6 carbon atoms, at least one double bond, and 1 or 2 heteroatoms within the parent chain ("heteroC$_{1-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{1-20}$ alkenyl. In certain embodiments, the heteroalkenyl group is a substituted heteroC$_{1-20}$ alkenyl.

The term "alkynyl" refers to a radical of a straight-chain or branched hydrocarbon group having from 1 to 20 carbon atoms and one or more carbon-carbon triple bonds (e.g., 1, 2, 3, or 4 triple bonds) ("C$_{1-20}$ alkynyl"). In some embodiments, an alkynyl group has 1 to 10 carbon atoms ("C$_{1-10}$ alkynyl"). In some embodiments, an alkynyl group has 1 to 9 carbon atoms ("C$_{1-9}$ alkynyl"). In some embodiments, an alkynyl group has 1 to 8 carbon atoms ("C$_{1-8}$ alkynyl"). In some embodiments, an alkynyl group has 1 to 7 carbon atoms ("C$_{1-7}$ alkynyl"). In some embodiments, an alkynyl group has 1 to 6 carbon atoms ("C$_{1-6}$ alkynyl"). In some embodiments, an alkynyl group has 1 to 5 carbon atoms ("C$_{1-5}$ alkynyl"). In some embodiments, an alkynyl group has 1 to 4 carbon atoms ("C$_{1-4}$ alkynyl"). In some embodiments, an alkynyl group has 1 to 3 carbon atoms ("C$_{1-3}$ alkynyl"). In some embodiments, an alkynyl group has 1 to 2 carbon atoms ("C$_{1-2}$ alkynyl"). In some embodiments, an alkynyl group has 1 carbon atom ("C$_1$ alkynyl"). The one or more carbon-carbon triple bonds can be internal (such as in 2-butynyl) or terminal (such as in 1-butynyl). Examples of C$_{1-4}$ alkynyl groups include, without limitation, methylidynyl (C$_1$), ethynyl (C$_2$), 1-propynyl (C$_3$), 2-propynyl (C$_3$), 1-butynyl (C$_4$), 2-butynyl (C$_4$), and the like. Examples of C$_{1-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{1-20}$ alkynyl. In certain embodiments, the alkynyl group is a substituted C$_{1-20}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (e.g., inserted between adjacent carbon atoms of) and/or placed at one or more terminal position(s) of the parent chain. In certain embodiments, a heteroalkynyl group refers to a group having from 1 to 20 carbon atoms, at least one triple bond, and 1 or more heteroatoms within the parent chain ("heteroC$_{1-20}$ alkynyl"). In certain embodiments, a heteroalkynyl group refers to a group having from 1 to 10 carbon atoms, at least one triple bond, and 1 or more heteroatoms within the parent chain ("heteroC$_{1-10}$ alkynyl"). In some embodiments, a heteroalkynyl group has 1 to 9 carbon atoms, at least one triple bond, and 1 or more heteroatoms within the parent chain ("heteroC$_{1-9}$ alkynyl"). In some embodiments, a heteroalkynyl group has 1 to 8 carbon atoms, at least one triple bond, and 1 or more heteroatoms within the parent chain ("heteroC$_{1-8}$ alkynyl"). In some embodiments, a heteroalkynyl group has 1 to 7 carbon atoms, at least one triple bond, and 1 or more heteroatoms within the parent chain ("heteroC$_{1-7}$ alkynyl"). In some embodiments, a heteroalkynyl group has 1 to 6 carbon atoms, at least one triple bond, and 1 or more heteroatoms within the parent chain ("heteroC$_{1-6}$ alkynyl"). In some embodiments, a heteroalkynyl group has 1 to 5 carbon atoms, at least one triple bond, and 1 or 2 heteroatoms within the parent chain ("heteroC$_{1-5}$ alkynyl"). In some embodiments, a heteroalkynyl group has 1 to 4 carbon atoms, at least one triple bond, and 1 or 2 heteroatoms within the parent chain ("heteroC$_{1-4}$ alkynyl"). In some embodiments, a heteroalkynyl group has 1 to 3 carbon atoms, at least one triple bond, and 1 heteroatom within the parent chain ("heteroC$_{1-3}$ alkynyl"). In some embodiments, a heteroalkynyl group has 1 to 2 carbon atoms, at least one triple bond, and 1 heteroatom within the parent chain ("heteroC$_{1-2}$ alkynyl"). In some embodiments, a heteroalkynyl group has 1 to 6 carbon atoms, at least one triple bond, and 1 or 2 heteroatoms within the parent chain ("heteroC$_{1-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{1-20}$ alkynyl. In certain embodiments, the heteroalkynyl group is a substituted heteroC$_{1-20}$ alkynyl.

"Aralkyl" is a subset of "alkyl" and refers to an alkyl group substituted by an aryl group, wherein the point of attachment is on the alkyl moiety As used herein, the term "alkoxy" refers to an alkyl group having an oxygen atom that connects the alkyl group to the point of attachment: i.e., alkyl-O—. As for the alkyl portions, alkoxy groups can have any suitable number of carbon atoms, such as C$_{1-6}$ or C$_{1-4}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. Alkoxy groups are unsubstituted, but can be described, in some embodiments as substituted. "Substituted alkoxy" groups can be substituted with one or more moieties selected from halo, hydroxy, amino, alkylamino, nitro, cyano, and alkoxy.

The term "cycloalkyl" refers to cyclic alkyl radical having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

The term "heteroalkyl," as used herein, refers to an alkyl group, as defined herein, in which one or more of the constituent carbon atoms have been replaced by a heteroatom or optionally substituted heteroatom, e.g., nitrogen (e.g.,

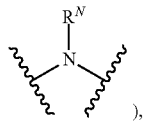

), oxygen (e.g.,

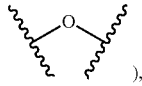

), or sulfur (e.g.,

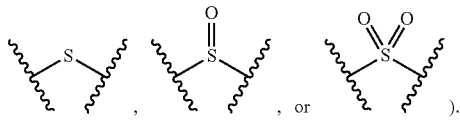

).

Heteroalkyl groups may be optionally substituted with one, two, three, or, in the case of alkyl groups of two carbons or more, four, five, or six substituents independently selected from any of the substituents described herein. Heteroalkyl group substituents include: (1) carbonyl; (2) halo; (3) $C_6$-$C_{10}$ aryl; and (4) $C_3$-$C_{10}$ carbocyclyl. A heteroalkylene is a divalent heteroalkyl group.

The term "alkoxy," as used herein, refers to —OR$^a$, where R$^a$ is, e.g., alkyl, alkenyl, alkynyl, aryl, alkylaryl, carbocyclyl, heterocyclyl, or heteroaryl. Examples of alkoxy groups include methoxy, ethoxy, isopropoxy, tert-butoxy, phenoxy, and benzyloxy.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents (e.g., —F, —OH or —O($C_{1-6}$ alkyl). In certain embodiments, the aryl group is an unsubstituted $C_{6-14}$ aryl. In certain embodiments, the aryl group is a substituted $C_{6-14}$ aryl.

The term "aryloxy" refers to an —O-aryl substituent.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl). In certain embodiments, the heteroaryl is substituted or unsubstituted, 5- or 6-membered, monocyclic heteroaryl, wherein 1, 2, 3, or 4 atoms in the heteroaryl ring system are independently oxygen, nitrogen, or sulfur. In certain embodiments, the heteroaryl is substituted or unsubstituted, 9- or 10-membered, bicyclic heteroaryl, wherein 1, 2, 3, or 4 atoms in the heteroaryl ring system are independently oxygen, nitrogen, or sulfur.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In certain embodiments, the heterocyclyl is substituted or unsubstituted, 3- to 7-membered, monocyclic heterocyclyl, wherein 1, 2, or 3 atoms in the heterocyclic ring system are independently oxygen, nitrogen, or sulfur, as valency permits.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

The term "carbonyl" refers a group wherein the carbon directly attached to the parent molecule is $sp^2$ hybridized, and is substituted with an oxygen, nitrogen or sulfur atom, e.g., a group selected from ketones (e.g., —C(=O)$R^{aa}$), carboxylic acids (e.g., —CO$_2$H), aldehydes (—CHO), esters (e.g., —CO$_2R^{aa}$, —C(=O)S$R^{aa}$, —C(=S)S$R^{aa}$), amides (e.g., —C(=O)N($R^{bb}$)$_2$, —C(=O)N$R^{bb}$ SO$_2R^{aa}$, —C(=S) N($R^{bb}$)$_2$), and imines (e.g., —C(=N$R^{bb}$)$R^{aa}$Q-N$R^{bb}$)O$R^{aa}$), —C(—N$R^{bb}$)N($R^{bb}$)$_2$), wherein $R^{aa}$ and $R^{bb}$ are as defined herein.

The term "amino," as used herein, represents —N($R^N$)$_2$, wherein each $R^N$ is, independently, H, OH, NO$_2$, N($R^{NO}$)$_2$, SO$_2$O$R^{NO}$, SO$_2R^{NO}$, SOR$^{NO}$, an N-protecting group, alkyl, alkoxy, aryl, cycloalkyl, acyl (e.g., acetyl, trifluoroacetyl, or others described herein), wherein each of these recited $R^N$ groups can be optionally substituted; or two $R^N$ combine to form an alkylene or heteroalkylene, and wherein each $R^{NO}$ is, independently, H, alkyl, or aryl. The amino groups of the disclosure can be an unsubstituted amino (i.e., —NH$_2$) or a substituted amino (i.e., —N($R^N$)$_2$).

The term "substituted" as used herein means at least one hydrogen atom is replaced by a bond to a non-hydrogen atoms such as, but not limited to: a halogen atom such as F, C$_1$, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, in some embodiments "substituted" means one or more hydrogen atoms are replaced with N$R_gR_h$, N$R_g$C(=O)$R_h$, N$R_g$C(=O)N$R_gR_h$, N$R_g$C(=O) O$R_h$, N$R_g$SO$_2R_h$, OC(=O)N$R_gR_h$, O$R_g$, S$R_g$, SO$R_g$, SO$_2R_g$, OSO$_2R_g$, SO$_2$O$R_g$, =NSO$_2R_g$, and SO$_2$N$R_gR_h$. "Substituted also means one or more hydrogen atoms are replaced with C(=O)$R_g$, C(=O)O$R_g$, C(=O)N$R_gR_h$, CH$_2$SO$_2R_g$, CH$_2$SO$_2$N$R_gR_h$.

In the foregoing, $R_g$ and $R_h$ are the same or different and independently hydrogen, alkyl, alkoxy, alkylaminyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means one or more hydrogen atoms are replaced by a bond to an aminyl, cyano, hydroxyl, imino, nitro, oxo, thioxo, halo, alkyl, alkoxy, alkylaminyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

The terms "salt thereof" or "salts thereof" as used herein refer to salts which are well known in the art. For example, Berge et al., describe pharmaceutically acceptable salts in detail in *J. Pharmaceutical Sciences*, 1977, 66, 1-19, incorporated herein by reference. Additional information on suitable salts can be found in Remington's Pharmaceutical Sciences, 17th ed., Mack Publishing Company, Easton, Pa., 1985, which is incorporated herein by reference. Salts of the compounds of this invention include those derived from suitable inorganic and organic acids and bases. Examples of acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counter ions such as halide, hydroxide, carboxylate, sulfate, phosphate, nitrate, lower alkyl sulfonate and aryl sulfonate.

A "protein," "peptide," or "polypeptide" comprises a polymer of amino acid residues linked together by peptide bonds. The terms refer to proteins, polypeptides, and peptides of any size, structure, or function. Typically, a protein or peptide will be at least three amino acids in length. In some embodiments, a peptide is between about 3 and about 100 amino acids in length (e.g., between about 5 and about 25, between about 10 and about 80, between about 15 and about 70, or between about 20 and about 40, amino acids in length). In some embodiments, a peptide is between about 6 and about 40 amino acids in length (e.g., between about 6 and about 30, between about 10 and about 30, between about 15 and about 40, or between about 20 and about 30, amino acids in length). In some embodiments, a plurality of peptides can refer to a plurality of peptide molecules, where each peptide molecule of the plurality comprises an amino acid sequence that is different from any other peptide molecule of the plurality. In some embodiments, a plurality of peptides can include at least 1 peptide and up to 1,000 peptides (e.g., at least 1 peptide and up to 10, 50, 100, 250, or 500 peptides). In some embodiments, a plurality of peptides comprises 1-5, 5-10, 1-15, 15-20, 10-100, 50-250, 100-500, 500-1,000, or more, different peptides. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein or peptide may be a fragment of a naturally occurring protein or peptide. A protein may be naturally occurring, recombinant, synthetic, or any combination of these.

With respect to the use of substantially any plural and/or singular terms herein, those having skill in the art can translate from the plural to the singular and/or from the singular to plural as is appropriate to the context and/or application. The various singular/plural permutations can be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Those skilled in the art will appreciate that certain compounds described herein can exist in one or more different isomeric (e.g., stereoisomers, geometric isomers, tautomers) and/or isotopic (e.g., in which one or more atoms has been substituted with a different isotope of the atom, such as hydrogen substituted for deuterium) forms. Unless otherwise indicated or clear from context, a depicted structure can be understood to represent any such isomeric or isotopic form, individually or in combination.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

EXAMPLES

Figure 4:
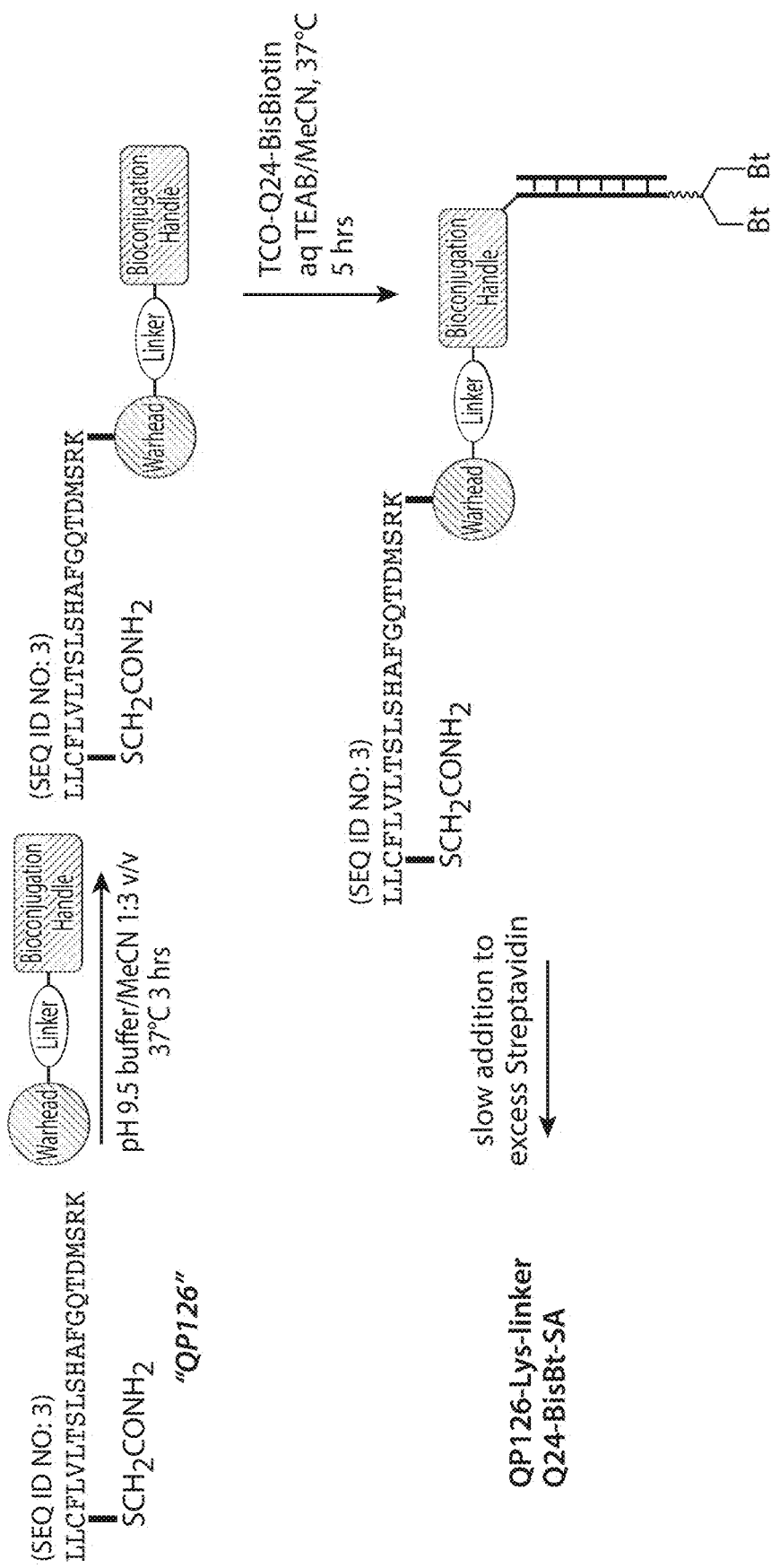
FIG. 4 shows a model C-terminal lysine coupling procedure.

Example 1. QP126, a synthetic peptide fragment from a hypothetical Lys-C only digest of full length CRP, was used as a substrate. Cysteine residues were capped with iodoacetamide. The functionalization of QP126 was then performed as shown in FIG. 4, followed by aqueous extraction to remove excess 4-nitrovinyl sulfonamide coupling reagent, then biorthogonal click reaction to a DNA linker. This was monoligated to streptavidin, purified by HPLC and quantified to allow for delivery of an appropriate concentration on chip.

Figure 5A:
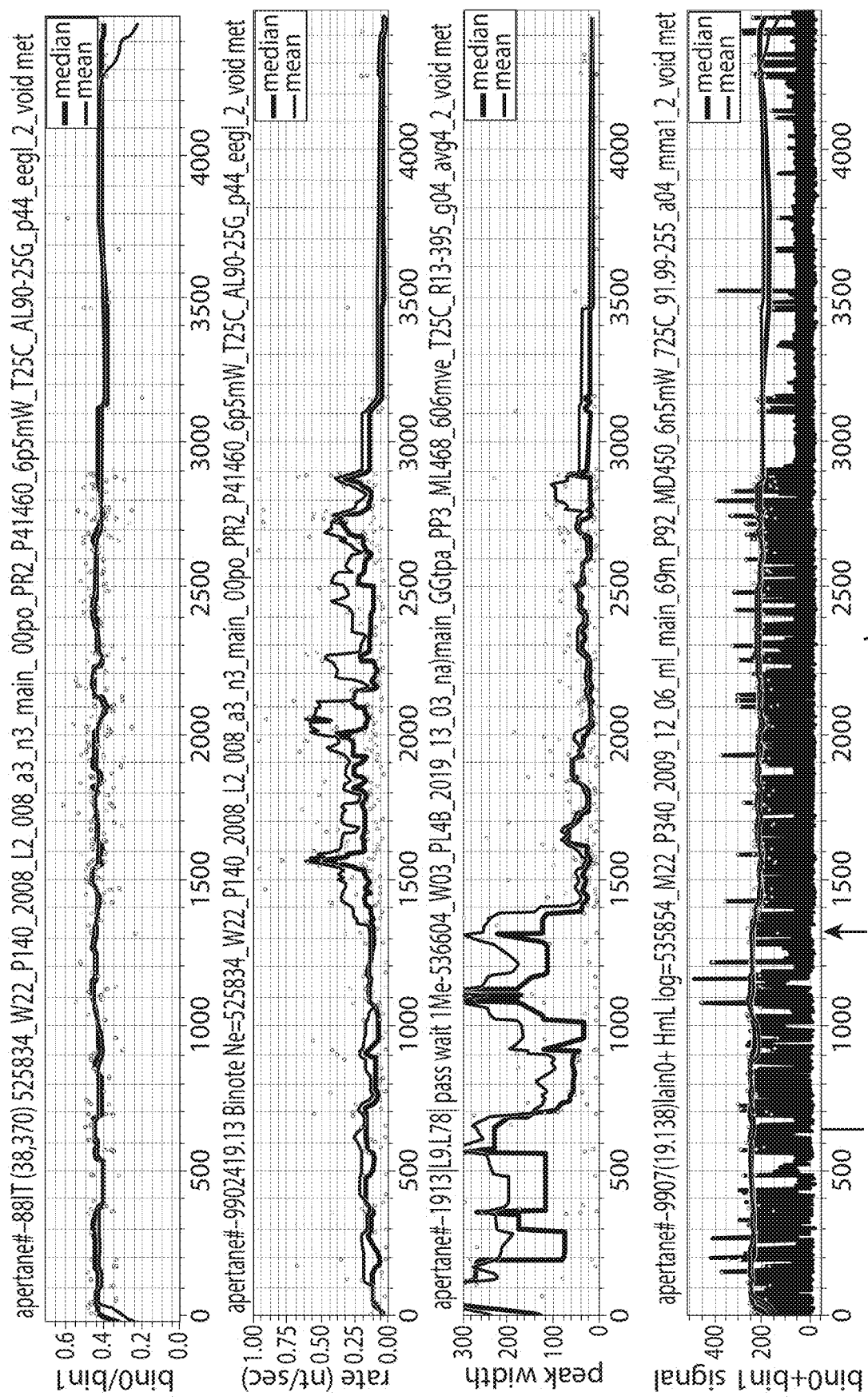
FIG. 5A-C show data related to a model C-terminal lysine coupling procedure.
Figure 5B:
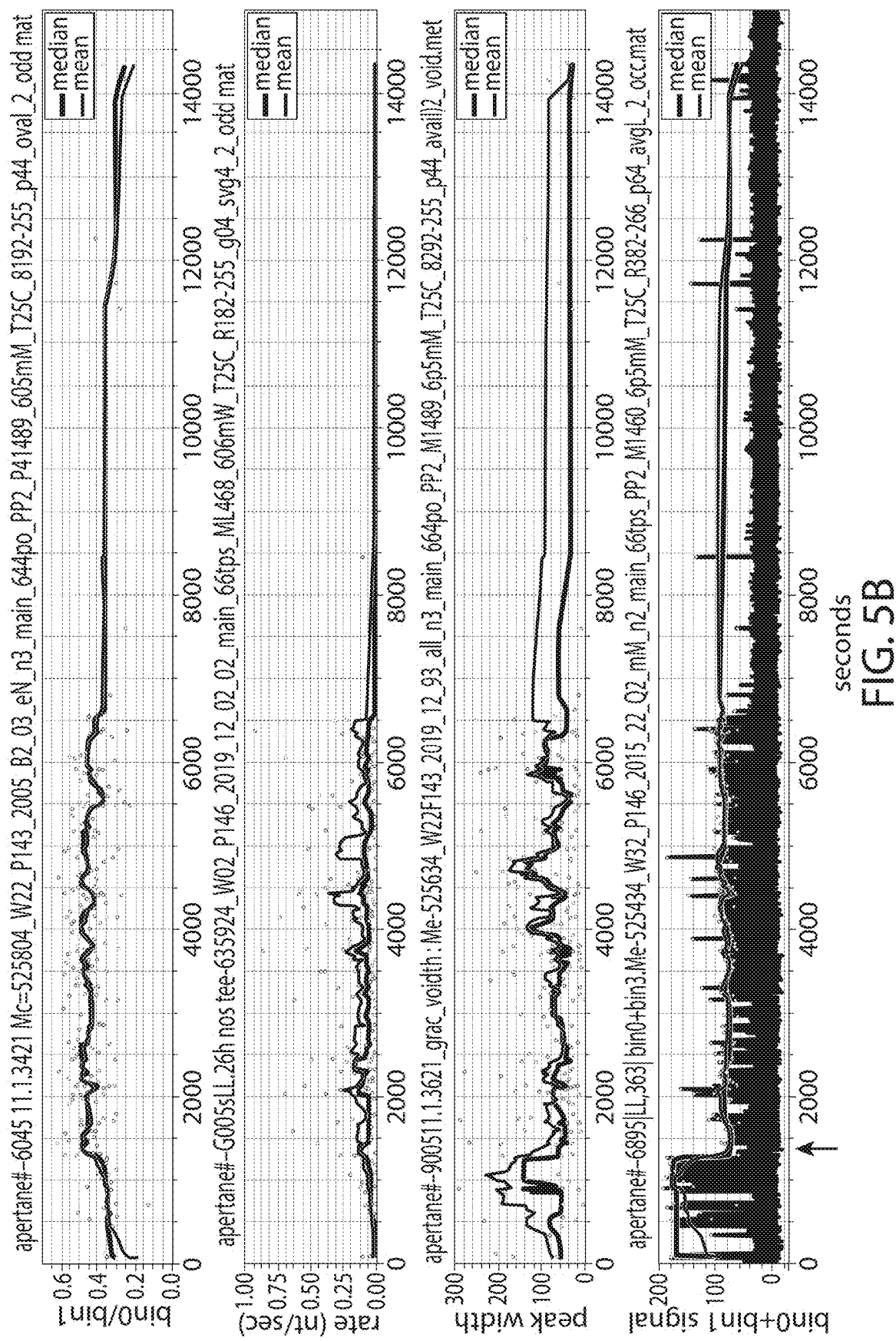
Figure 5C:
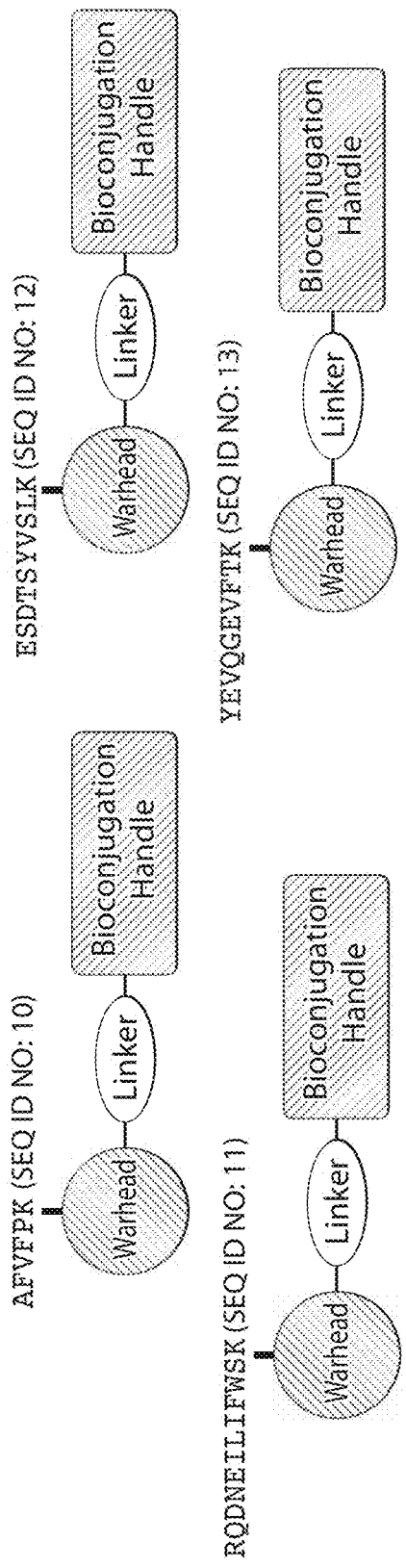
Figure 6:
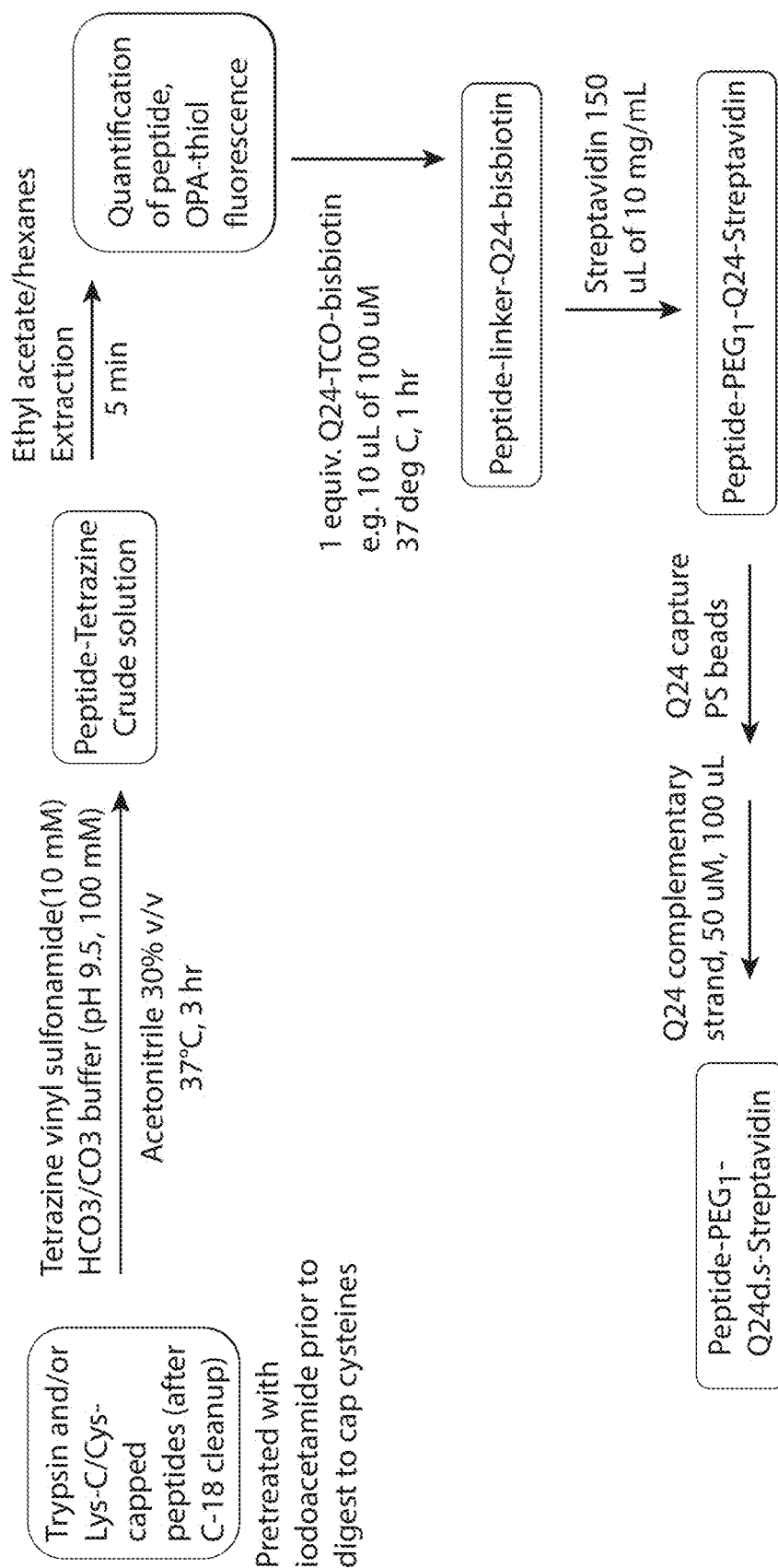
FIG. 6 shows a representative C-terminal lysine coupling procedure using the 4-nitrovinyl sulfonamide reagent.

Example 2. A crude digest (Lys-C/Trypsin) of truncated CRP was reacted with 4-nitrovinyl sulfonamide coupling reagent and incubated for 4 hours at 37° C., followed by LC/HRMS analysis. Four fragments from a predicted Lys-C/Trypsin digest were observed in their labeled forms, demonstrating the lysine reactive probe is capable of labeling fragments from a complex digestion mixture. See FIGS. 5A-C.

Figure 7A:
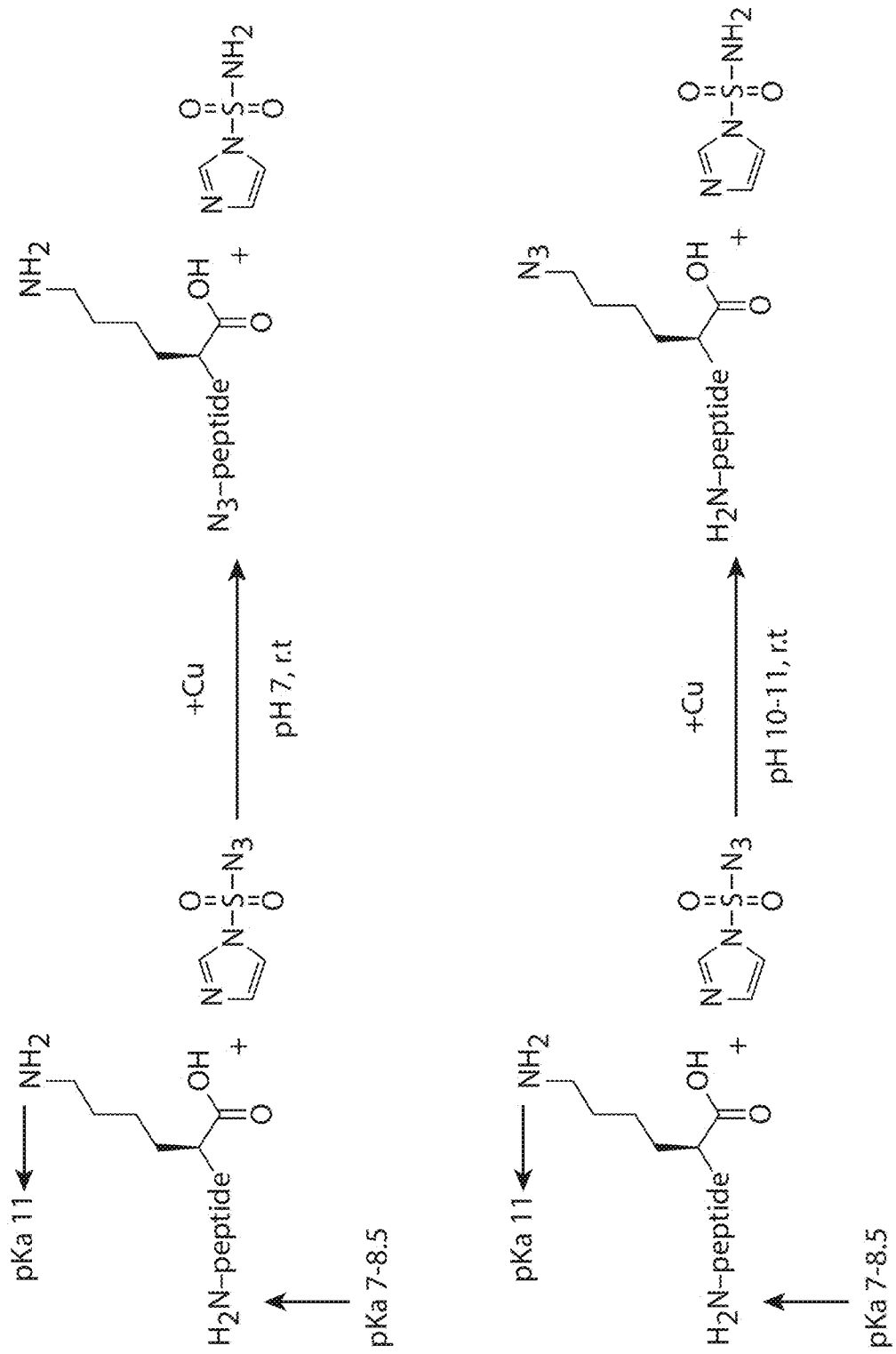
FIG. 7A-B show schemes related to an exemplary C-terminal lysine coupling procedure using diazo transfer chemistry.
Figure 7B:
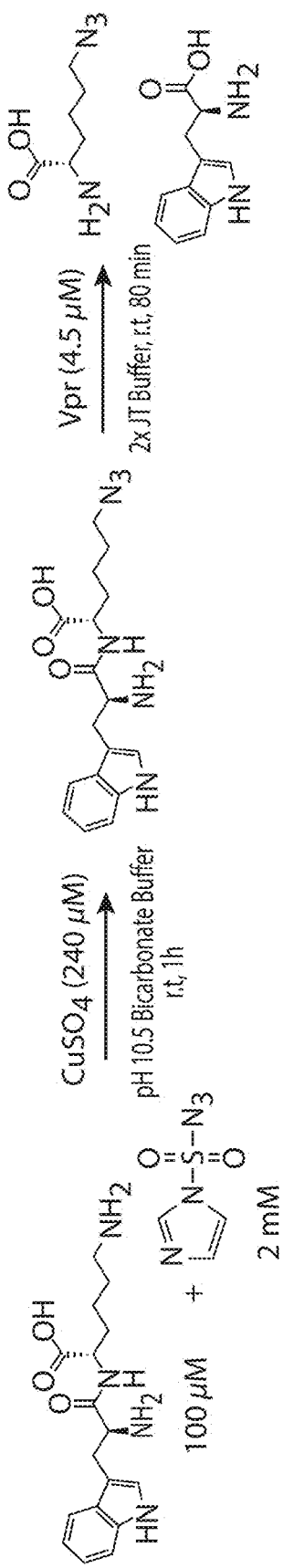
Figure 8:
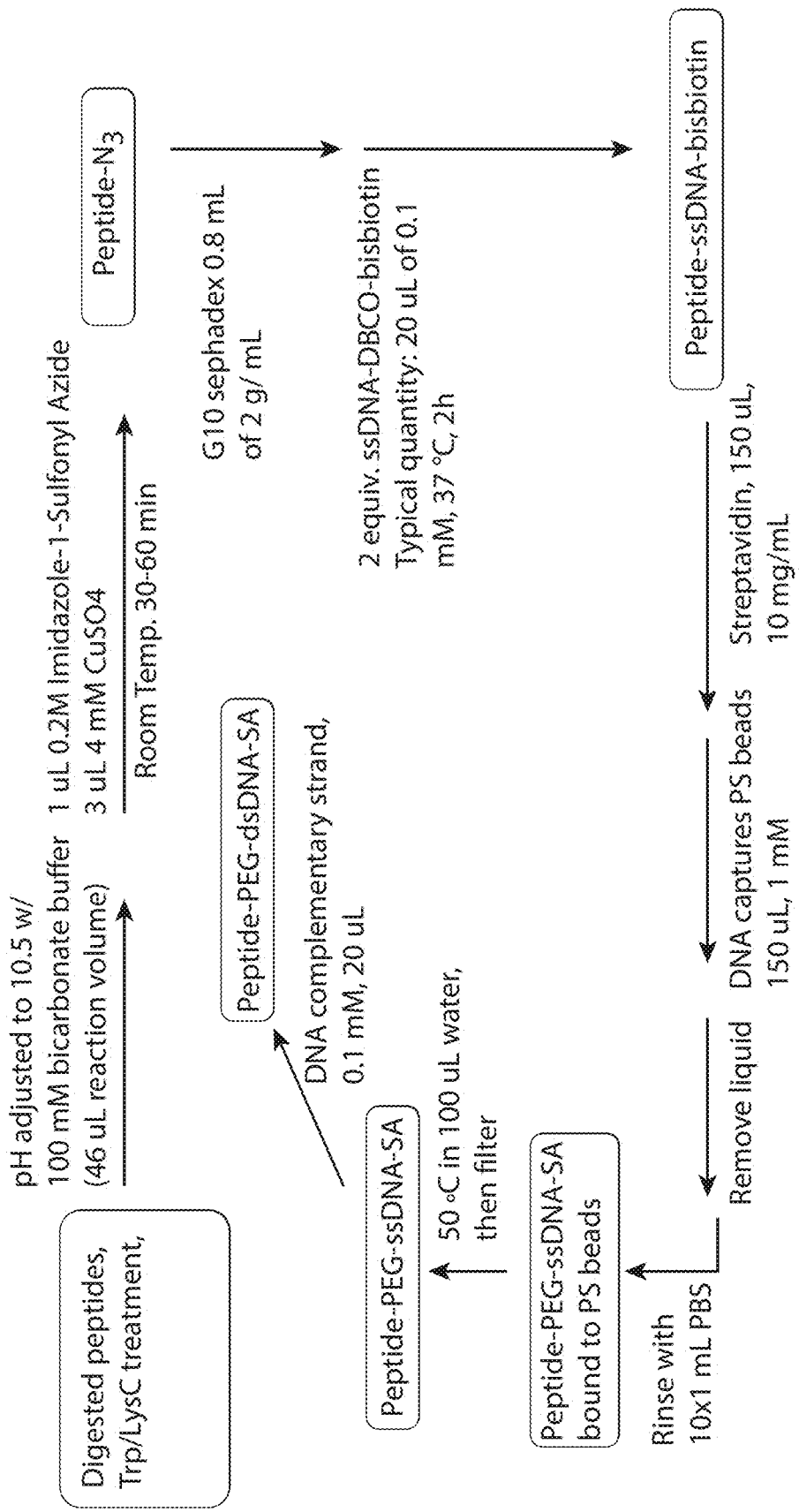
FIG. 8 shows a representative lysine coupling procedure using diazo transfer.

Example 3. This procedure converts C-terminal Lysines to ε-azido lysines via a diazotransfer using imidazole-1-sulfonyl azide. Lysine labeling methods often also result in labeling the N-terminal of proteins and peptides. However, in this method the diazo transfer can be directed to either the N-terminal or the ε-amine of lysine by modulating the pH of the reaction buffer. Specifically, the pKa of the N-terminal amino group ranges from ~7-8.5 (depending on the amino acid at the N-terminal), while the pKa of the ε-amine of lysine is ~11. As such, reactions performed at neutral pH direct the diazo transfer to the N-terminus, while reactions occurring at pH 10-11 will direct the diazo transfer to the ε-amine of lysine (FIG. 7A). It was first explored if Tryptophan-Lysine dipeptide (WK) could be selectively labeled with an ε-azide (FIG. 7B). The reaction was carried out with 100 μM of WK and 2 mM imidazole-1-sulfonyl azide in the presence of 240 μM Copper (as $CuSO_4$) (in pH 10.5 sodium bicarbonate buffer). After 1 hour at r.t, the reaction was analyzed by HPLC and Mass Spectrometry. It was found that the majority (~90%) of WK was mono-labeled and ~10% was bis-labeled with azides at the N-terminal and the ε-amine of lysine. The single azidified WK was isolated and subjected to digestion using Vpr (4.5 in 2×JT Buffer) for 80 min. After 80 min, HPLC analysis revealed that the mono-labeled WK was depleted and free tryptophan was identified by HPLC-UV and Mass Spectrometry. With this initial evidence in hand, a more complex peptide was labeled. The model peptide YAAWAAFADDDWK (SEQ ID NO: 4) (QP123) was used. 100 μM of QP123 was subjected to the same reaction conditions as WK for 1 h. After 1 h, HPLC and Mass Spectrometry revealed that ~90% of the peptide was mono-labeled labeled and ~10% of the peptide remained unreacted (no bis-labeled species was detected). The mono-labeled QP123 was isolated and subjected to Vpr digestion (9 μM, 1-2×JT buffer) for 60-90 min at r.t and the full-length product was not detected by HPLC and Mass Spectrometry, while many other peaks were detected by HPLC-UV. Mass spectrometry analysis revealed the major digestion products to be ADDDWK (SEQ ID NO: 5) and DDDWK (SEQ ID NO: 6) (both bearing an ε-azido lysine). The diazo transfer protocol was tested on about a dozen peptides, all resulting in consistent labeling of the ε-amine of lysines over the N-terminus. Additionally, we observed that reactions in the absence of copper occur at a much lower rate and with lower selectivity. When 100 uM QP123 was incubated with 2 mM of imidazole-1-sulfonyl azide (in pH 10.5 sodium bicarbonate buffer) in the absence of Copper, the two mono-labeled (lysine and N-terminal amine) along with the bis-labeled products were observed.

Example 4. A representative cysteine protection procedure involves:

1. 90 μL of CRP (1 mg/mL), 360 μL of 25 mM HEPES pH 7.8 w/10% acetonitrile, 0.23 μL of 0.5 M TCEP were combined and incubated at room temperature for 20 min; and 2. 9 μL of 0.5 M iodoacetamide was added, and the reaction was incubated in the dark for 30 min at room temperature.

Example 5. Sample denaturation for enzymatic digestion: In order to denature proteins for protease digestion the disulfide bonds need to be broken. This involves the reduction and alkylation of cysteine residues. Using Insulin as a model system, the following method was developed to reduce cysteines with TCEP (2 mM, 37° C., 30 min) and alkylate them with iodoacetamide (62 mM, r.t, 30 min in the dark). This protocol was validated on our Insulin sample using HPLC and Mass Spectrometry and complete reduction of disulfides was observed. Alkylation is nearly complete, with a single free-cysteine observed in no more than 30% of Insulin peptides. These conditions are compatible with automation and the buffers necessary for enzymatic digestion of samples from serum/plasma.

Figure 11:
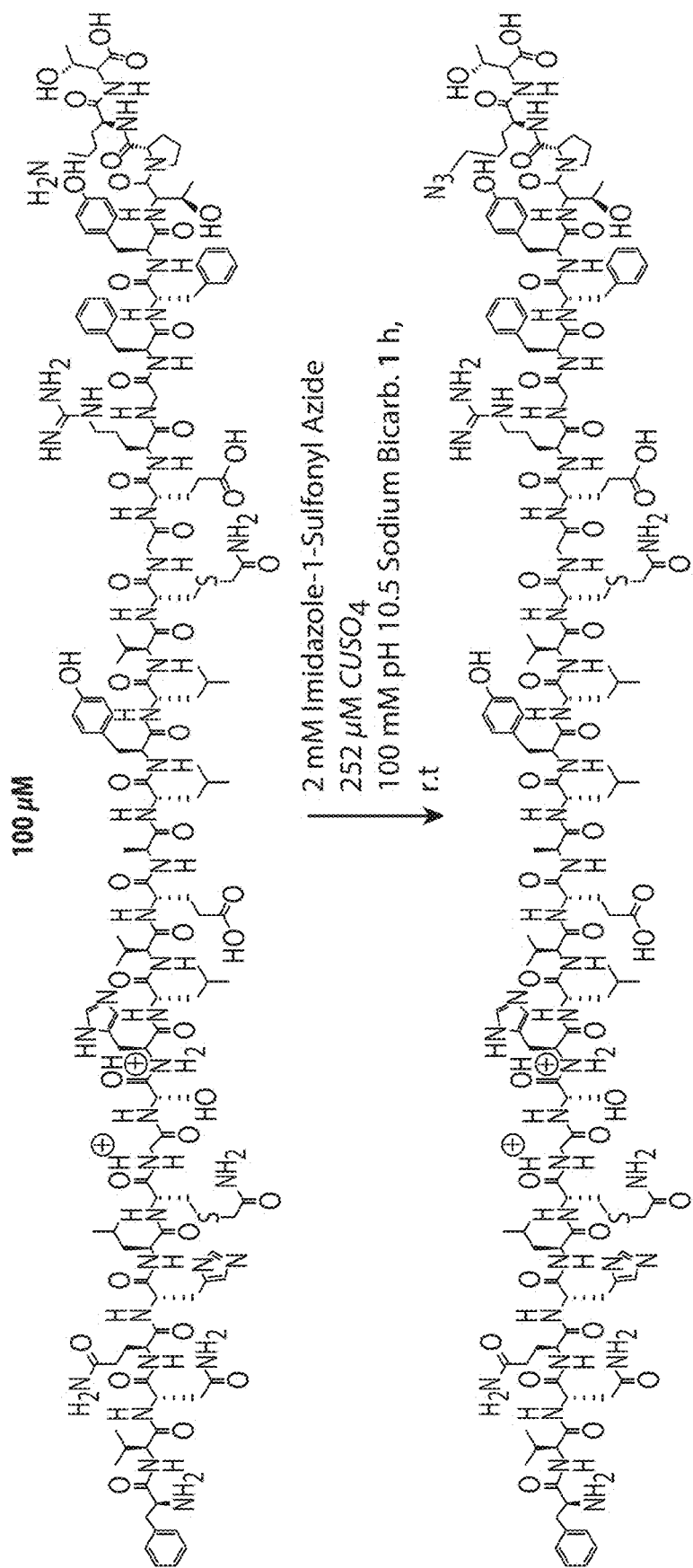
FIG. 11 shows labeling of Insulin chain B using diazo transfer.
Figure 12:
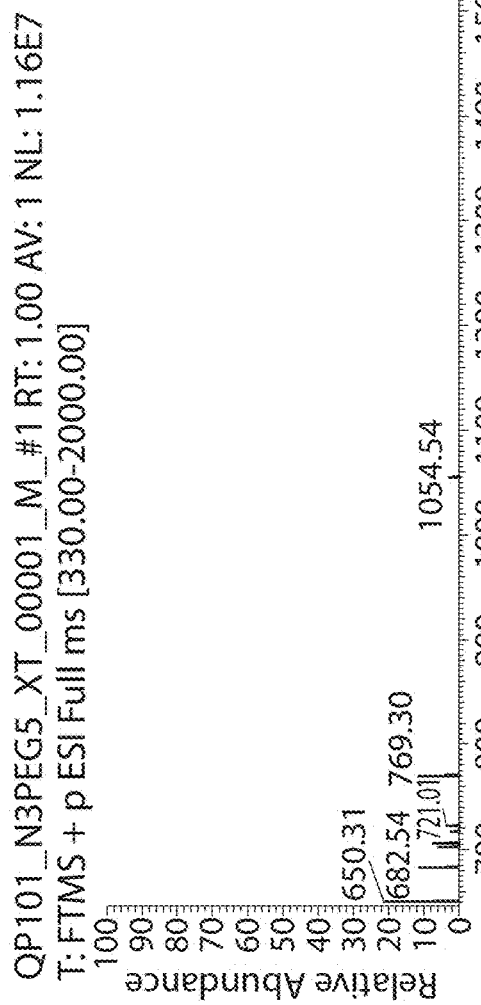
FIG. 12 shows a mass spectrum of QP101, a CRP-peptide that is the azido-PEG5-$ONH_2$ adduct of the peptide INTIYLGGPFSPNVLNWR (SEQ ID NO: 1), which was obtained by trypsin digestion. The adduct was formed using carbodiimide (EDC) coupling.
Figure 13:
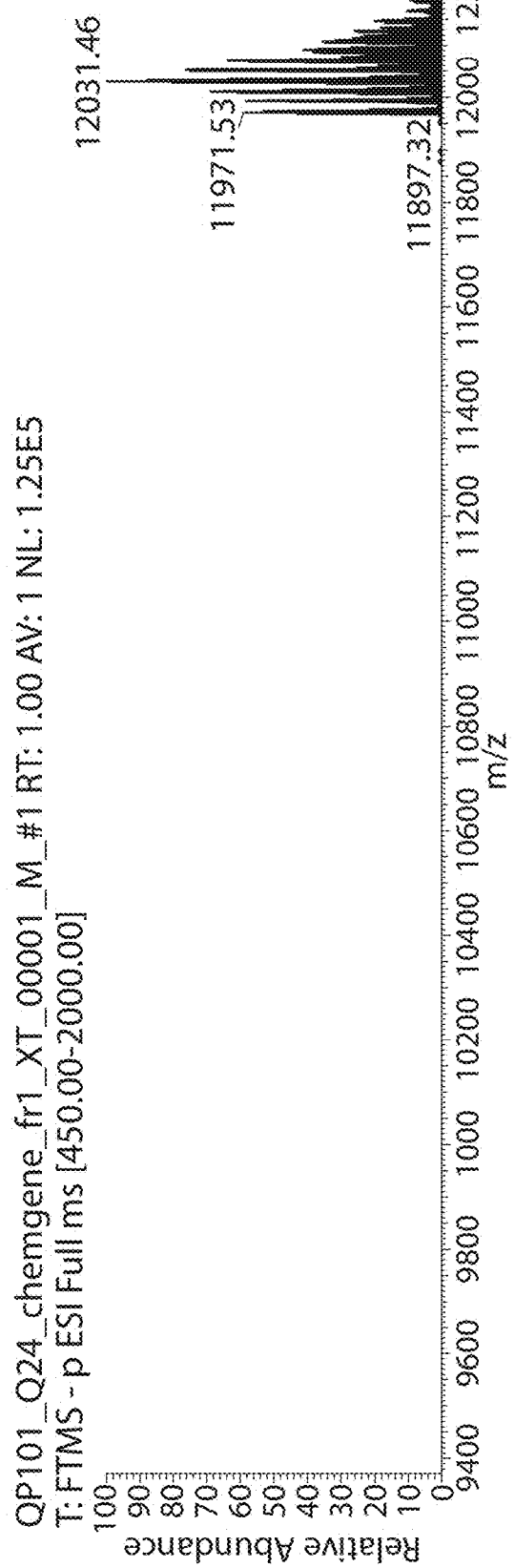
FIG. 13 shows a mass spectrum of the Q24-bisbiotin-BCN adduct (via click chemistry) of the azido-PEG5-$ONH_2$ adduct of QP101. The sequence of Q24 is CCACGCGTG-GAACCCTTGGGATCCA (SEQ ID NO: 2) (see FIG. 23A).
Figure 14:
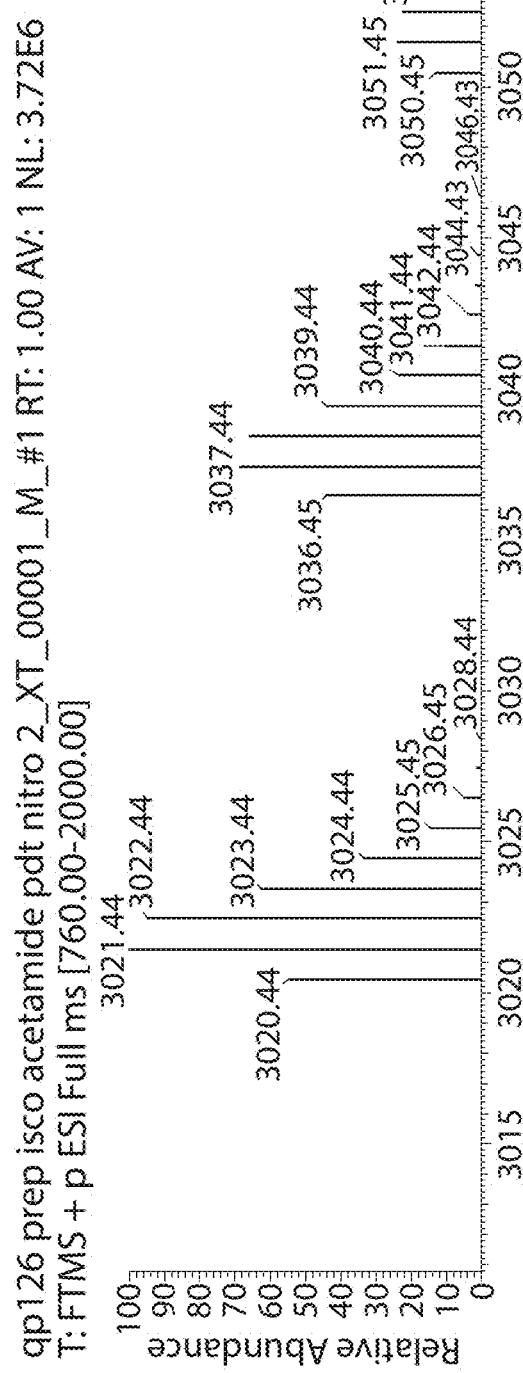
FIG. 14 shows a mass spectrum of QP126, a pre-CRP peptide LLCFLVLTSLSHAFGQTDMSRK (SEQ ID NO: 3) obtained from Lys-C digestion which has been S-protected using ICM chemistry, and activated as a nitrophenyl vinylsulfonamide-tetrazine (e.g., compound (VII)) adduct.
Figure 15:
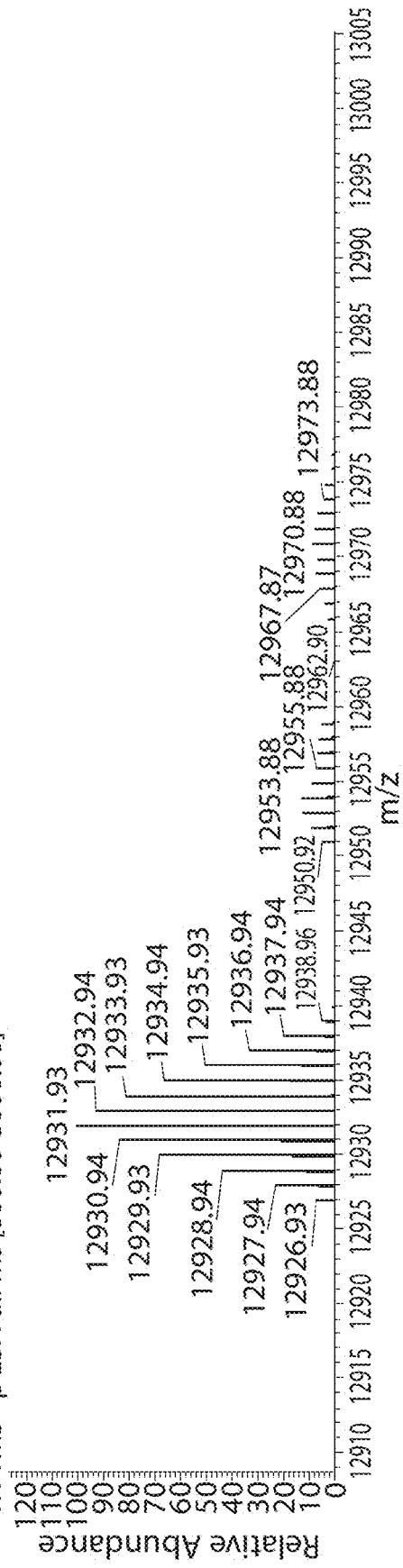
FIG. 15 shows a mass spectrum of the conjugation product (via click chemistry) of the QP126 nitrophenyl vinylsulfonamide-tetrazine adduct with Q24-bisbiotin-TCO (see FIG. 26A).
Figure 16:
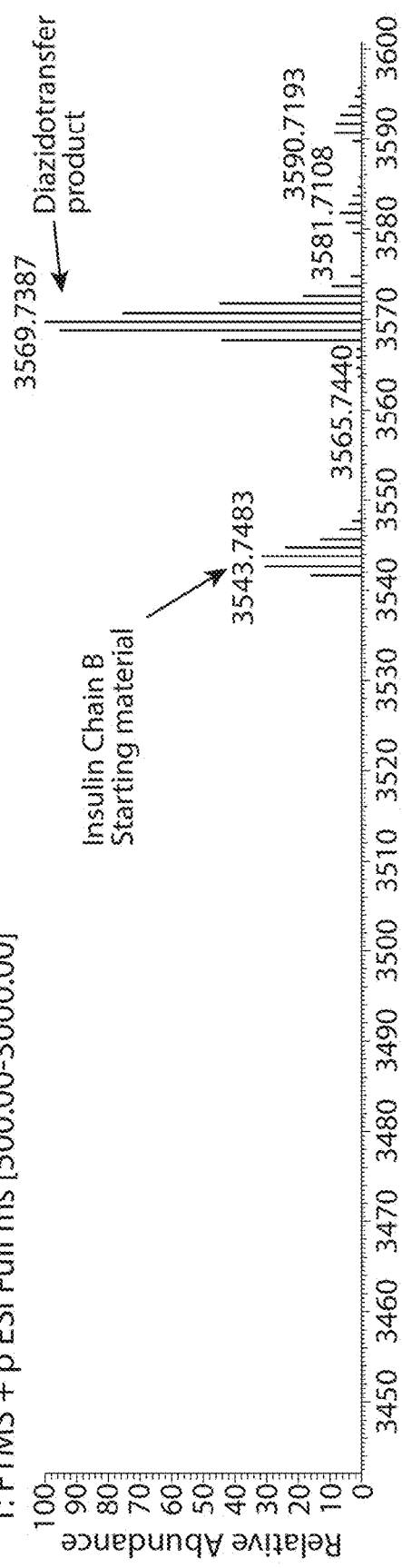
FIG. 16 shows a mass spectrum of an insulin chain B derivative (S-protected using ICM chemistry and activated (converted to the corresponding azide) using diazotransfer chemistry); See FIG. 11.
Figure 17:
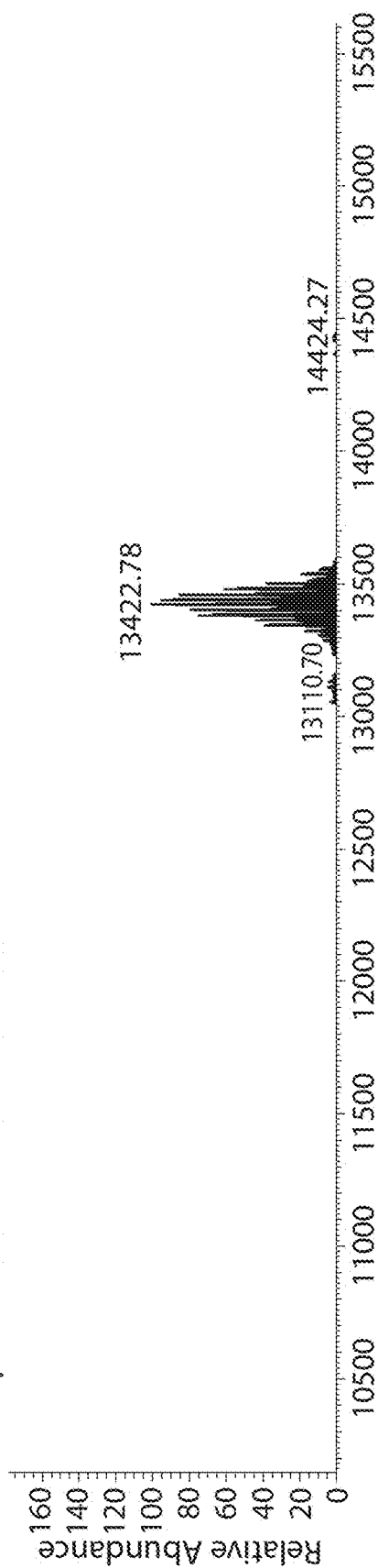
FIG. 17 shows a mass spectrum of the conjugation product (via click chemistry) of the insulin B chain derivative with Q24-bisbiotin-TCO.

Example 6. Insulin as a model system for sample preparation: Insulin was used as a model system. Insulin is a complex small protein that allows testing of sample preparation procedures in a controlled fashion with QC after every operation and without the need for enzymatic digestion. Using the sample preparation protocols described herein (e.g., Examples 3 and 5), Insulin libraries were prepared that result in the isolation of a single peptide, i.e., a single peptide having a terminal lysine (chain B; FIG. 11) on chip (Scheme 3). The yield of azido-lysine labeled Insulin B chain was about 40%.

Example 7. Insulin sample preparation workflows with and without a pre-formed DNA-SV complex are shown in FIGS. 22A-B. Whereas the initial sample preparation for an insulin-Q24-SV complex required 3 steps and two purifications, the use of a pre-formed Q24ds-SV complex reduces the number of manipulations needed to generate the final insulin-DNA-SV complex. The Q24ds-SV complex is highly scalable, allowing access to large amounts of complex. This method facilitates preparations of protein libraries, as the lower number of steps results in less overall material loss.

Figure 19:
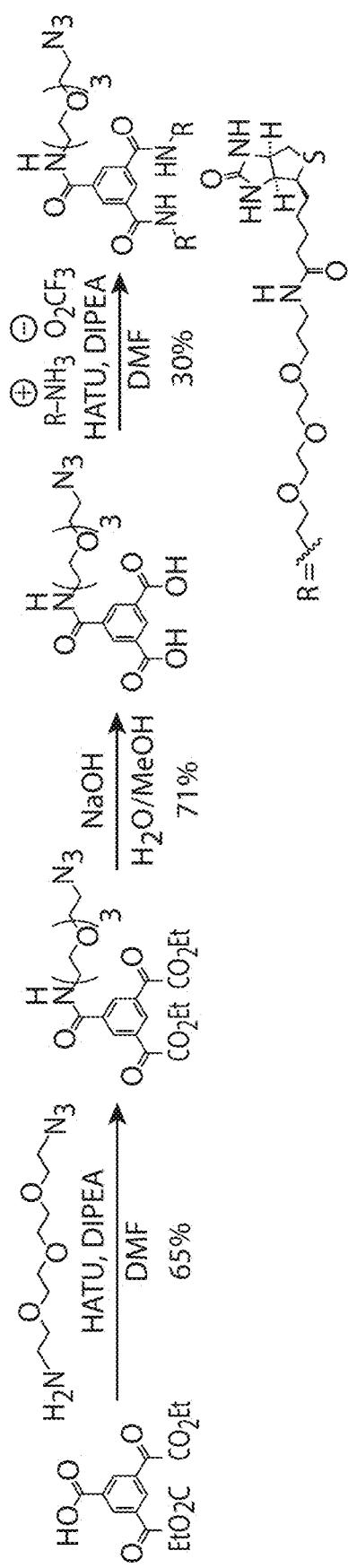
FIG. 19 shows a synthesis scheme for BisBt (bis biotin) azide.

Example 8. Preparation of a peptide-Q24ds-SV complex (FIG. 18B). The Q24 DNA sequence was modified with a BCN (bicycle[6.1.0]nonyne) handle at the 5'-end, which provides a functional moiety for eventual SV (streptavidin) conjugation for surface immobilization. Q24 contains an amine at the 3'-end that can be modified for conjugation to the peptide of interest. See, FIG. 18A. Click chemistry was used to attach the Q24-BCN fragment to bisbiotin. As shown in FIG. 19, the synthesis started from diethyl 1,3,5-benzenetricarboxylate, followed by HATU coupling of azido-PEG3-amine to afford the aromatic azide. Diester hydrolysis was followed by HATU coupling of a biotin-PEG3-amine to afford the desired BisBt azide. In a representative synthesis, the route provided 1 mL of 50 mM azide.

As shown in FIG. 20, a copper-free click reaction between the BCN handle of Q24 and the BisBt azide afforded the intermediate DNA-BisBt complex. After purification of the intermediate complex, a second alkyne click handle was introduced by reacting the 3'-amine of Q24 with BCN-NHS or DBCO-NHS.

Figure 21:
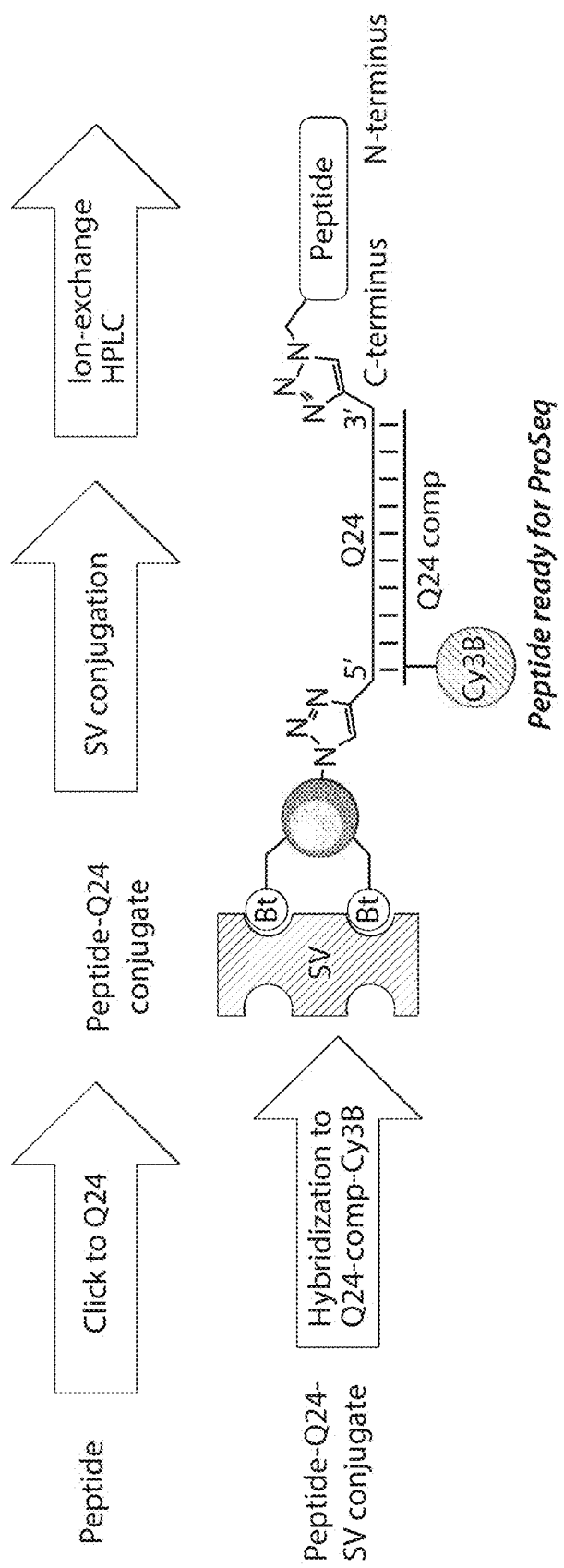
FIG. 21 shows a Peptide-DNA:SV conjugate preparation workflow.
Figure 23A:
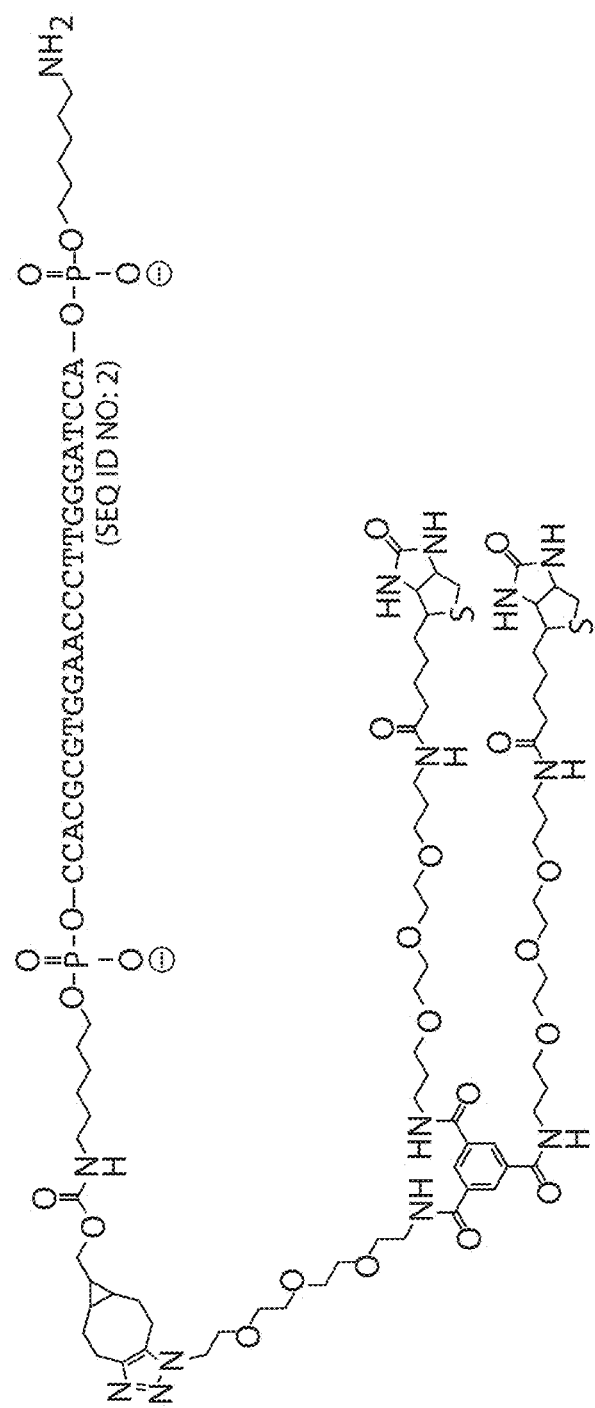
FIG. 23A-B show the structure (FIG. 23A) and mass spectrum (FIG. 23B) of BisBt-Q24 amine.
Figure 23B:
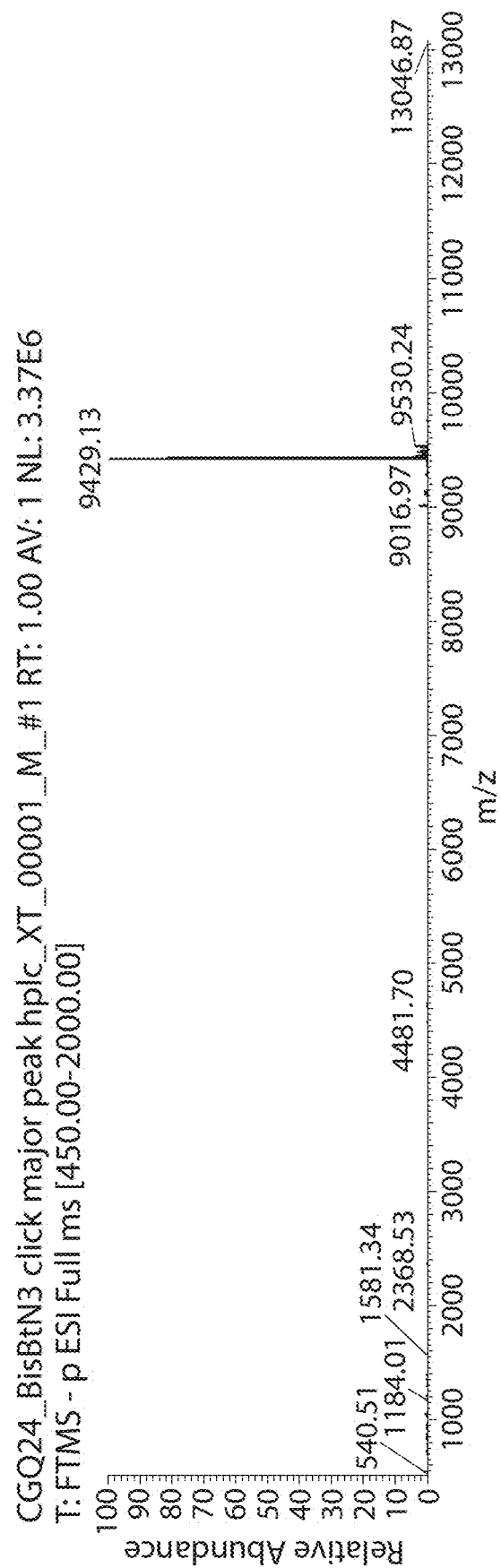
Figure 24A:
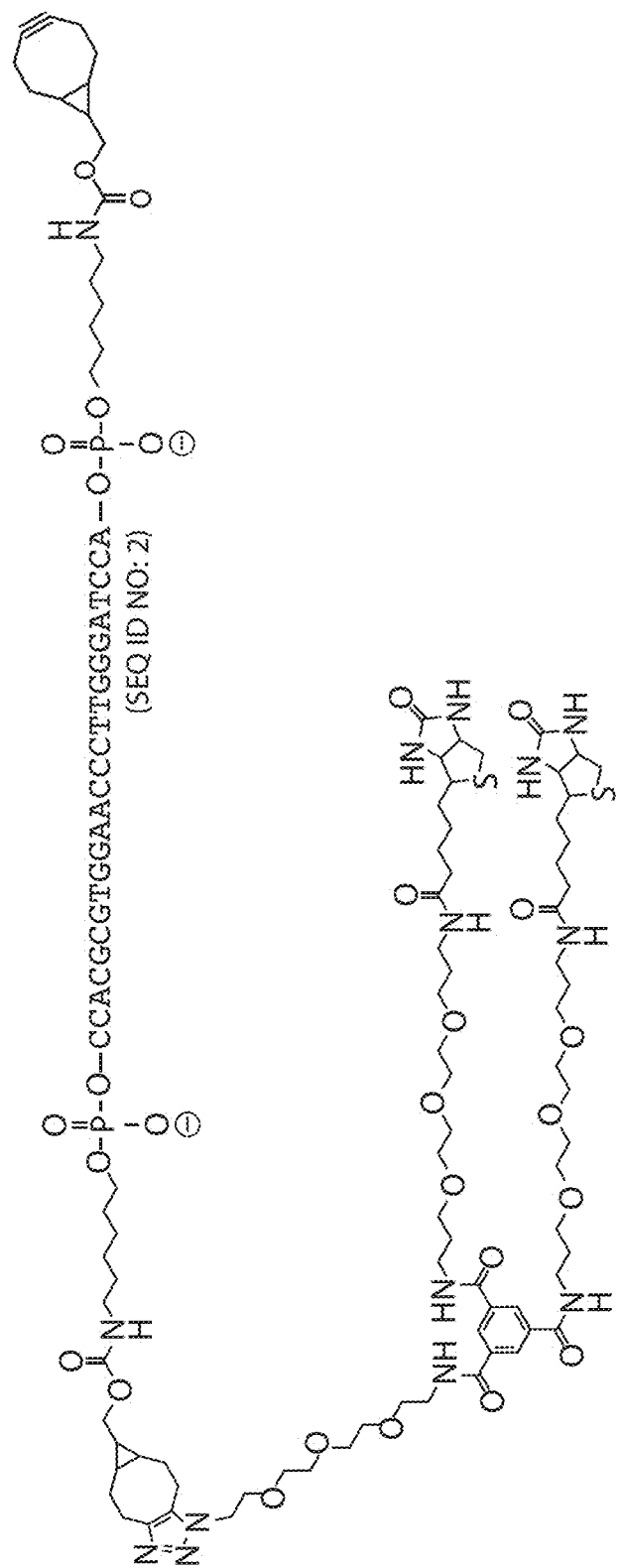
FIG. 24A-B show the structure (FIG. 24A) and mass spectrum (FIG. 24B) of Q24-BisBt-BCN.
Figure 24B:
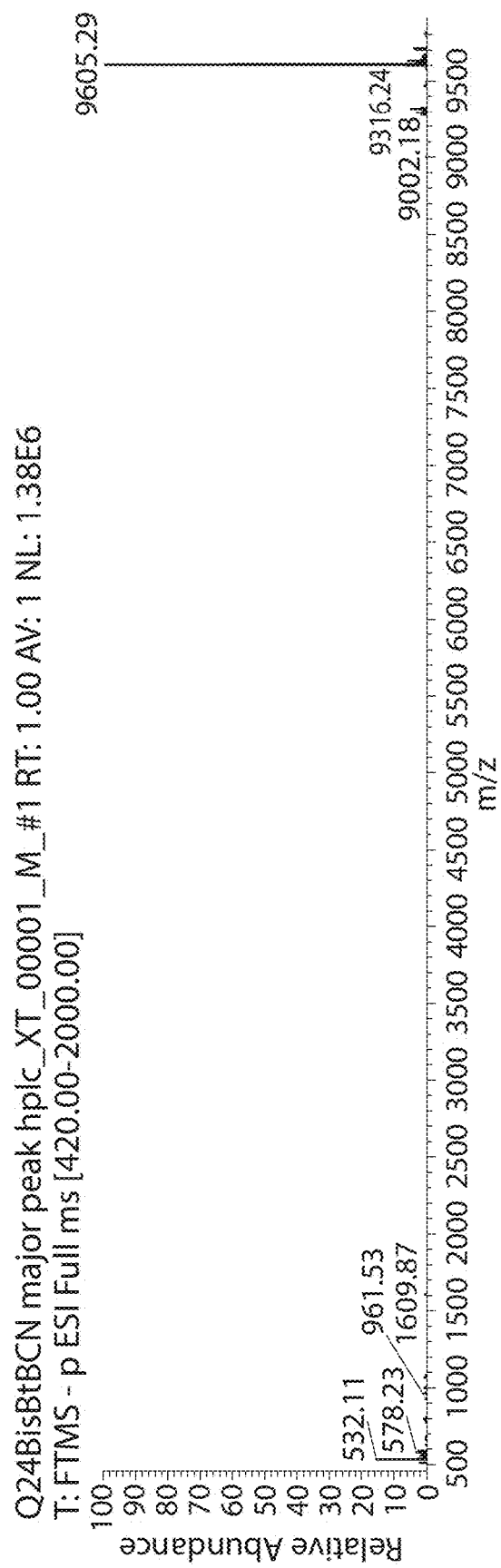
Figure 25A:
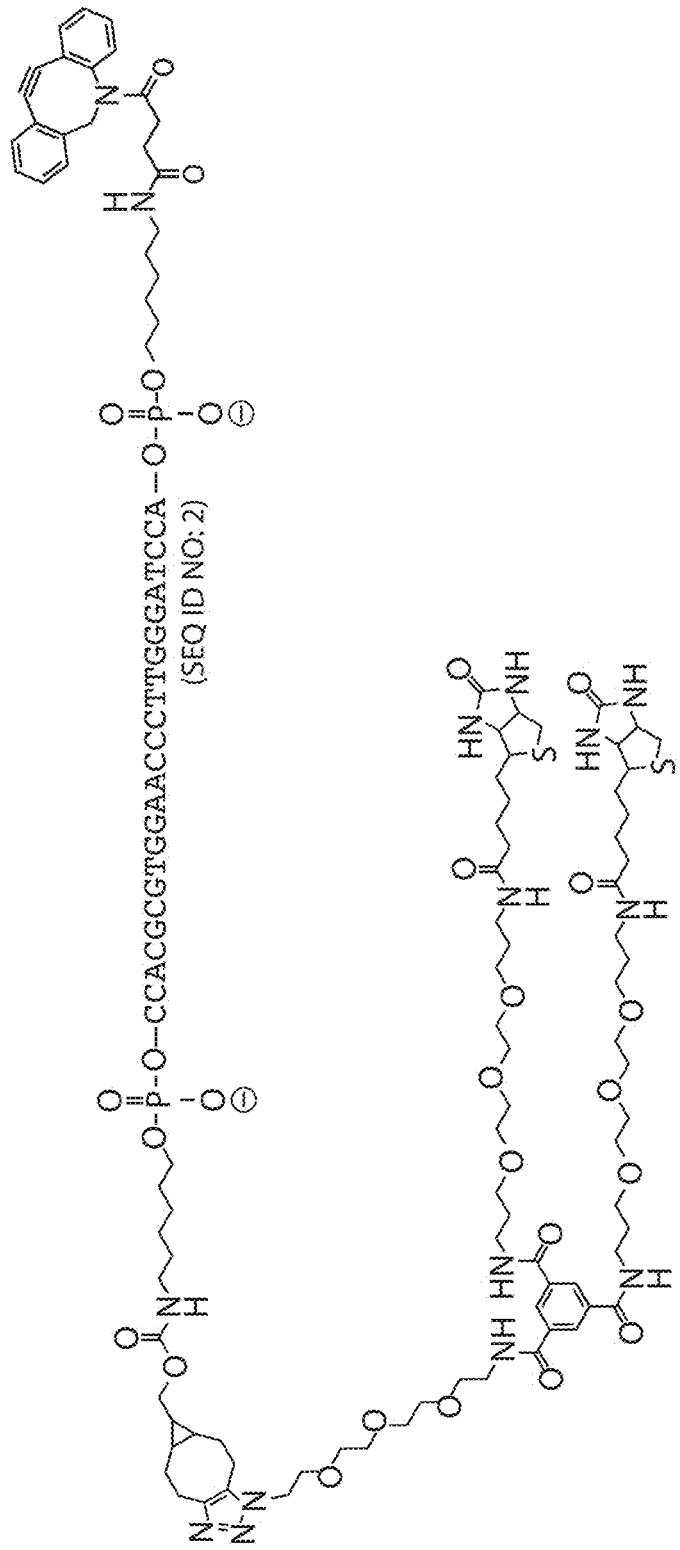
FIG. 25A-B show the structure (FIG. 25A) and mass spectrum (FIG. 25B) of Q24-BisBt-DBCO.
Figure 25B:
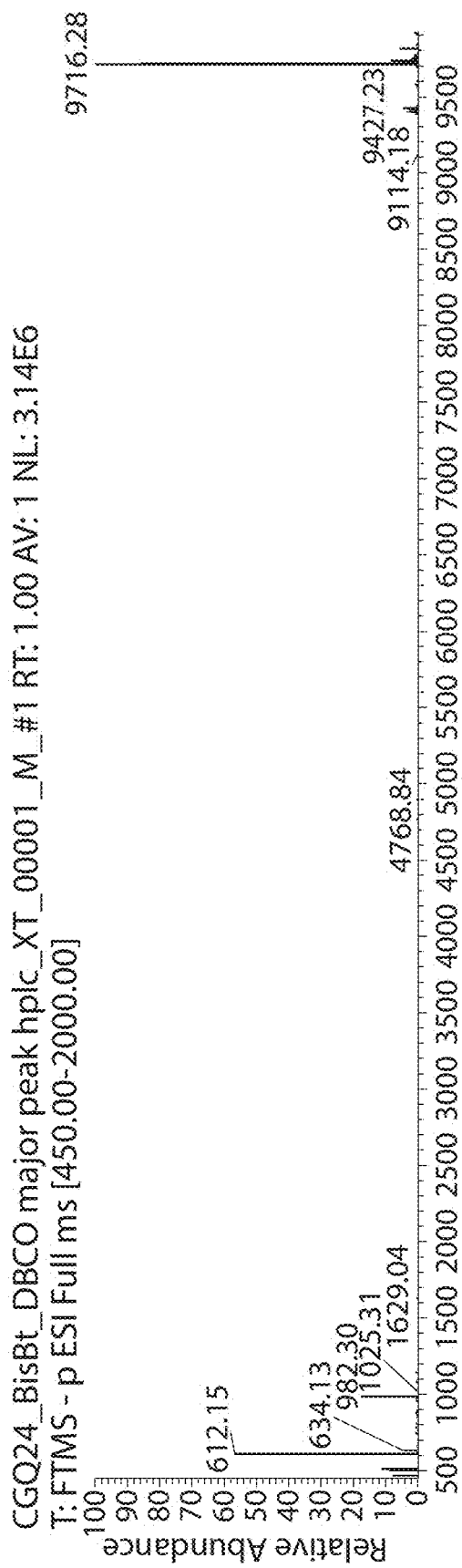
Figure 26A:
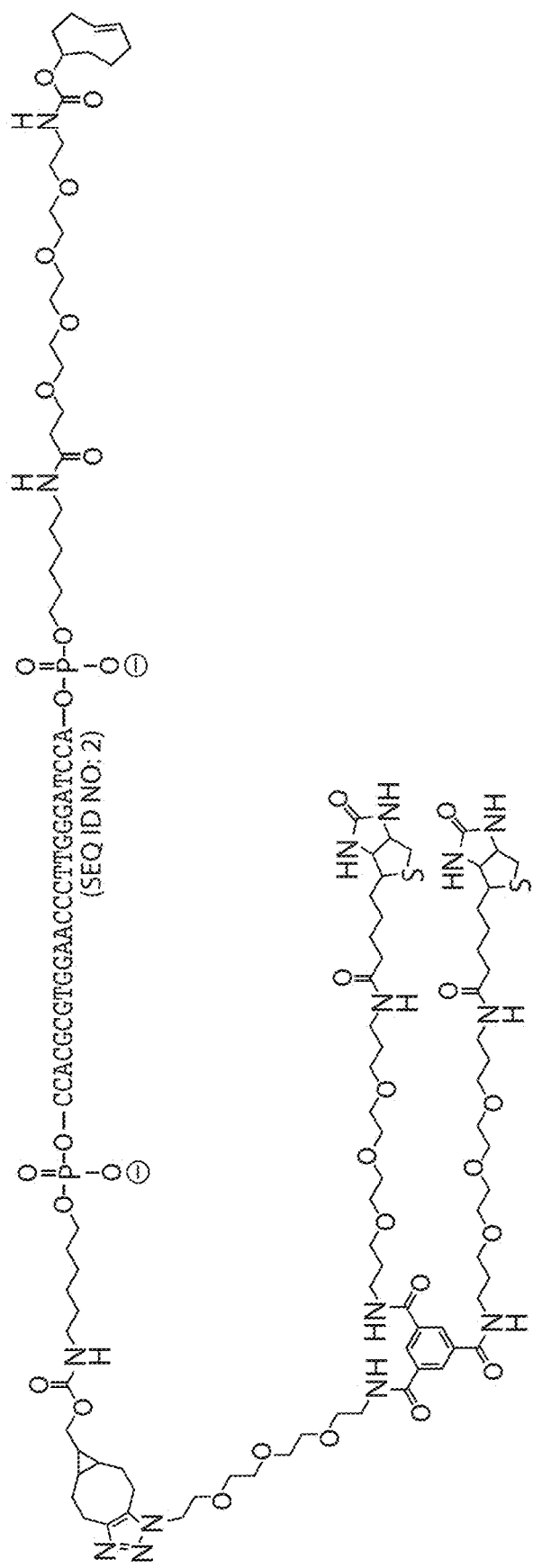
FIG. 26A-B show the structure (FIG. 26A) and mass spectrum (FIG. 26B) of Q24-BisBt-TCO.
Figure 26B:
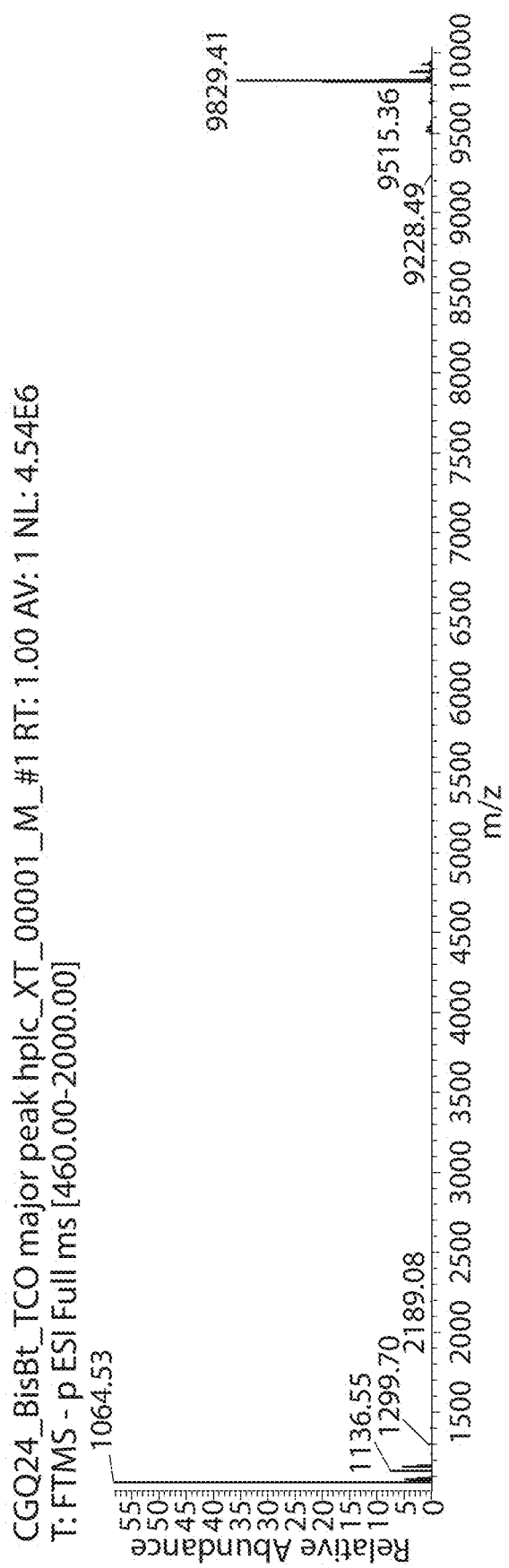

As shown in FIG. 21, several purification steps are used to ensure purity of sample when loading on chip (see schematic in FIG. 21). For example, the peptide with an azide at the C-terminus was clicked to Q24-BisBt-BCN to provide the peptide-Q24 complex. This crude material was conjugated to streptavidin and purified by ion-exchange HPLC to isolate the 1:1 peptide-Q24:SV complex. From here, the single-stranded DNA was hybridized to a Q24 complementary strand labeled with Cy3B at the 3'-end to give the fully formed peptide-Q24ds-SV complex which was ready for immobilization on chip.

In certain workflows, starting with Q24-BisBt-DBCO, conjugation to SV and purification on ion exchange HPLC provided pure 1:1 DNA: SV complex, which was then hybridized to Q24-comp-Cy3B. This entire complex was then conjugated by click chemistry with azido-peptides of interest.

Example 9. Exemplary C-terminal immobilization of peptides via diazotransfer.

1. Prepared a protein sample (50-200 μM in 100 μL) in 100 mM HEPES or sodium phosphate (pH 6-9) with 10-20% acetonitrile.
2. Added TCEP-HCl (200 mM in water, 1 μL; freezer stable). Incubated at 37° C. for 30 minutes.
3. Added freshly dissolved iodoacetamide solution (9 mg in 97.3 μL water for 500 mM, 2 μL; can increase 2-fold) and incubated covered in foil (or in the dark) for 30 minutes at room temperature. Note: Iodoacetamide solutions should be made fresh each time. Old iodoacetamide solutions do not result in proper capping.
4. Added Trypsin (1 μg/μL, 0.5-1 μL), parafilmed tube to reduce evaporation, or used heated lid thermal cycler, and incubate at 37° C. for 12-16 h. Note: The less Trypsin added, the cleaner the sample. Ideal concentration is 1:50 to 1:200 Trypsin Protein (molar).
5. Added potassium carbonate (1 M, 5 μL) to achieve pH ~10-11 (optional: use pH strips; volume potassium carbonate required depends on original buffer).
6. Added copper sulfate solution (4 mM, 13 μL) and imidazole-1-sulfonyl azide solution (200 mM in 200 mM KOH, 1.2 μL) and incubated for 1 hour at room temperature.
7. Combined 50 μL reaction mixture with 50 μL re-suspended polystyrene polyamine beads (2 mM) and incubated with light agitation for 20 minutes.
8. Removed the beads by filtration with a 1 mL syringe fitted with a 0.45 μm syringe filter.
9. Added 6 μL of 1 M acetic acid; volume is 100 μL after filtration.
10. To 48 μL of sample, added DBCO-Q24-SV (50 μM, 6 μL) and incubated for 4 hours at 37° C. (for QC, used 0.7 μl of 500 uM DBCO-Cy3)
11. Equilibrated Zeba 7 kDa or 40 kDa column with 10 mM TRIS, 10 mM Potassium Acetate buffer (pH 7.5): 3×50 μL washes; spin 1 minute at 3,200 rpm (400 rcf=2,200 rpm on Eppendorf 5418).
12. Added sample to column, spinned 1 minute at 3,200 rpm, collected cleaned sample in LoBind Protein 1.5 μL tube.
13. Measured absorbance at 567 nm on NanoDrop. Converted to concentration (μM) by multiplying absorbance by 7.6923.
14. Stored final library at −20° C. or −80° C.

The invention claimed is:

1. A method of selective N-functionalization of a peptide, comprising reacting a plurality of peptides of Formula (XI):

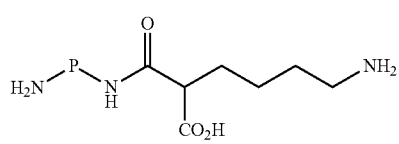
(XI)

or a salt thereof, wherein each P independently is a peptide having an N-terminal amine, with a compound of Formula (XII):

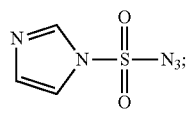
(XII)

under conditions, comprising $Cu^{2+}$, or a precursor thereof, and a buffer having a pH of 10-11; to obtain a plurality of ε-azido compounds of the Formula (XIIIb):

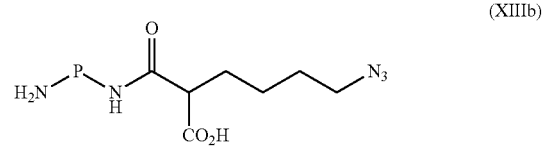
(XIIIb)

or a salt thereof.

2. The method of claim 1, wherein the plurality of peptides of Formula (XI), or a salt thereof, is obtained by subjecting a protein to enzymatic digestion to obtain a digestive mixture comprising the plurality of peptides of Formula (XI), or a salt thereof.

3. The method of claim 1, further comprising reacting the plurality of compounds of Formula (XIIIb), or a salt thereof, with a compound of Formula (XIV):

$$R_6\text{-}L_5\text{-}Z_2$$
(XIV)

wherein $R_6$ is a moiety comprising an alkyne or a strained alkene;
$L_5$ is a linker or is absent; and
$Z_2$ comprises one or more of polyethylene glycol, single-stranded DNA, double-stranded DNA, biotin, and streptavidin;
to obtain a plurality of compounds of Formula (XV):

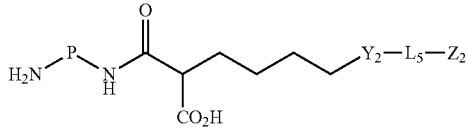 (XV)

or a salt thereof, wherein $Y_2$ is a moiety resulting from a click reaction with the azide moiety of Formula (XIIIb), or a salt thereof, and $R_6$.

4. The method of claim 3, wherein $Z_2$ comprises single-stranded DNA.

5. The method of claim 2, wherein the enzymatic digestion comprises cleaving the C-terminal bonds of lysine and/or arginine residues of the protein.

6. The method of claim 2, wherein the protein comprises sulfide moieties, and wherein the sulfide moieties of the protein are protected prior to the enzymatic digestion.

7. The method of claim 3, wherein $Z_2$ comprises double-stranded DNA.

8. The method of claim 3, wherein $Z_2$ comprises biotin.

9. The method of claim 8, wherein the biotin is bis-biotin (BisBt).

10. The method of claim 3, wherein $Z_2$ comprises streptavidin.

11. The method of claim 3, wherein $R_6$ comprises an alkyne.

12. The method of claim 11, wherein the alkyne is bicycle[6.1.0]nonyne (BCN) or dibenzocyclooctyne (DBCO).

13. The method of claim 3, wherein $R_6$ comprises an alkene.

14. The method of claim 13, wherein the akene is trans-cyclooctene (TCO).

15. The method of claim 3, wherein $L_5$ is absent.

16. The method of claim 1, wherein N-terminal:ε selectivity is at least about 90%.

* * * * *